US009622969B2

(12) United States Patent
Perumal et al.

(10) Patent No.: US 9,622,969 B2
(45) **Date of Patent: *Apr. 18, 2017**

(54) POLYMER CONJUGATED PROTEIN MICELLES

(71) Applicant: South Dakota State University, Brookings, SD (US)

(72) Inventors: Omathanu P. Perumal, Brookings, SD (US); Satheesh K. Podaralla, Creve Coeur, MO (US); Ranjith Kumar Averineni, Portage, MI (US)

( * ) Notice: Subject to any disclaimer, the term of this patent is extended or adjusted under 35 U.S.C. 154(b) by 108 days.

This patent is subject to a terminal disclaimer.

(21) Appl. No.: 14/248,203

(22) Filed: Apr. 8, 2014

(65) Prior Publication Data

US 2014/0370110 A1 Dec. 18, 2014

Related U.S. Application Data

(63) Continuation of application No. 13/404,392, filed on Feb. 24, 2012, now Pat. No. 8,697,098.

(Continued)

(51) Int. Cl.

*A61K 9/107* (2006.01)
*A61K 31/12* (2006.01)

(Continued)

(52) U.S. Cl.

CPC .............. *A61K 9/1075* (2013.01); *A61K 8/11* (2013.01); *A61K 8/64* (2013.01); *A61K 8/671* (2013.01); *A61K 8/86* (2013.01); *A61K 9/0014* (2013.01); *A61K 9/0019* (2013.01); *A61K 9/06* (2013.01); *A61K 9/12* (2013.01); *A61K 9/2031* (2013.01); *A61K 9/2063* (2013.01); *A61K 9/4808* (2013.01); *A61K 31/07* (2013.01); *A61K 31/12* (2013.01); *A61K 31/337* (2013.01); *A61K 31/704* (2013.01); *A61Q 19/00* (2013.01);

(Continued)

(58) Field of Classification Search

None

See application file for complete search history.

(56) References Cited

U.S. PATENT DOCUMENTS

| | | | |
|---|---|---|---|
| 5,324,351 | A | 6/1994 | Oshlack et al. |
| 5,330,778 | A | 7/1994 | Stark et al. |

(Continued)

OTHER PUBLICATIONS

Mehta et al., “Significant . . . media,” Colloids & Surfaces B. Biointerfaces, 81:74-80, 2010.

(Continued)

*Primary Examiner* — Celeste A Roney

(57) ABSTRACT

The invention encompasses micelle assemblies, compositions having micelle assemblies, and methods for preparing micelle assemblies and compositions thereof. The invention also encompasses a prolamine protein conjugated to a polymer, such as a polyethylene glycol (PEG) chain, which conjugates can be used to prepare micelle assemblies. The invention further encompasses methods of encapsulating molecules using the conjugates of the invention. The micelle assemblies can be used for a variety of applications, such as treating cancer, targeting tumors, reducing the toxicity of a drug in vivo, increasing the efficacy of an encapsulated agent in vivo, protecting an encapsulated agent against degradation, and enhancing the water solubility of a drug or other agent.

27 Claims, 36 Drawing Sheets

Related U.S. Application Data

(60) Provisional application No. 61/446,931, filed on Feb. 25, 2011.

(51) Int. Cl.

| | |
|---|---|
| ***A61K 31/704*** | (2006.01) |
| ***A61K 31/07*** | (2006.01) |
| ***A61K 31/337*** | (2006.01) |
| ***B82Y 5/00*** | (2011.01) |
| ***C07K 14/415*** | (2006.01) |
| ***A61K 9/00*** | (2006.01) |
| ***A61K 9/06*** | (2006.01) |
| ***A61K 9/12*** | (2006.01) |
| ***A61K 9/20*** | (2006.01) |
| ***A61K 9/48*** | (2006.01) |
| ***A61K 8/64*** | (2006.01) |
| ***A61K 8/67*** | (2006.01) |
| ***A61Q 19/00*** | (2006.01) |
| ***A61K 8/86*** | (2006.01) |
| ***A61K 8/11*** | (2006.01) |
| *A61K 47/10* | (2017.01) |
| *A61K 47/42* | (2017.01) |

(52) U.S. Cl.
CPC .............. *B82Y 5/00* (2013.01); *C07K 14/415* (2013.01); *A61K 47/10* (2013.01); *A61K 47/42* (2013.01); *A61K 2800/412* (2013.01)

(56) References Cited

U.S. PATENT DOCUMENTS

| | | | | |
|---|---|---|---|---|
| 5,679,377 | A | 10/1997 | Bernstein et al. | |
| 5,837,221 | A | 11/1998 | Bernstein et al. | |
| 5,962,508 | A | 10/1999 | Billoni et al. | |
| 6,020,008 | A * | 2/2000 | Li ............................ | A23G 4/08 426/3 |
| 6,045,777 | A | 4/2000 | Church et al. | |
| 6,090,925 | A | 7/2000 | Woiszwillo et al. | |
| 6,168,804 | B1 | 1/2001 | Samuel et al. | |
| 6,506,410 | B1 | 1/2003 | Park et al. | |
| 6,617,364 | B2 | 9/2003 | Soane et al. | |
| 6,908,625 | B2 | 6/2005 | Lee et al. | |
| 6,939,561 | B2 | 9/2005 | Kwon et al. | |
| 7,160,577 | B2 | 1/2007 | Ahn et al. | |
| 7,564,448 | B2 | 7/2009 | Yi | |
| 8,669,225 | B2 | 3/2014 | Perumal et al. | |
| 2003/0147965 | A1 | 8/2003 | Bassett et al. | |
| 2003/0166509 | A1 | 9/2003 | Edwards et al. | |
| 2004/0091528 | A1 | 5/2004 | Rogers et al. | |
| 2004/0209801 | A1 | 10/2004 | Brand et al. | |
| 2004/0253315 | A1 | 12/2004 | Ogawa et al. | |
| 2005/0209099 | A1 | 9/2005 | Chickering et al. | |
| 2006/0002852 | A1 | 1/2006 | Saltzman et al. | |
| 2006/0093678 | A1 | 5/2006 | Chickering et al. | |
| 2006/0147520 | A1 | 7/2006 | Ruegg | |
| 2006/0198520 | A1 | 9/2006 | Courtney et al. | |
| 2006/0260777 | A1 | 11/2006 | Rashba-Step et al. | |
| 2007/0190080 | A1 | 8/2007 | Friedman | |
| 2007/0264343 | A1 | 11/2007 | Bernstein et al. | |
| 2008/0226742 | A1 | 9/2008 | Srinivas et al. | |
| 2008/0260833 | A1 | 10/2008 | Hirt et al. | |
| 2008/0268061 | A1 | 10/2008 | Jordan et al. | |
| 2009/0036381 | A1 | 2/2009 | Brand et al. | |
| 2009/0041685 | A1 | 2/2009 | Baviskar et al. | |
| 2009/0214419 | A1 | 8/2009 | Therien et al. | |
| 2009/0281068 | A1 | 11/2009 | Moller et al. | |
| 2010/0003336 | A1 | 1/2010 | Deming et al. | |
| 2010/0009007 | A1 | 1/2010 | Darvari et al. | |
| 2010/0015050 | A1 | 1/2010 | Panyam et al. | |
| 2010/0015068 | A1 | 1/2010 | Karp et al. | |
| 2010/0069400 | A1 | 3/2010 | Malstrom et al. | |
| 2010/0111840 | A1 | 5/2010 | Bednarski et al. | |
| 2010/0159019 | A1 | 6/2010 | Yang et al. | |
| 2011/0189249 | A1 | 8/2011 | Liu et al. | |

OTHER PUBLICATIONS

Canadas, "Characterization . . . activity," Biochem 43:9926-9938, 2004.
Kwon, "Diblock . . . delivery," Crit Rev Therap Drug Carrier Syst 15:481-512, 1998.
Parris et al., "Encapsulation . . . particles," J Agr Food Chem 53:4788-4792, 2005.
Xiong et al., "Synthesis . . . segments," Polymer 46:1841-1851, 2005.
Torchilin, "Micellar . . . perspectives," Pharm Res 24:1-16, 2007.
Veronese et al., "PEGylation . . . delivery," Drug Disc Today 10:1451-1458, 2005.
Hurtado-Lopez et al., "Zein . . . enzymes," J Micoencap 23:303-314, 2006.
Lawton, "Zein . . . use," Cereal Chem 79:1-18, 2002.
Liu et al., "Microspheres . . . system," Biomat 26:109-115, 2005.
Patel et al., "Hydrogel Biomaterials," in Biomed Eng—Frontiers and Challenges, Fazel, ed., p. 275-296, 2011.
Francis et al., "Polymeric . . . how," Pure Appl Chem 76:1321-1335, 2004.
Batrakova et al., "Pluronic Block Polymers," J Control Rel 130:98-106, 2008.

* cited by examiner

SKIN PENETRATION OF FREE CURUMIN IN THE XZ AXIS

SKIN PENETRATION OF CURUCMIN MICELLE IN THE XZ AXIS; SC- STRATUM CORNEUM

PENETRATION OF CURCUMIN MICELLES
THROUGH HAIR FOLLICLES (XY SURFACE VIEW)

Percentage of applied retinol at 48 hours in skin and in receptor medium

POLYMER CONJUGATED PROTEIN MICELLES

CROSS REFERENCE TO RELATED APPLICATION

This application is a Continuation of U.S. Ser. No. 13/404,392, filed on Feb. 24, 2012, now U.S. Pat. No. 8,697,098, and claims benefit under 35 U.S.C. §119(e) to U.S. Provisional Application No. 61/446,931, filed Feb. 25, 2011, which is incorporated by reference herein in its entirety.

BACKGROUND OF THE INVENTION

Field of the Invention

The present invention relates generally to drug delivery technologies, and more specifically to a nanomicelle drug delivery system, including methods for preparing such a system using a hydrophobic water insoluble protein and a water soluble polymer, which micelles may include polyethylene glycol (PEG) or other hydrophilic moieties that may be covalently attached to hydrophobic water insoluble proteins such as prolamines to form an amphiphilic conjugate for preparing the nanomicelle drug delivery system.

Background Information

Approximately 40% of pharmaceutical compounds have poor aqueous solubility, which is a major limiting factor for a new drug to successfully pass through clinical trials (Lipinski (2002), Am Pharm Rev 5:82-85). Numerous approaches have been used to solubilize hydrophobic drugs for improving their delivery to patients. Several examples of such approaches include milling, complexing with cyclodextrins, forming salts, and using surfactants or polymeric micelles. Each of these approaches has certain advantages and disadvantages so improved approaches to solubilizing drugs are eagerly sought.

Polymeric micelles are self-assembled amphiphilic block or graft copolymers. Polymeric micelles have attracted attention as promising colloidal drug delivery systems (Torchilin, J Controlled Release 2001, 73, 137; Allen et al., Colloids and Surfaces B: Biointerfaces 1999, 16, 3; and Otsuka et al., Current Opinion in Colloid & Interface Science 2001, 6, 3). In these colloidal systems, the hydrophobic block typically forms the core, essentially forming a "microcontainer" for a lipophilic cargo molecules (Kataoka et al., Adv. Drug Delivery Rev. 2001, 47, 113). The hydrophilic portion of the micelle forms the outer shell, stabilizing the interface between the core and the external aqueous environment.

Compared to surfactant-based micellar systems, polymer-based micelles can display apparent advantages such as lower critical micelle concentration (CMC) and reduced toxicity. Despite these advantages, the use of known micellar systems is somewhat limited due to unsuitable biodegradability, biocompatibility, encapsulation efficiency, stability, clinical side effects of the formulations, and the difficulty and cost associated with preparation of known micellar formulations. Accordingly, there is a need for additional micellar systems that possess some of the known advantages associated with micellar drug delivery systems, but that have increased biocompatibility and are easier and less expensive to prepare.

SUMMARY OF THE INVENTION

The invention provides a novel nanomicelle platform technology for delivery of water insoluble compounds. Also provided are methods for preparing micelles using a hydrophobic water insoluble protein and a water soluble polymer, and methods of using micelle compositions, for example, for in vivo drug delivery. Polyethylene glycol (PEG) or other hydrophilic moieties can be covalently attached to hydrophobic water insoluble proteins such as zein, to form a highly useful amphiphilic conjugate for preparing the nanomicelle drug delivery systems.

Accordingly, the invention provides a micelle comprising biocompatible and biodegradable copolymers, wherein the copolymers include a hydrophobic block and a hydrophilic block; the hydrophobic block includes a hydrophobic prolamine protein covalently conjugated to the hydrophilic block and the hydrophilic block includes a hydrophilic polyethylene glycol moiety having a molecular weight of at least about 3 kDa; prolamine protein chains of the amphiphilic copolymers orient toward the interior of the micelle, and polyethylene glycol moiety of the amphiphilic copolymers orient toward the exterior of the micelle; and the diameter of the micelle is about 10 nm to about 300 nm.

The biocompatible and biodegradable copolymers may in include graft copolymers and/or block copolymers. The critical micelle concentration of the micelle in water can be about 0.015 g/L to about 0.035 g/L, about 0.02 g/L to about 0.03 g/L, or about 0.25 g/L, for example, at about 27° C. The hydrophobic drug can have a Log P of about 1, about 2, about 3, about 4, about 5, about 6, about 7, or about 1 to about 7, or a range from any integer from 1 to 7.

The hydrophobic prolamine protein can be zein, gliadin, hordein, kafirin, or a combination thereof. The hydrophilic polyethylene glycol moiety can have a molecular weight of about 4 kDa to about 220 kDa. The hydrophilic polyethylene glycol moiety can have a molecular weight of about 4 kDa to about 20 kDa.

The micelles can further include a plurality of cargo molecules in the core of the micelle. The cargo molecules can include, for example, one or more drugs, proteins, nucleic acids, hormones, receptors, diagnostic agents, imaging agents, or a combination thereof. The drug can be an antioxidant, an anti-inflammatory drug or an anticancer drug. In one embodiment, the drug is curcumin or doxorubicin. In another embodiment, the imaging agent is Nile red.

In another embodiment, the drug is a retinoid. Examples of suitable retinoids include retinol, 13-trans-retinoic acid (tretinoin), 13-cis-retinoic acid (isotretinoin), 9-cis-retinoic acid (alitretinoin), retinaldehyde, etretnate, acitretin, α-carotene, β-carotene, γ-carotene, β-cryptozanthin, lutein, zeaxanthin, or a combination thereof.

The invention also provides a pharmaceutical or cosmetic composition comprising a plurality of micelles described herein and a pharmaceutically or cosmetically acceptable diluent, excipient, or carrier. The pharmaceutical or cosmetic composition may be, for example, in the form of a dispersion, tablet, capsule, injectable formulation, aerosol formulation, gel, ointment, cream, lotion, or shampoo.

The invention further provides a method of preparing a micelle. The method may include adding a buffer to an aqueous suspension to precipitate PEGylated prolamine from a hydroalcoholic solvent to form an aqueous dispersion of PEGylated prolamine, and removing the alcohol and unreacted PEG and glycine in the dispersion by dialysis against deionized water.

The invention additionally provides a method of preparing a micelle wherein the method includes removing alcohol from an aqueous suspension of PEGylated prolamine to form a dry film of PEGylated prolamine; and resuspending the PEG-zein film in water or a buffer followed by dialysis against deionized water, for example, to remove unencapsulated hydrophobic molecules, to provide a plurality of the micelles, for example, in a water and buffer composition, such as a dispersion. In this method, after PEGylation of zein, the ethanol can be removed by evaporation, for example, in a rotary evaporator, to form a dry film. The dry film can then be reconstituted in water and dialyzed against deionized water, for example, to remove unencapsulated hydrophobic compounds, to form micelles in the aqueous phase.

Accordingly, the invention also provides a method of preparing the micelles described herein by dissolving a polyethylene glycol compound and a prolamine protein in a hydroalcoholic solvent to form a first mixture; wherein one terminus of the polyethylene glycol compound is monoalkylated and a second terminus comprises a reactive group, and the polyethylene glycol compound has a molecular weight of at least about 3 kDa; heating the first mixture to form PEGylated prolamine in an aqueous suspension, and optionally quenching excess reactive groups of the polyethylene glycol compound in the aqueous suspension and removing alcohol and unreacted PEG and glycine in the dispersion by dialysis against deionized water followed by lyophilization.

The remainder of the method can follow one of two paths. In one embodiment, the method includes (a) adding PEG-zein in a hydroalcoholic solvent and removing alcohol by dialysis against deionized water to form a plurality of micelles in a buffer and water composition. In another embodiment, the method includes (b) removing the alcohol of the aqueous suspension to form a dry film of PEGylated prolamine; and resuspending the PEGylated prolamine of the dry film in water or a buffer followed by dialysis, for example, to remove unencapsulated hydrophobic compounds, to form micelles in the aqueous phase.

Thus, once prepared, the PEG-prolamine can be dissolved in hydroalcoholic solution at a specific concentration. When following the film method of preparation, the alcohol is removed to form a PEG-zein film. The film is then reconstituted with deionized water to form PEG-zein micelles. This composition can then be dialyzed against water to remove unencapsulated compounds. Formation of the aqueous dispersion can then be followed by lyophilization to obtain a PEG-zein micelle powder.

When following the dialysis method of preparation, the alcohol is removed by dialyzing against deionized water to form micelles. The aqueous dispersion may then be lyophilized to provide a PEG-zein micelle powder. Accordingly, the methods may include lyophilizing a plurality of the micelles in a composition such as a dispersion to provide a plurality of isolated micelles in the form of a powder.

In any of the methods of preparation, useful cargo molecules, for example, a therapeutic agent or an imaging agent can be dissolved in a solvent system and can be added to the first mixture, resulting in the formation of a cargo loaded micelles, such as drug loaded micelles. The encapsulation efficiency of the micelles can be about 60% to about 95%. The method can include dispersing a plurality of the micelles in a buffer solution to provide a therapeutic composition of drug loaded micelles.

In one embodiment, the invention provides a method to inhibit cellular P-glycoprotein (P-pg) efflux pumps in a cell comprising contacting a cell with a plurality of micelles described herein, thereby inhibiting the cellular P-pg efflux pumps in the cell.

In another embodiment, the invention provides a method to enhance the uptake of a therapeutic agent in a drug-resistance cancer cell comprising contacting the cell with a plurality of micelles described herein, thereby enhancing the uptake of the therapeutic agent in the drug-resistance cancer cell.

In another embodiment, the invention provides a method to enhance the water solubility of a lipophilic compound comprising encapsulating the lipophilic compound in a micelle as described herein, thereby enhancing the water solubility of the lipophilic compound.

In another embodiment, the invention provides a method to enhance the chemical stability of a compound comprising encapsulating the compound in a micelle as described herein, thereby enhancing the chemical stability of the compound.

In another embodiment, the invention provides a method to provide sustained release of a compound from a composition including encapsulating a compound in a micelle as described herein and contacting a biological medium with the encapsulated compound, where the compound is released from the micelle over a period of about 1 hour to about 14 days.

In another embodiment, the invention provides a method to provide a compound to a subject or a sample in a non-immunogenic and biocompatible formulation comprising contacting the subject or the sample with a micelle or a composition described herein, thereby providing the non-immunogenic and biocompatible formulation to the subject or the sample. In one aspect, such formulation may improve systemic circulation of the encapsulated compound.

In another embodiment, the invention provides a method to increase the skin penetration and retention of an active agent or imaging agent comprising encapsulating the active agent or imaging agent in a micelle as described herein and contacting skin with a composition comprising the micelle, thereby increasing the skin penetration of the active agent or imaging agent compared to the skin penetration of the active agent or imaging agent in the absence of the micelle.

In another embodiment, the invention provides a method to enhanced tumor accumulation of drug comprising encapsulating a drug in a micelle as described herein, and administering to a subject that has a tumor a plurality of the micelles, where the encapsulated drug accumulates at the tumor to a greater degree than a drug that is administered to a subject in the absence of the micelles.

In another embodiment, the invention provides a method to reduced drug accumulation in non-tumor bearing tissues in a mammal comprising encapsulating a drug in a micelle as described herein, and administering to a subject that has a tumor a plurality of the micelles, where the encapsulated drug accumulates in non-tumor bearing tissues to a lesser degree than a drug that is administered to a subject in the absence of the micelles.

In another embodiment, the invention provides a method to increase the efficacy of a drug comprising administering a plurality of loaded micelles as described herein to a subject, where the efficacy of the drug is increased compared to administration of the drug in the absence of the micelles.

In yet another embodiment, the invention provides a method to reduce the toxicity of a drug comprising administering a plurality of loaded micelles as described herein to a subject, where the toxicity of the drug is reduced compared to administration of the drug in the absence of the micelles.

The invention also provides a copolymer of Formula I:

$$Z\text{-}(PEG)_n \qquad (I)$$

where Z is a prolamine protein, "PEG" is a polyethylene glycol moiety having a molecular weight of at least about 3 kDa, and n is about 1 to about 100, or about 5 to about 50.

The prolamine protein can be, for example, white zein, yellow zein, gliadin, hordein, or kafirin. A variety of PEG moieties with varying molecular weights can be conjugated to the prolamine. For example, molecular weight of the PEG moiety may be 1 kDa to about 220 kDa, about 2 kDa to about 20 kDa, about 3 kDa to about 20 kDa, about 4 kDa to about 20 kDa, about 4 kDa to about 10 kDa, or about 5 kDa.

Formula I can include graft copolymers of a prolamine and PEG; and block copolymers of a prolamine and PEG (diblock or multiblock copolymers, such as triblock copolymers). Examples include Formulas Z-g-PEG (graft copolymer) (II)

Z-b-PEG (diblock copolymer) (III)

Z-b-PEG-b-Z (triblock copolymer) (IV)

PEG-b-Z-b-PEG (triblock copolymer) (V)

Copolymers of Formula I are useful intermediates for preparing aggregates that can be used in drug delivery applications, such as for the delivery of hydrophobic therapeutic agents.

The invention further provides a composition comprising a plurality of copolymers or micelles as described herein in a liquid suspension, dispersion or solution, such as an formulation.

The invention also provides a method for preparing an encapsulate of the invention comprising combining a plurality of copolymers of Formula I and a molecule (e.g., a therapeutic agent) in a solvent or solvent system, and allowing the copolymers of Formula Ito aggregate around the molecule, to provide the encapsulate (i.e. the molecule encapsulated or surrounded by a plurality of copolymers of Formula I).

The invention also provides a composition comprising a diluent and a micelle formed from a plurality of copolymers of Formula I surrounding a molecule (e.g., a therapeutic agent).

The invention also provides a pharmaceutical composition comprising an encapsulate of the invention (i.e., a therapeutic agent encapsulated or surrounded by a plurality of copolymers of Formula I, such as in a micelle); and a pharmaceutically acceptable carrier. Alternatively, the therapeutic agent may be conjugated or complexed to the prolamine in the hydrophobic core and/or to the hydrophilic polymeric shell. The micelle can also be used to encapsulate multiple therapeutic agents, and/or multiple therapeutic agents can be complexed/conjugated to the core and/or shell. In addition to or in place of therapeutic agents, the micelles can be used to carry diagnostic and/or imaging agents, and the like.

The invention also provides a method for delivering a therapeutic agent to an animal in need of treatment with the agent comprising administering an encapsulate of the invention to the animal, where the encapsulate includes the therapeutic agent inside a micellar assembly of copolymers of Formula I.

The invention further provides for the use of the micellar compositions described herein for use in medical therapy. The medical therapy can be treating cancer, for example, breast cancer, lung cancer, pancreatic cancer, prostate cancer, or colon cancer. The invention also provides for the use of a micellar composition as described herein for the manufacture of a medicament to treat such cancers. The medicament can include a pharmaceutically acceptable diluent, excipient, or carrier.

The invention further provides for the treatment of skin and follicular disorders, such as acne, and may be used in the treatment of hair loss, seborrhetic eczema, folliculitis, cutaneous malignancies, psoriasis, keratinization disorders, skin discoloration, wounds, and photoaging.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

In FIG. 5(*a*), ethylene groups of PEG are observed at 3.56 ppm and the protein/amide peak is observed at 3.36 ppm. In FIG. 5(*b*), ethylene bonds of PEG are observed at 3.56 ppm, while the protein/amide peak at 3.36 ppm is absent because the hydrophobic zein core is not soluble in $D_2O$.

and viable epidermis (20-100 μm) using FLUOVIEW™ software (Olympus, Center Valley, Pa.).

Figure 38:
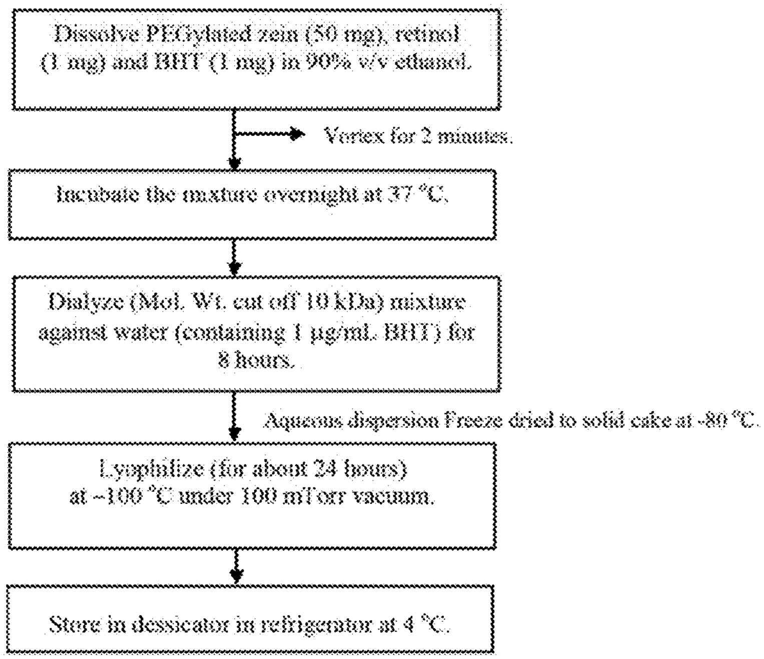

FIG. 38 illustrates by means of a flow chart the general steps to prepare retinol loaded PEGylated zein micelles using a dialysis method, according to one embodiment. In FIGS. 38-39 and 43-46, BHT refers to butylated hydroxyltoluene (2,6-di-tert-butyl-4-methylphenol).

Figure 39:
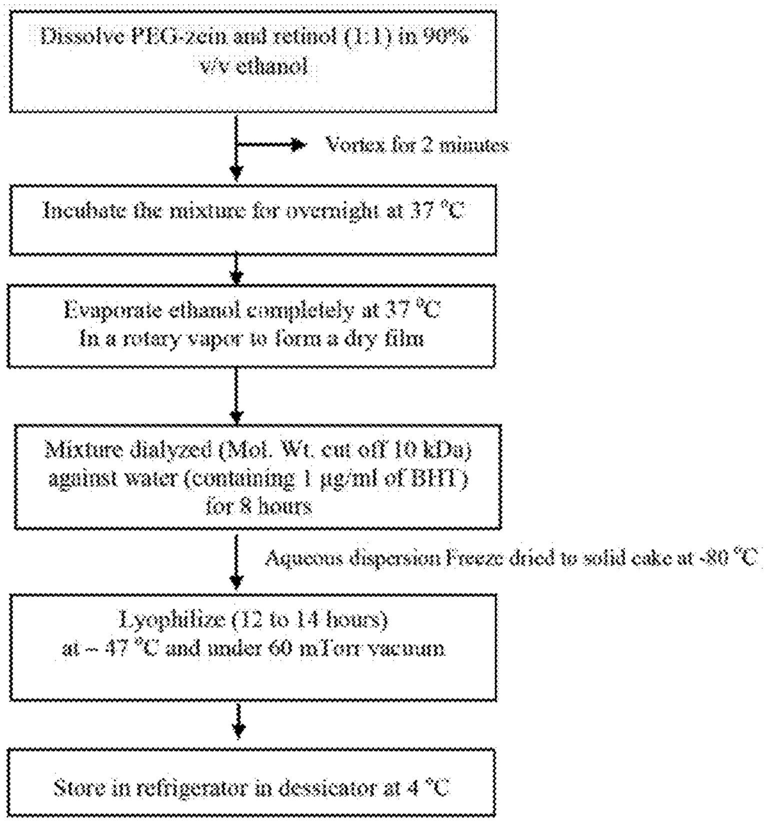

FIG. 39 illustrates by means of a flow chart the general steps to prepare retinol loaded PEGylated zein micelles using a film method, according to one embodiment.

Figure 40:
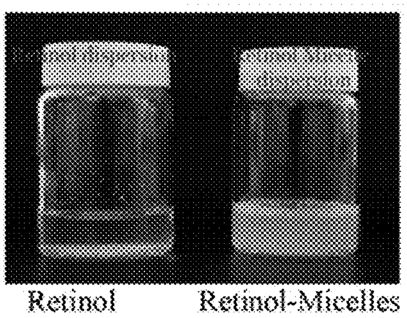

FIG. 40 illustrates the water dispersibility of free retinol and retinol loaded nanomicelles, from left to right.

Figure 41:
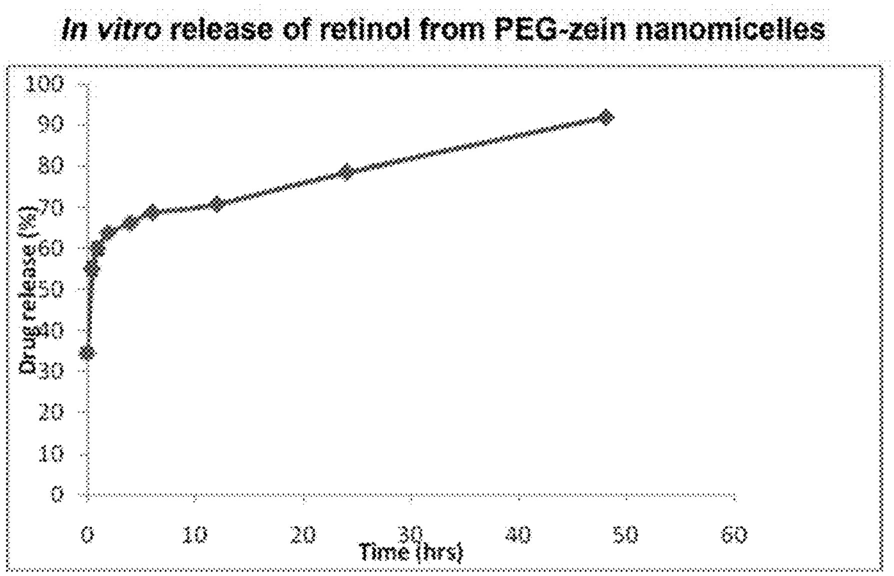

FIG. 41 illustrates the in vitro release of retinol from PEG-zein nanomicelles in phosphate buffer (pH 7.4). The retinol concentration was measured by UV-visible spectrophotometry at 320 nm. Each data point is an average±SD (n=3) (mean±SEM; n=3).

Figure 42:
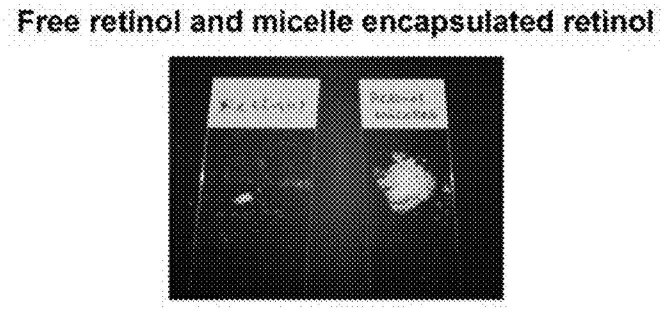

FIG. 42 illustrates free retinol, lyophilized and retinol micelles, from left to right. The figure shows the hygroscopic nature of pure retinol and that the retinol micelles are non-hygroscopic free flowing powders.

Figure 43:
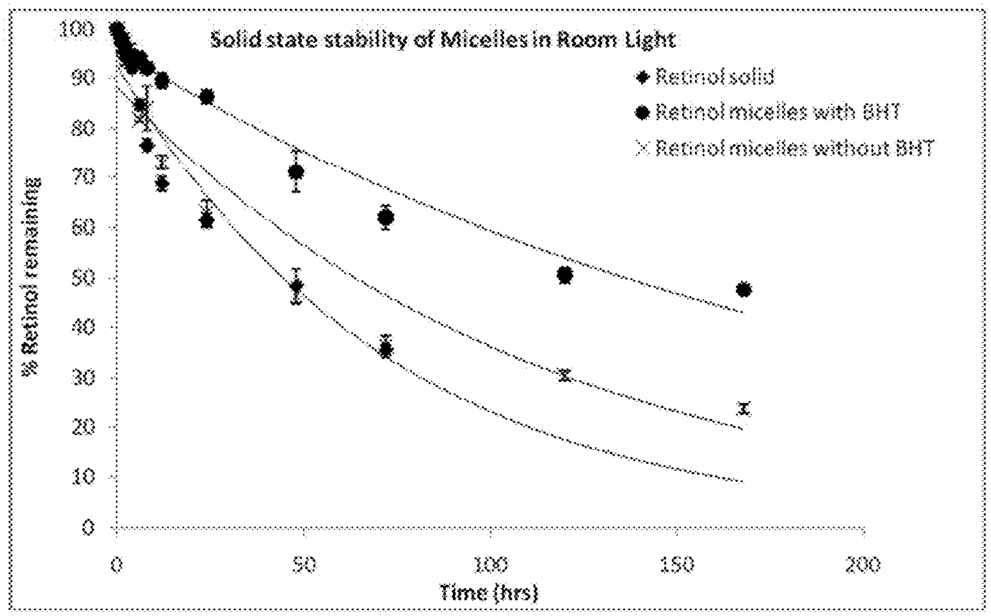

FIG. 43 illustrates the solid state stability of retinol loaded nanomicelles when stored under normal room light. Free retinol and retinol micelles were kept in a clear glass vials and exposed to room light for one week. The retinol remaining at different time points was measured by UV-visible spectrophotometry at 320 nm (mean±SD; n=3).

Figure 44:
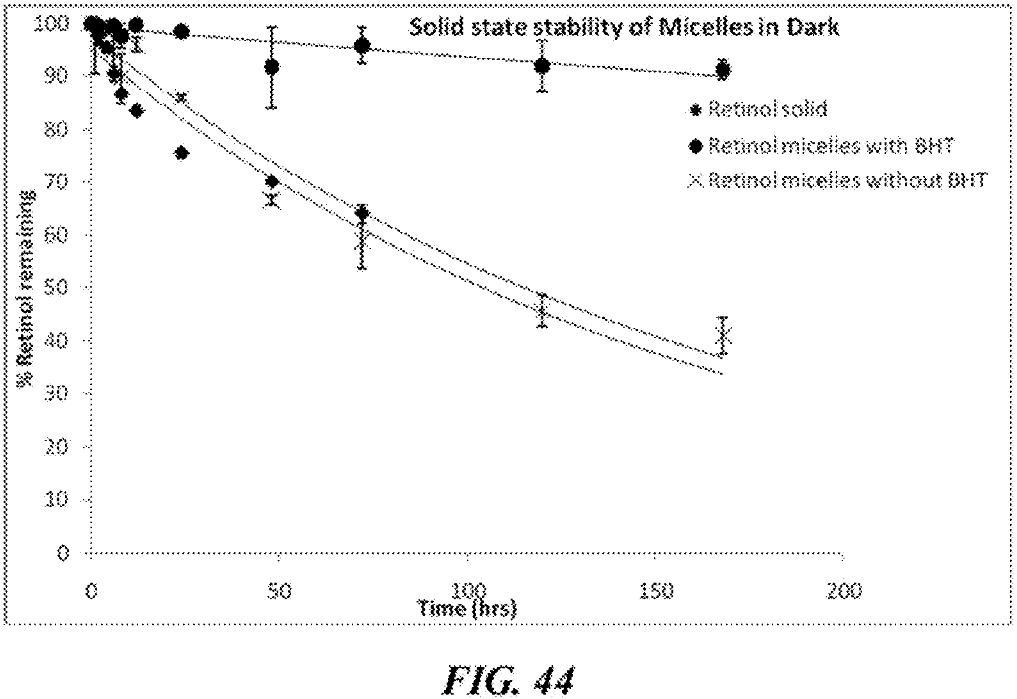

FIG. 44 illustrates the solid state stability of retinol loaded nanomicelles when stored when stored in the absence of light. Free retinol and retinol micelles were kept in a clear glass vials and stored in a dark cabinet for one week. The retinol remaining at different time points was measured by UV-visible spectrophotometry at 320 nm (mean±SD; n=3).

Figure 45:
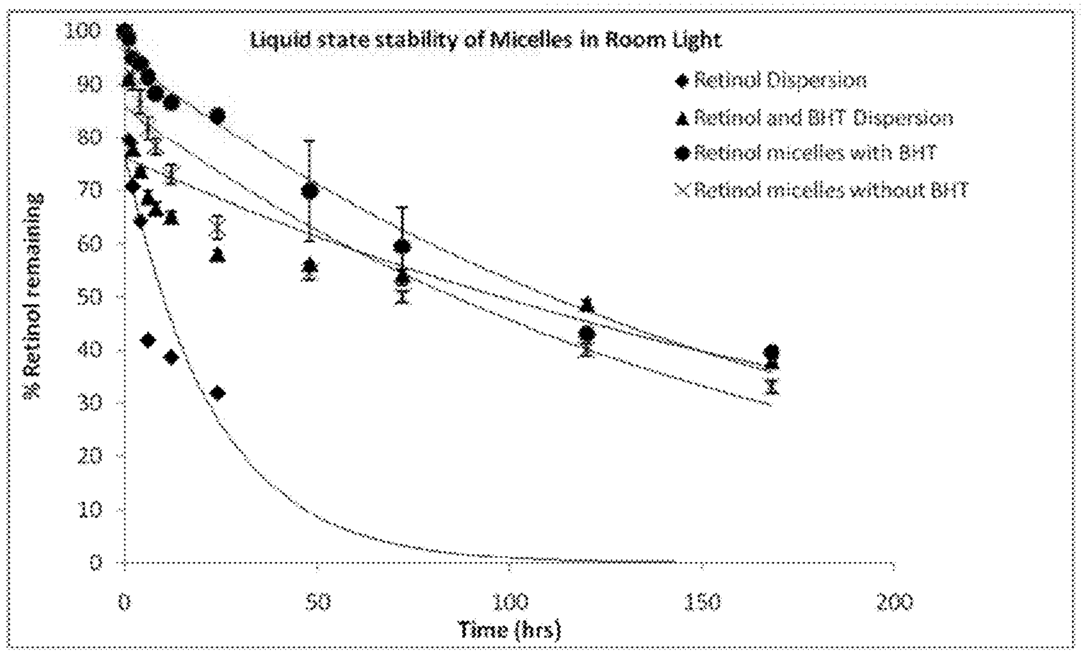

FIG. 45 illustrates the liquid state stability of retinol loaded nanomicelles when stored under normal light. Free retinol and retinol micelles were dispersed in phosphate buffer (pH 7.4) and stored in a clear glass vials in room light for one week. The retinol remaining at different time points was measured by UV-visible spectrophotometry at 320 nm (mean±SD; n=3).

Figure 46:
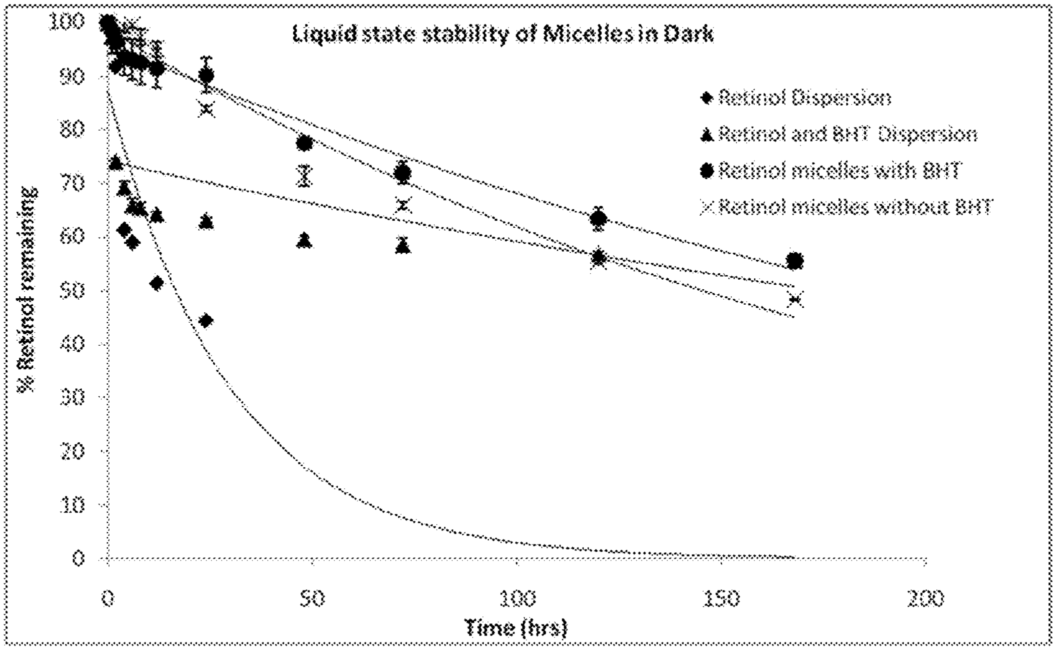

FIG. 46 illustrates the liquid state stability of retinol loaded nanomicelles when stored protected from light in dark cabinet. Free retinol and retinol micelles were dispersed in phosphate buffer (pH 7.4) and stored in a clear glass vials in a dark cabinet for one week. The retinol remaining at different time points was measured by UV-visible spectrophotometry at 320 nm (mean±SD; n=3).

Figure 47:
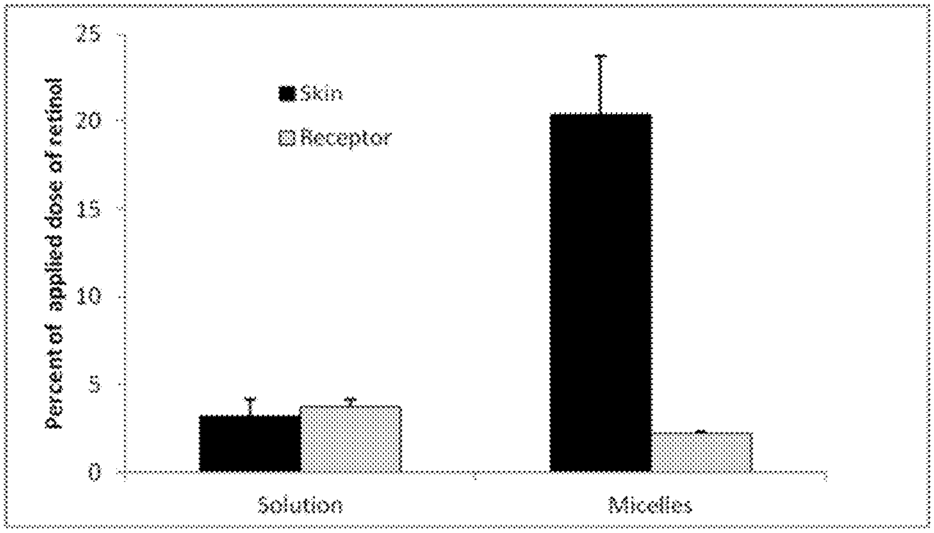

FIG. 47 illustrates the percentage of applied retinol at the end of 48 hours in porcine skin and in receptor medium after treatment with free retinol and retinol encapsulated in PEG-zein micelles. Excised porcine skin was sandwiched between the two compartments of a vertical diffusion cell. The receptor medium consisted of phosphate buffer (pH 7.4) maintained at 37° C. and stirred using a magnetic bead. Free or encapsulated retinol dispersion in phosphate buffer (pH 7.4) was loaded in the donor chamber. At the end of the study, the retinol concentration in the skin and receptor compartment was measured by radiochemical method using $^3$H labeled retinol. The skin was digested using 0.1M sodium hydroxide to determine the retinol concentration (mean±SD; n=6).

Figure 48:
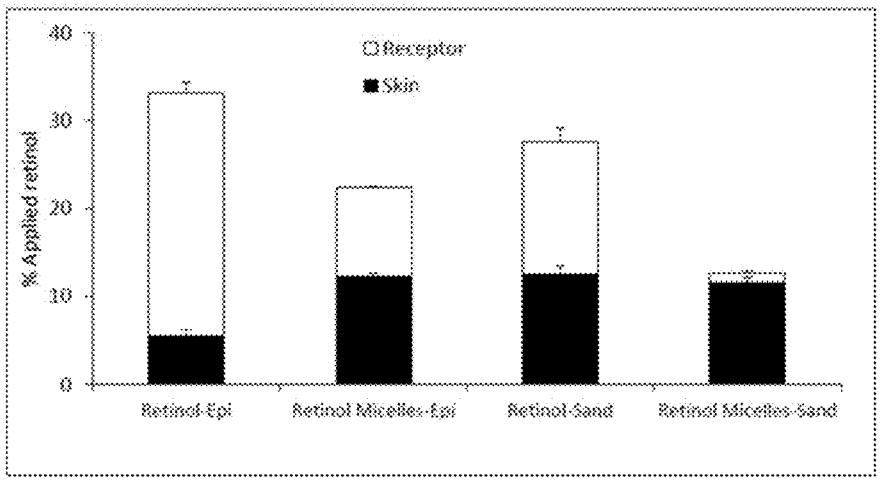

FIG. 48 illustrates the percentage of applied retinol at the end of 48 hours in porcine skin and in receptor medium after treatment with free retinol and retinol encapsulated micelles. Excised porcine epidermis (Epi) was placed between the two compartments of a vertical diffusion cell. In the second set of experiments, the stratum corneum was removed from the porcine epidermis and then was physically placed (sandwiched) over the porcine epidermis (Sand) and was used in the study. Free retinol or retinol nanomicelles were applied over the skin and the study was conducted for 48 hours. The receptor medium consisted of phosphate buffer (pH 7.4) maintained at 37° C. and stirred using a magnetic bead. Free or encapsulated retinol dispersion in phosphate buffer (pH 7.4) was loaded in the donor chamber. At the end of the study, the retinol concentration in the skin and receptor compartment was measured by radiochemical method using $^3$H labeled retinol. The skin was digested using 0.1M sodium hydroxide to determine the retinol concentration (mean±SD; n=6).

Figure 49:
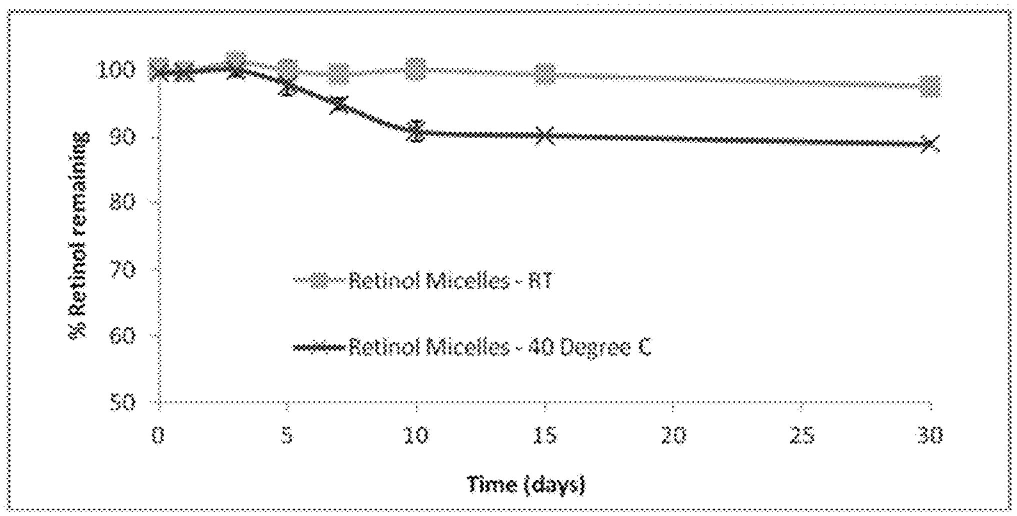

FIG. 49 illustrates the stability of the retinol micelle cream formulation stored at room temperature and 49° C. for a period of one month in glass vials covered with aluminum foil. At regular intervals an aliquot of the formulation was removed and the retinol content was analyzed using HPLC. The formulation remained stable and did not show any significant degradation at room temperature. Each vial is a mean±SD; n=3.

Figure 50:
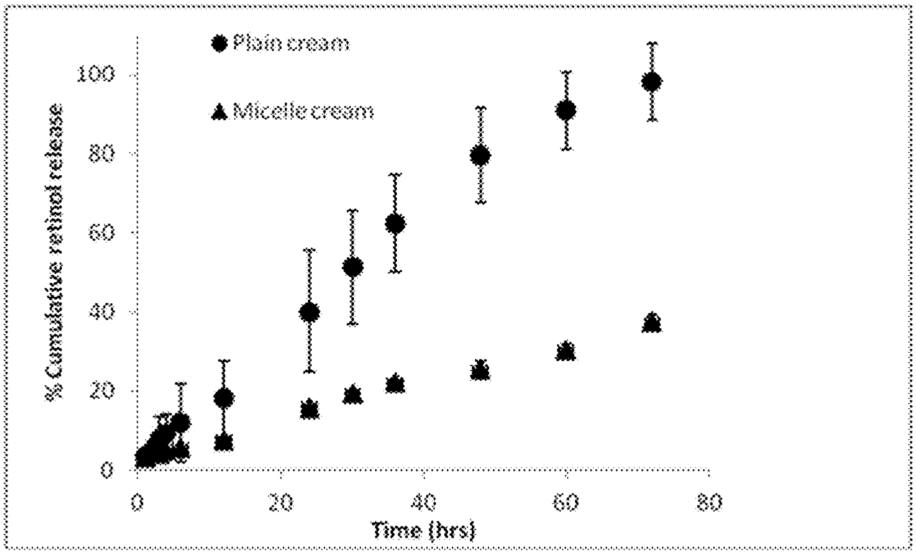

FIG. 50 illustrates in vitro release of free retinol (filled circle) and retinol micelles (filled triangle) from cream formulation at pH 7.4.

Figure 51:
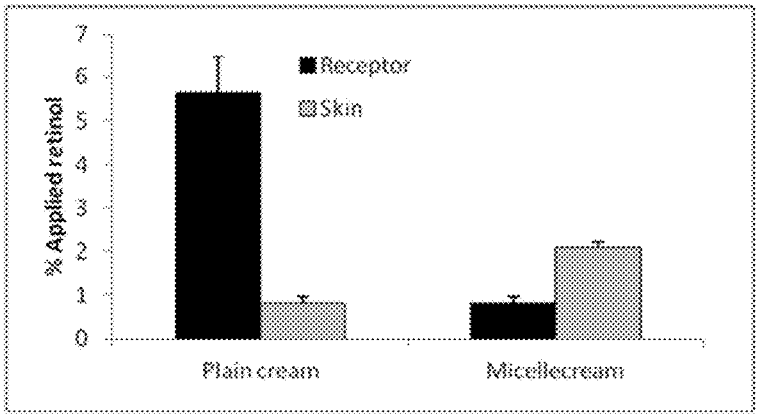

FIG. 51 illustrates the in vitro skin penetration of retinol cream formulations in human skin.

Figure 52:
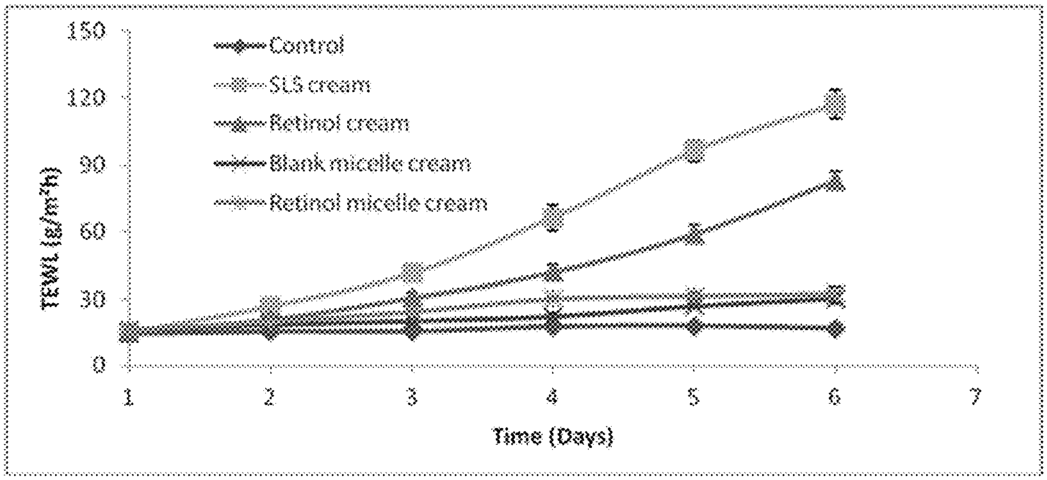

FIG. 52 illustrates the transepidermal water loss (TEWL) values in mice after application of free and micelle encapsulated cream retinol formulations. Sodium lauryl sulfate (SLS), a known skin irritant, was used as the positive control, and the negative control group was not subjected to any treatment.

Figure 53:
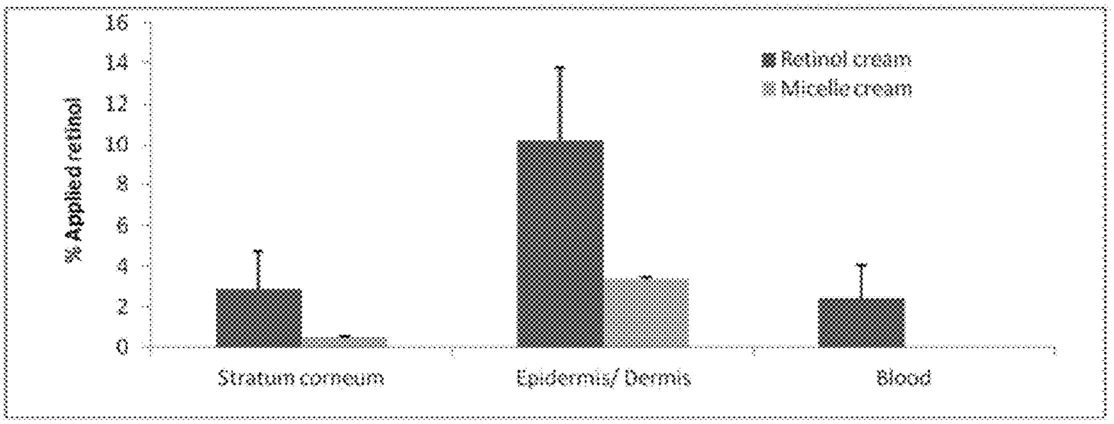

FIG. 53 illustrates the in vivo topical bioavailability of free and nanoparticle encapsulated retinol after treatment for 6 hours in SKH-1 hairless mice.

Figure 54:
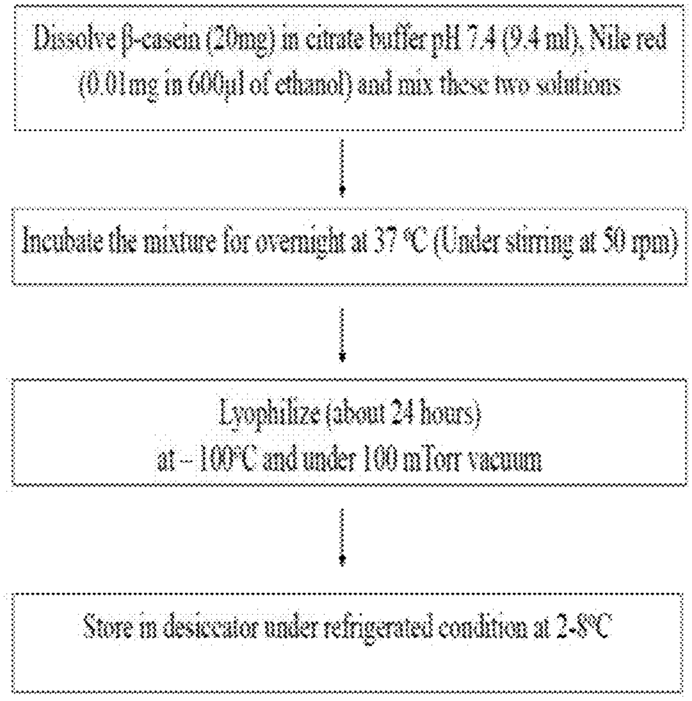

FIG. 54 illustrates the steps to prepare Nile red loaded casein micelles.

Figure 55:
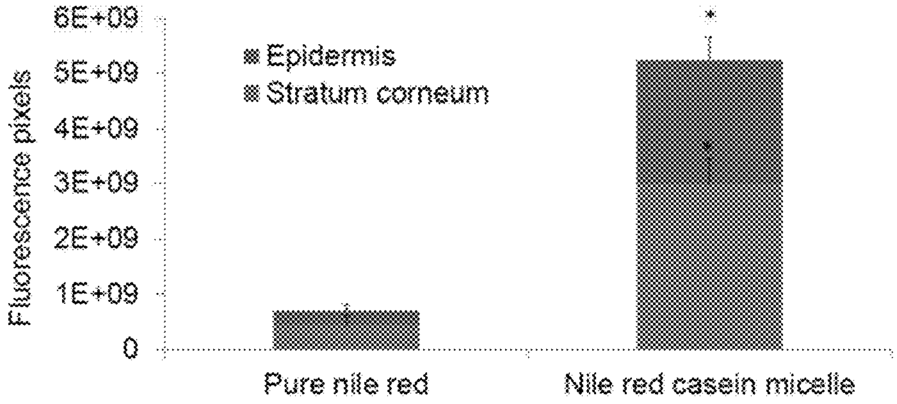

FIG. 55 illustrates the fluorescence pixels in the different layers of the skin after 6 hours of treatment with free Nile red and Nile red encapsulated in casein micelles. For stratum corneum (SC), 0-20 μm and for epidermis 20-100 μm XZ optical sections were used for quantifying the fluorescence pixels.

DETAILED DESCRIPTION OF THE INVENTION

Zein, a hydrophobic plant protein, belongs to a family of prolamines and is water insoluble. Zein has been investigated as a polymer for sustained release of various agents in the pharmaceutical, food, and cosmetic industries (Shukla and Cheryan (2001), Ind Crops Prod 13:171-192). Zein has also been used to film coat materials and to form particulate systems such as microparticles or nanoparticles. Polyethylene glycol (PEG) is a water soluble, biocompatible FDA approved polymer composed of multiple ethylene glycol units linked by ether bonds.

Figure 1:
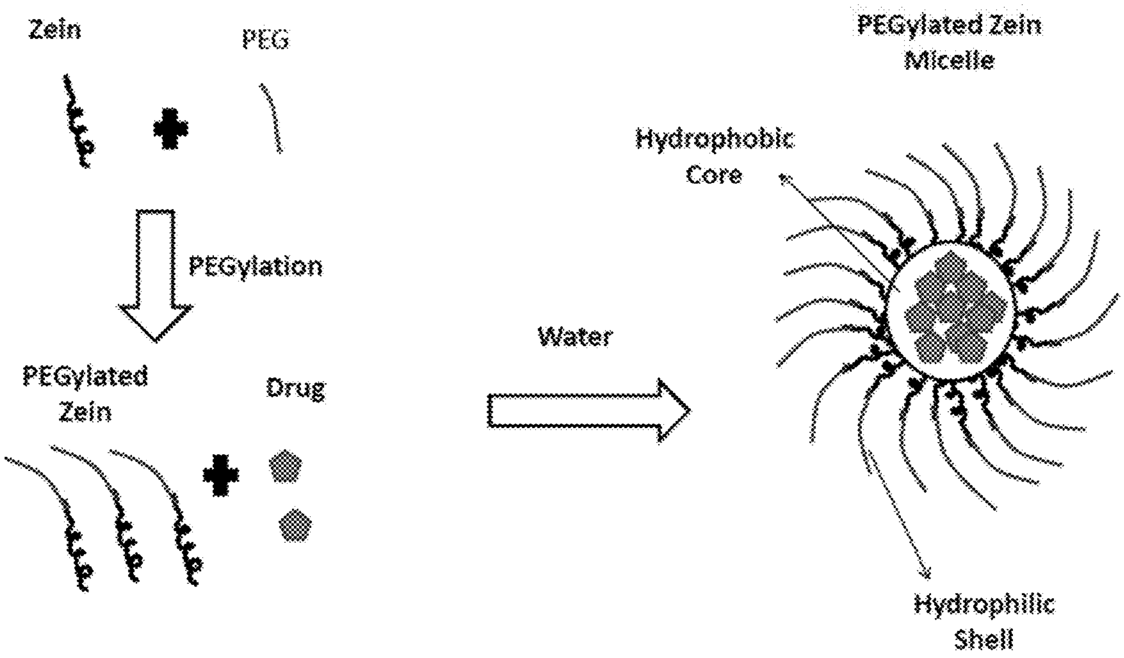
FIG. 1 schematically illustrates the formation of drug loaded PEG-zein nanomicelles, according to an embodiment.

Applicants have discovered that various amphiphilic protein conjugates can self-assemble to form stable, biocompatible, and biodegradable micellar assemblies, as schematically as illustrated in FIG. 1. The micelles can be formed with or without cargo molecules in the micelle core. It was also discovered that zein can be covalently attached to polyethylene glycol (PEG) as described in FIGS. 2 and 3. Blank (non-drug loaded) or drug loaded PEGylated zein self-assembles in an aqueous environment to form nanomicelles (~100 nm) with a hydrophobic core and a hydrophilic shell.

Other hydrophobic proteins can be used in place of zein, for example, those derived from a variety of sources including plants, animals and synthetic sources. Similarly, other water soluble polymers such as polyvinylpyrrolidone, polyglycolic acid, and others described herein can be conjugated to the hydrophobic proteins to prepare the nanomicelles. Various water insoluble hydrophobic molecules (e.g., therapeutic agents or "drugs") can be encapsulated inside the core of the nanomicelle, and the hydrophilic polymeric chains at the corona of the micelle help to solubilize the drug in an aqueous environment, such as the human body. Additionally, charged molecules neutralized with counter ions can be encapsulated inside the hydrophobic core of a micelle described herein. Alternatively, when charged functional groups are introduced into the hydrophobic core or hydrophilic shell, the charged molecules can be complexed to the core and/or to the shell through hydrostatic interactions. For example, attachment of cationic polymers, such as polyethylene imine, polylysine, and the like, to the micelle core and/or shell can be used to complex negatively charged DNA or oligonucleotides. Similarly, hydrophilic molecules can be chemically modified (e.g., into the form of a prodrug or salt) to provide a hydrophobic entity for encapsulation in the core of a micelle. In embodiments, the overall charge on the protein may changed by adjusting pH above or below the pI of the prolamine (e.g., pI of zein is between about 5 and 9; pI of gliadin is about 6.8)

Definitions:

As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The terms "comprising," "including," "having," "containing," "characterized by," and grammatical equivalents thereof, are inclusive or open-ended terms that do not exclude additional, unrecited elements or method steps, but also include the more restrictive terms "consisting of and" consisting essentially of.

The singular forms "a," "an," and "the" include plural reference unless the context clearly dictates otherwise. Thus, for example, a reference to "a compound" (e.g., a drug) includes a plurality of such compounds, so that a compound X includes a plurality of compounds X. As an additional example, reference to "a micelle" can include a plurality of such micelles, and reference to a "molecule" is a reference to a plurality of molecules, and equivalents thereof. It is further noted that the claims may be drafted to exclude any optional element. As such, this statement is intended to serve as antecedent basis for the use of exclusive terminology, such as "solely", "only", and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation off 5%, ±10%, ±20%, or ±25% of the value specified. For example, "about 50" percent can in some embodiments carry a variation from 45 to 55 percent. For integer ranges, the term "about" can include one or two integers greater than and/or less than a recited integer. Unless otherwise indicated herein, the term "about" is intended to include values, e.g., weight percents, proximate to the recited range that are equivalent in terms of the functionality of the individual ingredient, the composition, or the embodiment. In addition, unless indicated otherwise herein, a recited range (e.g., weight percents or carbon groups) includes each specific value or identity within the range.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible subranges and combinations of subranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc.

As will also be understood by one skilled in the art, all language such as "up to," "at least," "greater than," "less than," "more than," "or more," and the like, include the number recited and such terms refer to ranges that can be subsequently broken down into subranges as discussed above. In the same manner, all ratios recited herein also include all subratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "zein" refers to a class of prolamine protein. Prolamines are found in various grains such as corn, wheat, barley, rice, and sorghum, as well as in other plants and animals. Other examples of prolamines include gliadin, hordein and kafirin. These prolamines can be exchanged for zein in the various embodiments described herein. Zein is composed of a high proportion of non-polar amino acids, such as proline, glutamine and asparagine, and has a molecular weight of about 22-27 kDa (Shukla, Zein: the industrial protein from corn. Ind. Crops. Prod. 13, 171-92; 2001). A typical sample of zein can have approximately 20% leucine, 10% proline, 21-26% glutamine, 5% asparagine, and 10% alanine, therefore at least about 61% of its amino acid composition is of hydrophobic amino acids. These hydrophobic amino acids render the protein water insoluble. Zein is a biodegradable US-FDA approved GRAS polymer (Fed. Register (1985) 50:8997-8999).

Zein can be manufactured as a powder from corn gluten meal. Pure zein is odorless, tasteless, water-insoluble, and edible, properties which have rendered it an important component for processed foods and pharmaceuticals. Methods for isolating, processing, and using zein are well known in the art. See for example, Lawton, Cereal Chem 2002, 79(1): 1-18, and WO 2009/137112 (Perumal et al.), which are incorporated herein by reference. A "grade" of zein refers to a variety of types or forms of zein, including white zein and yellow zein, derived by various means, such as is disclosed in U.S. Pat. No. 5,254,673 (Cook et al.), the contents of which are incorporated by reference herein.

The term "PEG" or "polyethylene glycol" refers to a water soluble, biocompatible FDA approved polymer composed of multiple ethylene glycol units linked by an ether bond. The molecular weight of a PEG chain or moiety can vary from about 1 kDa to about 220 kDa, for example, about 1 kDa to about 15 kDa, depending on the number of ethylene glycol units in the chain. PEG moieties can be represented as $—(OCH_2CH_2)_nOH$ or $—(OCH_2CH_2)_nOR$ groups where n is 2 to about 1,000 and R is alkyl, aryl, or arylalkyl such as methyl, ethyl, t-butyl, phenyl, or benzyl. PEG moieties can be attached to proteins through the terminal hydroxyl group, for example, when activated with succinate esters.

In various embodiments, the molecular weight of the PEG chain can be about 1 kDa to about 220 kDa. In certain embodiments, the PEG group can have a molecular weight of about 1,000 to about 20,000, about 4,500 to about 20,000; about 5,000 to about 18,000; about 5,000 to 20 about 12,000; or about 4,000 to about 9,000. In other embodiments, the PEG groups can have a molecular weight of about 4,000, 5,000, 6,000 or about 7,000. The PEG group can also be capped at its terminal end with a protecting group, such as an acetyl group or an alkyl group, for example, a methyl or an ethyl group.

Heterobifunctional PEG groups, which have dissimilar terminal groups, can also be used for PEGylation. Examples of heterobifunctional PEG groups include $HO_2C$-PEG-OH; HC(═O)—PEG-SH, and the like. In addition to linear PEG moieties, branched moieties that include PEG chains can also be used for PEGylation of a prolamine. Examples of various PEG moieties that can be conjugated to zein are described by Roberts et al. (Adv. Drug Deliv. Rev. 54:459-476, 2002) and are illustrated below.

Branched PEG groups based on PEG2 triazine:

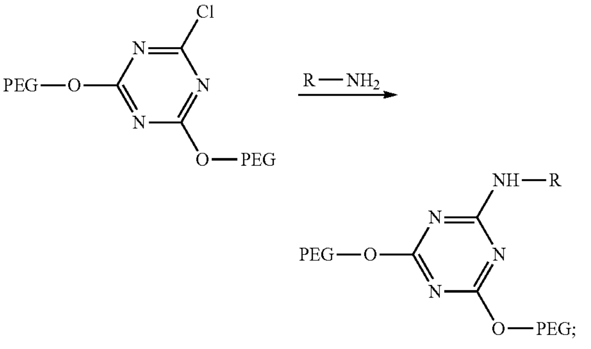

where the amino group of R—NH2 is an amino group on a side chain or terminal group of a prolamine protein. Other PEG moieties that can be conjugated to a prolamine protein include:

1) Branched PEG (PEG2);

2) linear forked PEG; and/or 3) branched forked PEG:

1)

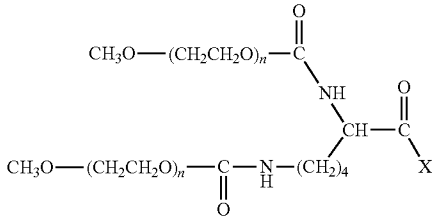

2)

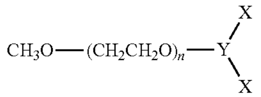

3)

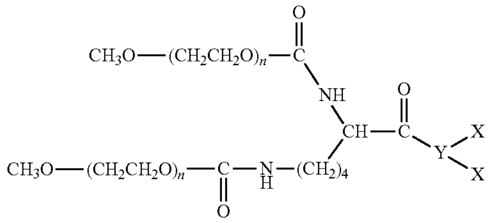

where Y is a group having a carbon branching moiety and X is an atom of a prolamine protein, a linker to a prolamine protein, or a functional group of a prolamine protein.

Polyethylene glycol moieties or other poly(alkylene oxides) can be conjugated to zein by a variety of techniques well known in the art (see for example, Francesco et al. (2005), Drug Discov Today 10, 1451-1458). One example of conjugate formation includes reacting a prolamine protein such as zein with an activated monoalkoxylated PEG ester, such as methoxy PEG-succinimidyl succinate, to form ester or amide linkages, as illustrated in Scheme A below.

Scheme A. PEGylation of (a glutamine side chain of) zein

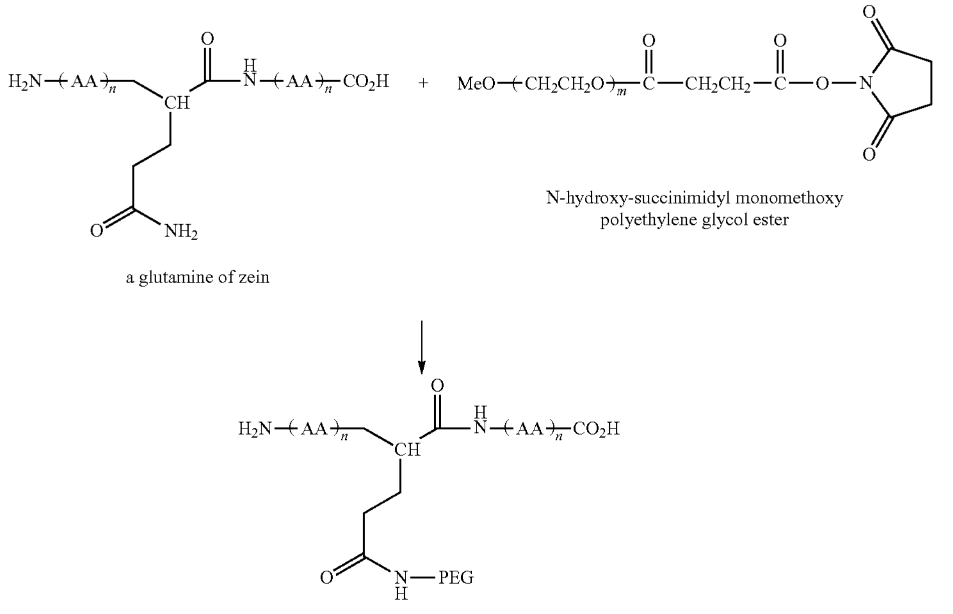

a glutamine of zein

N-hydroxy-succinimidyl monomethoxy polyethylene glycol ester

PEGylated zein

As shown in Scheme A above, m-PEG-N-hydroxy succinimidyl ester can be conjugated through formation of an amide bond to one or more terminal amine groups of glutamine residues (and/or asparagine residues) in a prolamine, such as zein (Sessa et al., (2007) J Appl Poly Sci 105, 2877-2883). In other embodiments, the amine groups in arginine and histidine can be conjugated to PEG through an amide or carbamate linkage. In addition, the N-terminus amino acids can be PEGylated. Various PEG derivatives known in the art can be used for PEGylating the amine groups, including PEG caryboxylic acids, esters, carbonates, aldehydes, and the like. Carboxylic acids in aspartic acid and glutamic acid, as well as the C-terminal carboxylic acids in zein, can also be conjugated to PEG using PEG with amine, hydroxyl, or other functional groups known in the art for linking carboxylic acids to PEG groups. The thiol in cysteine in zein can also be conjugated to PEG using, for example, PEG functionalized with pydriyl sulfide, vinyl sulfone, maleimide, or iodoacetamide. Threonine and serine in zein can also be PEGylated, using techniques well known in the art.

Site specific PEGylation in zein can be achieved using enzymes. For example, transglutaminase can be used to selectively PEGylate the side chain amine group in glutamine as shown in Scheme B below. Similarly selective PEGylation can be achieved by selective glycosylation of hydroxyl group in serine or threonine using acetylgalactosylamine transferase followed by conjugation of PEG-sialic acid using sialyltransferase (Veronese et al. (2005), Drug Discov Today 10, 1451-1458).

Scheme B. Enzymatic PEGylation.

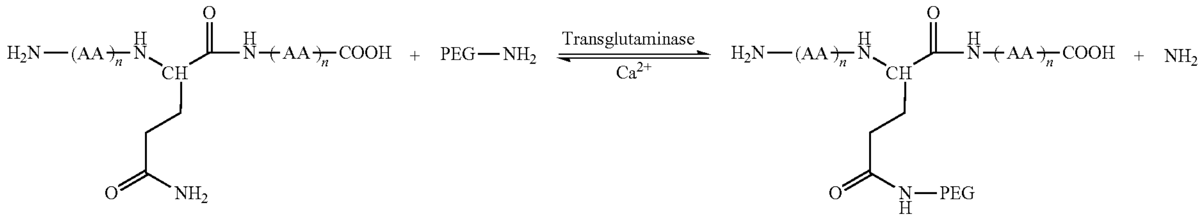

Glutamine of protein

Glutamine PEGylated protein

In various embodiments, other alkylene oxides can be used in place of polyethylene glycol, such as alkylene oxide chains that contain from 2 to 4 carbon atoms in each alkylene group. Alkoxy-terminated poly(alkylene oxides) are suitable examples, such as methoxy-terminated poly (alkylene oxides), and the free hydroxy end can then be activated with groups such as succinimidyl succinates. In some embodiments, the poly(alkylene oxide) chains can have from about 2 to about 110 repeating units, and typically have from about 50 to about 110 repeating units.

The term "biocompatible" means that the polymer or conjugate referred to does not cause or elicit significant adverse effects when administered in vivo to a subject. Examples of possible adverse effects include, but are not limited to, excessive inflammation and/or an excessive or adverse immune response, as well as toxicity. Zein and polyethylene glycol are biocompatible components.

The term "hydroalcoholic solvent" refers to a solvent system that includes both water and an alcoholic solvent, such as methanol, ethanol, n-propanol, iso-propanol, or butanol (including 1-butanol, 2-butanol (sec-butanol), iso-butanol, and tert-butanol). Common hydroalcoholic solvent systems include 50%, 70%, 90%, and 92% ethanol in water.

The term "stable" refers to a core of a micelle where the core has no contact with water (see, e.g., Core-Shell structure of PEG-Zein, Example 1).

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The term "administered" or "administration" when used in the context of therapeutic and diagnostic uses for micelles, refers to and includes the introduction of a selected amount of micelles into an in vivo or in vitro environment for the purpose of, for example, delivering a therapeutic agent to a targeted site.

An "effective amount" refers to an amount effective to treat a disease, disorder, and/or condition, or to bring about a recited effect. For example, an amount effective can be an amount effective to reduce the progression or severity of the condition or symptoms being treated. Determination of a therapeutically effective amount is well within the capacity of persons skilled in the art. The term "effective amount" is intended to include an amount of a blank or drug loaded micelle described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" can include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can includes both medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "in vivo" means of or within the body of a subject, such as that of a patient, and includes administration of micelles by a variety of means including, but not limited to, oral, buccal, intravenous, intramuscular, intraperitoneal, parenteral, subcutaneous, topical, ocular, pulmonary and nasal routes of administration.

The term "in vitro" refers to environments outside of the body of a subject or patient. The terms "subject" or "patient" both refer to an individual complex organism, e.g., a human or non-human animal.

The term "therapeutic agent," and similar terms referring to a therapeutic or medicinal function mean that the referenced small molecule, macromolecule, protein, nucleic acid, growth factor, hormone, drug, other substance, cell, or combination thereof can beneficially affect the initiation, course, and/or one or more symptoms of a disease or condition in a subject, and may be used in conjunction with micelles in the manufacture of medicaments for treating a disease or other condition. Suitable therapeutic agents for encapsulation in the micelles described herein include hydrophobic therapeutic agents, for example, but not limited to, curcumin, doxorubicin, and imaging agents such as Nile red.

Hydrophobic Agents:

Practically any hydrophobic agent otherwise suitable for the practice of this invention may be employed for a variety of applications. The amphiphilic polymers described herein may also be used as thickening agents, lubricants, detergents, surfactants, and anti-fouling agents. The amphiphilic polymers may be used as an emulsifying, dispersing or stabilizing agent for dyes, cosmetics, pigment and pharmaceutical products. The amphiphilic polymers can be particularly useful as an emulsifying, dispersing or stabilizing agent in the dyeing of textiles and for encapsulating dyes for cosmetics. The amphiphilic polymers can be useful as lubricants and encapsulants for cosmetics, pharmaceuticals, nutraceuticals, pesticides, textiles, and perfumes.

Thus, in addition to biologically or pharmaceutically active hydrophobic agents, other hydrophobic molecules that may be encapsulated by the amphiphilic polymers described herein include diagnostic agents, insecticides, pesticides, herbicides, antiseptics, food additives, fragrances, dyes, diagnostic aids, and the like. Examples of hydrophobic molecules that can be encapsulated by the amphiphilic polymers described herein include, but are not limited to: abietic acid, aceglatone, acenaphthene, acenocoumarol, acetohexamide, acetomeroctol, acetoxolone, acetyldigitoxins, acetylene dibromide, acetylene dichloride, acetylsalicylic acid, alantolactone, aldrin, alexitol sodium, allethrin, allylestrenol, allyl sulfide, alprazolam, aluminum bis(acetylsalicylate), ambucetamide, aminochlothenoxazin, aminoglutethimide, amyl chloride, androstenediol, anethole trithone, anilazine, anthralin, Antimycin A, aplasmomycin, arsenoacetic acid, asiaticoside, astemizole, aurodox, aurothioglycanide, 8-azaguanine, azobenzene; baicalein, Balsam Peru, Balsam Tolu, barban, baxtrobin, bendazac, bendazol, bendroflumethiazide, benomyl, benzathine, benzestrol, benzodepa, benzoxiquinone, benzphetamine, benzthiazide, benzyl benzoate, benzyl cinnamate, bibrocathol, bifenox, binapacryl, bioresmethrin, bisabolol, bisacodyl, bis (chlorophenoxy)methane, bismuth iodosubgallate, bismuth subgallate, bismuth tannate, Bisphenol A, bithionol, bornyl, bromoisovalerate, bornyl chloride, bornyl isovalerate, bornyl salicylate, brodifacoum, bromethalin, broxyquinoline, bufexamac, butamirate, butethal, buthiobate, butylated hydroxyanisole, butylated hydroxytoluene; calcium iodostearate, calcium saccharate, calcium stearate, capobenic acid, captan, carbamazepine, carbocloral, carbophenothin, carboquone, carotene, carvacrol, cephaeline, cephalin, chaulmoogric acid, chenodiol, chitin, chlordane, chlorfenac, chlorfenethol, chlorothalonil, chlorotrianisene, chlorprothixene, chlorquinaldol, chromonar, cilostazol, cinchonidine, citral, clinofibrate, clofazimine, clofibrate, cloflucarban, clonitrate, clopidol, clorindione, cloxazolam, coroxon, corticosterone, coumachlor, coumaphos, coumithoate cresyl acetate, crimidine, crufomate, cuprobam, cyamemazine, cyclandelate, cyclarbamate cymarin, cypernethril; dapsone, defosfamide, deltamethrin, deoxycorticocosterone acetate, desoximetasone, dextromoramide, diacetazoto, dialifor, diathymosulfone, decapthon, dichlofluani, dichlorophen, dichlorphenamide, dicofol, dicryl, dicumarol, dienestrol, diethylstilbestrol, difenamizole, dihydrocodeinone enol acetate, dihydroergotamine, dihydromorphine, dihydrotachysterol, dimestrol, dimethisterone, dioxathion, diphenane, N-(1,2-diphenylethyl)nicotinamide, dipyrocetyl, disulfamide, dithianone, doxenitoin, drazoxolon, durapatite, edifenphos, emodin, enfenamic acid, erbon, ergocorninine, erythrityl tetranitrate, erythromycin stearate, estriol, ethaverine, ethisterone, ethyl biscoumacetate, ethylhydrocupreine, ethyl menthane carboxamide, eugenol, euprocin, exalamide; febarbamate, fenalamide, fenbendazole, fenipentol, fenitrothion, fenofibrate, fenquizone, fenthion, feprazone, flilpin, filixic acid, floctafenine, fluanisone, flumequine, fluocortin butyl, fluoxymesterone, fluorothyl, flutazolamn, fumagillin, 5-furfuryl-5-isopropylbarbituric acid, fusafungine, glafenine, glucagon, glutethimide, glybuthiazole, griseofulvin, guaiacol carbonate, guaiacol phosphate, halcinonide, hematoprophyrin, hexachlorophene, hexestrol, hexetidine, hexobarbital, hydrochlorothiazide, hydrocodone, ibuproxam, idebenone, indomethacin, inositol niacinate, iobenzamic acid, iocetamic acid, iodipamide, iomeglamic acid, ipodate, isometheptene, isonoxin, 2-isovalerylindane-1,3-dione; josamycin, 11-ketoprogesterone, laurocapram, 3-O-lauroylpyridoxol diacetate, lidocaine, lindane, linolenic acid, liothyronine, lucensomycin, mancozeb, mandelic acid, isoamyl ester, mazindol, mebendazole, mebhydroline, mebiquine, melarsoprol, melphalan, menadione, menthyl valerate, mephenoxalone, mephentermine, mephenyloin, meprylcaine, mestanolone, mestranol, mesulfen, metergoline, methallatal, methandriol, methaqualone, 3-methylcholanthrene, methylphenidate, 17-methyltestosterone, metipranolol, minaprine, myoral, naftalofos, naftopidil, naphthalene, 2-naphthyl lactate, 2-(2-naphthyloxy) ethanol, naphthyl salicylate, naproxen, nealbarbital, nemadectin, niclosamide, nicoclonate, nicomorphine, nifuroquine, nifuroxazide, nitracrine, nitromersol, nogalamycin, nordazepamn, norethandrolone, norgestrienone; octaverine, oleandrin, oleic acid, oxazepam, oxazolam, oxeladin, oxwthazaine, oxycodone, oxymesterone, oxyphenistan acetate, paraherquamide, parathion, pemoline, pentaerythritol tetranitrate, pentylphenol, perphenazine, phencarbamide, pheniramine, 2-phenyl 6-chlorophenol, phentlmethylbarbituric acid, phenyloin, phosalone, phthalylsulfathiazole, phylloquinone, picadex, pifamine, piketopfen, piprozolin, pirozadil, plafibride, plaunotol, polaprezinc, polythiazide, probenecid, progesterone, promegestone, propanidid, propargite, propham, proquazone, protionamide, pyrimethamine, pyrimithate, pyrvinium pamoate; quercetin, quinbolone, quizalofo-ethyl, rafoxanide, rescinnamine, rociverine, runnel, salen, scarlet red, siccanin, simazine, simetride, sobuzoxane, solan, spironolactone, squalene, stanolone, sucralfate, sulfabenz, sulfaguanole, sulfasalazine, sulfoxide, sulpiride, suxibuzone, talbutal, terguide, testosterone, tetrabromocresol, tetrandrine, thiacetazone, thiocolchicine, thioctic acid, thioquinox, thioridazine, thiram, thymyl N-isoamylcarbamate, tioxidazole, tioxolone, tocopherol, tolciclate, tolnaftate, triclosan, triflusal, triparanol; ursolic acid, valinomycin, veraparnil, vinblastine, vitamin A, vitamin D, vitamin E, xenbucin, xylazine, zaltoprofen, and zearalenone.

A particular class of hydrophobic molecules having biological activity that are suitable for use with the present invention are inter-cellular regulators and mediators such as interferons, growth factors, hormones, and the like, including their cognate receptors. The amphiphilic conjugates described herein are contemplated to be particularly effective for the efficient administration of interferons, which has proven to be problematic because of interferon's water-insolubility. Topical dosage forms of the micellar formulations described herein can exhibit an unexpectedly accelerated rate of transdermal delivery attributable to the encapsulation of the hydrophobic material by the amphiphilic polymer micelles. Thus, the polymer-encapsulated hydrophobic material having biological or pharmaceutical activity may be prepared as topical dosage forms such as lotions, gels, salves, creams, balms, ointments and the like. These compositions may be in the form of aqueous solutions, or in the form of oil-in-water or water-in-oil emulsions. These compositions can be formulated for administration to a patient by a variety of routes, including administration by injection, pulmonary administration, and administration by via oral or nasal routes. These formulations that include the micelles described herein can be otherwise conventional formulations, optionally containing well-known additives, and can be prepared using art-recognized techniques.

Solubilization Technologies:

Numerous approaches have been used to solubilize hydrophobic drugs for improving their delivery to patients. An overview of existing solubilization technologies is illustrated below in Table A. The table shows only a representative list of solubilization technologies used in marketed products and in clinical development.

TABLE A

Various Solubilization Technologies.

| Drug Delivery Technology | Examples of Commercial Products |
|---|---|
| Milling [a]: NANOCRYSTAL ™ Technology (Elan Drug Delivery) | RAPAMUNE ® (Wyeth); EMEND ® (Apreipitant, MK869) (Merck); TRICOR ® (Fenofibrate) (Abott); MEGACE ® ES (Megestrol) (BMS); INVEGA ® SUSTENA ™ (Ortho McNeil Janssen) |
| Modified cyclodextrins [b]: (Cydex Inc.) CAPTISOL ® | GEODON ® (Ziprasidone) (Pfizer); VFEND ® (Voriconozole) (Pfizer); ABILIFY ® (Aripiprazole) (BMS); CORDARONE ® (Amiodarone) (Prism-Arrhythmia) |
| Salts [c] | Amiodipine besylate; Doxorubicin hydrochloride; Clopidogrel bisulphate |
| Surfactant and polymeric micelles [d]: Amphoteric: lecithin Non-ionic: Polysorbates (TWEEN, SPAN); Vitamin E-TPGS; CREMOPHOR ® EL; SOLUTOL ® HS 15; block co-polymers (e.g., PLURONICS ®); Ionic: Sodium lauryl sulfate (SLS); Self-emulsifying lipids (GELUCIRE, others) | TAXOL ®-BMS AQUASOL A ® Parenteral; AQUASOL E ® Drops; GENEXOL-PM - Phase-II clinical trials |
| PEGylation of small molecule drugs [e] | PEG-docetaxel (Nextar Therapeutics) - Phase I clinical trials; PEG-SN38 (Enzon Pharmaceuticals) - Phase I clinical trials; PEG-irinotecan (Nextar Therapeutics) - Phase II clinical trials |

[a] Lipinski (2002), Am. Pharm. Rev. 5: 82-85; Neervannan (2006), Expert Opin Drug Metab Toxicol 2: 715-731.
[b] Miller et al. (2006), J Pharm Sci, 96: 1691-1707; Redenti et al. (2000), J Pharm Sci 89: 1-8; Redenti et al. (2001), J Pharm Sci 90: 979-986.
[c] Yalkowsky et al. (1998), J Pharm Sci 87: 787-796; Portmann and Simmons (1995), J Pharm Biomed Analysis 13, 1189-1193; Johnson et al. (2003), J Pharm Sci 92: 1574-1581.
[d] Torchillin (2007), Pharm Res 24: 1-16; Vries et al. (1996), Drug Dev Ind Pharm, 22: 475-494; Tije et al. (2003), Clin Pharmacokinet 42: 665-685.
[e] Pasut and Veronese (2009), Adv Drug Deliv Rev, 61, 1177-1188; Greenwald et al. (2000), Crit Rev Ther Drug Carrier Syst 17, 101-161; Veronese et al. (2005), Drug Discov Today 10, 1451-1458.

Overview of PEG Conjugates in Clinical Development or Use as Anticancer Agents:

Milling active agents (drugs) provides several advantages, including scalability, low batch variability, and high flexibility in handling large quantities of drugs. Disadvantages of milling active agents are that the process may be applicable to only crystalline drugs, GRAS listed steric/ionic stabilizers may be needed, Ostwald ripening may occur, and prolonged milling may induce the formation of amorphous compositions, leading to instability.

Modified cyclodextrins, such as β-cyclodextrin, is a GRAS and FDA approved excipient. However, the cyclodextrins require a strict correlation between the structure of guest molecule and cavity size. Cyclodextrins can also significantly modify ADME parameters if the corresponding binding constant is too high. Salts of active agents can be used to provide improved aqueous solubility and can in some cases be used to advantageously alter a pharmacokinetic profile. Salts can also increase the melting point of drug for processing. However, formation of salts requires suitable ionizable groups, and a salt of an active agent can be considered a new drug by FDA and require separate approval. Salts can also result in a common ion effect with hydrochloride salts, and have a propensity for formation of hydrates and polymorphs, and/or alter pharmacokinetics.

Surfactant and/or polymeric micelles have less of a tendency to precipitation on dilution, undesirable side effects are minimized, and have been found to be a useful drug delivery system. However, many micelle systems have various amounts of toxicity associated with their component surfactants, loading capacity can be insufficient, and solubilization capacity can be too low. Owing to their surface activity, surfactant molecules also have the potential to penetrate and disrupt biological membranes and can be hemolytic.

The critical micellar concentration (CMC) of micelles dictates their structural stability after in vivo administration, and polymeric micelles have higher structural stability than surfactant micelles. However, most of the polymeric micelles that are reported in the literature are synthetic block copolymers that are prepared from individual monomeric units through tedious and complex synthetic procedures.

PEGylation of small molecule drugs can be limited by the number of functional groups in a drug. PEGylation of small drug molecules can also cause conformational constraint and may affect the binding and therapeutic activity of the drug. Furthermore, due to the limited conjugation of PEG (i.e., one PEG per drug molecule) and limited drug loading with a polymer drug—conjugate, the increase in water solubility of highly hydrophobic drugs is modest at best. Accordingly, improved drug delivery systems are needed to overcome the many disadvantages of currently used drug delivery technologies.

Micelles and Applications Thereof:

The present invention relates to a method of preparing micelles using a hydrophobic water insoluble protein and a water soluble polymer. For example, polyethylene glycol (PEG), a synthetic polymer, can be covalently conjugated to zein, a hydrophobic water insoluble plant protein. Amphiphilic PEGylated zein can spontaneously form self-assembled micelles with a hydrophobic core and a hydrophilic shell when dispersed in water at a CMC of about 0.025 g/L. The diameter of the micelles can be, for example, about 10 nm to about 450 nm, about 10 nm to about 300 nm, about 75 nm to about 450 nm, about 75 nm to about 300 nm, about 10 nm to about 200 nm, or about 80 nm to about 200 nm.

It was found that nanomicelles were formed only after covalent modification of zein with polyethylene glycol of about 3 kDa or larger. PEG moieties of about 5 kDa were found to be especially suitable for micelle formation when conjugated to zein.

Because zein is a high molecular weight protein (approximately 22-27 kDa), the PEGylated zein forms more stable micelles than most other known polymeric micelles. The concentration required for formation of micelles is known as critical micellar concentration (CMC). The CMC determines the stability of a micelle on dilution with water or serum. In this regard, the lower the CMC, the higher the stability of micelles. For example, sodium dodecyl sulfate has a CMC of about 2.304 g/L. The CMC for PEGylated zein, in some embodiments, is 0.025±0.0095 g/L, which is lower than the CMC value for commercially available block-copolymeric micelles prepared from polyethylene oxide and polypropylene oxide (PLURONIC®) polymers, which varies between 0.3 and 190 g/L, depending on the molecular weight of PLURONIC® polymers.

PEG-zein micelles can be combined with other surfactant or polymers to form mixed micellar systems, for example, to enhance encapsulation or stability, or provide additional or varied functionality. Surfactants that can be used to form mixed micelles may include nonionic surfactants such as BRIJ 35, BRIJ 58P, TRITON X-100, TRITON X-114, TWEEN 20, TWEEN 40, TWEEN 80, SPAN 80, and the like, or anionic surfactants such as bile salts, sodium dodecyl sulfate, or cationic surfactants such as hexadecyltrimethyl ammonium bromide (CTAB), trimethyltetradecyl ammonium bromide (TTAB), and the like.

PEG-prolamine graft copolymers or block-co-polymers can be used to form mixed micelles with other polymers that include PLURONICS (polypropylene oxide-b-polyethylene oxide), polylactic acid-b-PEG, polycaprolactone-b-PEG, PEG-b-poly(N-isopropylacrylamide), PEG-b-poly(2-(diethylamino)ethyl methacrylate)-b-poly(-(diethylamino)ethyl methacrylate), PEG-b-polyaminoacids, polyaspartic acid-b-PEG, PEG-b-polypropylene oxide-b-polyethylene oxide, polylactic acid-b-polyethylene oxide-b-polypropylene oxide, polyvinylpyrrolidone-b-polylactic acid-b-polyvinylpyrrolidone, poly((3-benzyl aspartate)-g-PEG, chitosan-g-polycaprolactone-g-PEG, and the like.

Similarly, lipids such as phospholipids, phosphatidylethanol amine, PEG-diacyllipids and the like can also be used to form mixed micelles with the zein-PEG conjugates. Natural polymers such as casein can also be combined to form mixed micelles with PEG-zein. The surfactants, lipids, natural and synthetic polymers described above are only representative examples and the composition of the surfactants, polymers or lipids in the micelles can be altered to form various mixed micelles with PEG-zein.

Encapsulation of poorly soluble compounds into PEGylated zein micelles can be achieved by co-dissolving both components in a hydroalcoholic solvent, such as 90% v/v ethanol, followed by incubation for an amount of time (e.g., overnight) sufficient to allow partitioning of the hydrophobic compound ("cargo molecule") into the hydrophobic zein core. After incubation, the hydroalcoholic solvent can be removed by evaporation to form a thin film. The film can be reconstituted in a buffer to recover the drug loaded micelles.

Encapsulation of poorly soluble compounds into amphiphilic PEG-Zein can also be achieved by co-dissolving both components in a hydroalcoholic solvent (e.g., 90% v/v ethanol), followed by incubation to allow partitioning of hydrophobic compound into hydrophobic zein core. After incubation, the hydroalcoholic solvent can be removed, for example, by extensive dialysis against water. Complete removal of the alcohol results in formation of the drug loaded micelles.

Alternatively, a lyophilization method can also be used to prepare PEG-zein micelles. The poorly soluble compound and PEG-zein can be dissolved in a water/tert-butanol solvent mixture followed by removal of the solvent by lyophilization. The micelles form spontaneously upon reconstitution of the freeze-dried product in an aqueous vehicle or buffer.

PEGylated prolamine micelles have numerous important applications. For example, they can be used to enhance the solubility of hydrophobic compounds of interest to the pharmaceutical and related industries, such as those hydrophobic compounds with a Log P ranging from about 1 to 6.5 (octanol/water) or greater. In some embodiments, an encapsulation efficiency of about 60% to about 95% can be achieved using the micelles described herein. The micelles described herein can provide sustained release of the encapsulated cargo molecules for up to about one week, or up to about two weeks, in an in vitro or in vivo environment.

The CMC, size and encapsulation efficiency of the micelles can also be varied by changing the degree of PEGylation, molecular weight (m.w.) of PEG moiety used, and the ratio of drug to polymer used in preparing the micelles. For example, the CMC can be lowered by using a higher molecular weight PEG. Similarly, the CMC can be reduced by optimizing the number of PEG chains in a PEG-zein conjugate. A lower drug to PEG-zein ratio can also lead to smaller sized micelles. On the other hand, an increase in drug/PEG-zein ratio can increase the encapsulation efficiency and loading efficiency in the micelles. Cross-linking the zein hydrophobic core or PEG shell can also increase the loading efficiency. The cross-linking can also be used to further sustain the release of cargo molecules from the micelles. Additionally, surface conjugation of targeting ligands can be used to specifically target the micelles to specific tissues in the body, for example, cancer tissue.

Anticancer drug loaded PEGylated zein micelles can be prepared by dissolving the anti cancer agent of interest with the dissolved PEGylated zein when preparing the micelles. These drug loaded micelles can significantly improve the cellular uptake of anticancer drugs and is more efficacious than the free drug. The cellular uptake of the anticancer drugs can be determined by measuring the intracellular drug concentration using HPLC analysis. See FIGS. 30 and 31, and their descriptions. The efficacy of the drug loaded micelles compared to the free drug can be evaluated by measuring the cell viability of drug resistant human cancer cells and determining the concentration required to kill 50% of the cells (i.e., determining the $IC_{50}$ value). The drug loaded micelles had a significantly lower $IC_{50}$ than the free drug. See, for example, FIGS. 17, 28, and 29, and their descriptions.

It was also surprisingly discovered that anticancer drugs encapsulated in PEGylated zein micelles are effective against drug resistant cancers. This discovery was found by analysis of drug resistant human cancer cells using Calcein acetoxy methyl ester (Calcein AM), a fluorescent marker that is a substrate for the P-glycoprotein efflux pump. Overexpression of P-gp efflux pump in some cancers leads to drug resistance. The micelles were able to inhibit the P-gp efflux pump and increase the intracellular concentration of Calcein as measured by spectrofluorimetry. See FIG. 32 and its description. Thus, the PEG-zein micelles can inhibit the P-gp efflux pump and enhance the cell uptake of anti-cancer drugs in drug resistant cancers, such as drug resistant strains of breast cancer, ovarian cancer, colon cancer, lung cancer and glioblastoma. The encapsulation of hydrophobic compounds in the core of the micelles also stabilizes labile compounds against degradation from environmental agents, as determined by measuring the drug concentration at different time periods (e.g., up to 12 hours) of a free drug solution or drug loaded micelle dispersion stored at room temperature under light. The drug concentration was measured by UV-visible spectroscopy.

Additionally, PEGylated zein micelles can be used to develop water soluble/water dispersible formulations of hydrophobic drugs. Because the micelles are small in size (e.g., about 100 nm to about 300 nm in diameter), they can be used for IV administration of, for example, hydrophobic drugs. They can also be used to improve the bioavailability of water insoluble drugs by parenteral, oral, nasal, transdermal, ocular and other routes of drug administration. Lyophilized drug (water insoluble drug) loaded micelle can be readily diluted with water before injection. The lyophilized drug loaded micelle can then be incorporated in a capsule or other suitable formulation matrix. After administration the micelles can form in the gastrointestinal intestinal fluids, resulting in enhanced solubility and absorption of water insoluble drugs. Furthermore, the PEGylated-zein micelles are biocompatible and biodegradable, thereby increasing their safety profile in humans.

In one aspect of the invention, the micelles can be employed as therapeutic and/or diagnostic micelle formulations, e.g., an anticancer agent-containing micelles. Such micelles can provide targeted delivery and temporal control of the release of an active agent, which is often a therapeutic agent such as a small molecular drug, nucleic acid, protein, vaccine, receptors, hormones, cells, antibody, chemical or other agent or substance. In addition to the therapeutic methods described, the invention provides means for producing micelles with diagnostic agents, such as dyes, imaging agents, probes, and the like.

Further modifications to the prolamine-polymer conjugates can be made for specific applications, such as attaching targeting ligands to the hydrophilic shell for targeted delivery to tumors. For example, folic acid, antibodies, and the like can be attached to the PEG shell for targeting cancer cells that overexpress receptors for specific targeting ligands.

Zein micelles formed using the methods described herein may have other uses, particularly outside of the body. For example, drug-loaded PEGylated zein micelles can be used as a coating material for cardiovascular and other biomedical devices. Although described herein with respect to drug delivery, micelles may also be used to encapsulate and sustain the release of molecules of interest to the food, dairy and cosmetic industries. In addition to human drugs, veterinary drugs may also be encapsulated in the micelles. PEGylated zein micelles may be used to protect molecules from degradation, such as by hydrolysis, oxidation, photo-degradation, and other degradation reactions. This utilization may include molecules of interest to the pharmaceutical, food, dairy, agricultural, nutraceutical and cosmetic industries.

Variations of Formula I:

Formulas I-V can be further modified to provide additional embodiments. In any embodiment that recites zein as an example, another type of prolamine can be substituted for zein to provide a separate embodiment. For example, in addition to zein (Z) and PEG, other hydrophobic (X) or hydrophilic polymers (Y) can also be conjugated to any of Formulas I-V to form graft copolymers or ABC type multiblock copolymers, where A, B and C are polymer block moieties of different monomeric units. Examples of these variations include Formulas VI-IX:

Z-b-PEG-b-X (VI)

Z-b-PEG-b-Y (VII)

PEG-b-Z-b-Y (VIII)

PEG-b-Z-b-X (IX)

where X is a hydrophobic polymer moiety, Y is a hydrophilic polymer moiety, and Z and PEG are as defined for Formula I.

The hydrophilic polymer PEG of general Formula I can be replaced with other hydrophilic polymers (Y), such as polyvinyl pyrrolidone (PVP), polyvinyl alcohol (PVA), chitosan, polyethyleneimine (PEI), polyacrylic acid (PAA), polysialic acid (PSA), polysaccharides such as dextran, and the like. Similarly, hydrophobic polymers (X) can be conjugated to prolamines (e.g., zein). Such hydrophobic polymers (X) can include, for example, polycaprolactone, poly lactic acid-co-glycolic acid, polypropylene oxide, polyaspartate, polygultamate, spermine, polylysine, or polyacrylates such as polymethacrylate, polydimethylamino ethyl acrylate, and the like. Fatty acids can also be conjugated to prolamines to form the hydrophobic core. Examples of such fatty acids include, for example, stearic acid, palmitic acid, phosphatidylethanolamine, and oleic acid.

Other and/or additional modifications can be made to the prolamine hydrophobic core and/or to the hydrophilic PEG shell. These modifications can include conjugating stimuli responsive elements, such as polyhydroxyethylmethacrylate, to the core to prepare pH sensitive micelles, or poly (N-isopropylacrylamide) to prepare thermosensitive micelles. In addition, the prolamine hydrophobic core or hydrophilic shell can be cross-linked (for example, using cross-linkers such as glutaraldehyde, genipin, or citric acid, and the like) to control drug release and to increase drug encapsulation and loading efficiency.

Pharmaceutical Formulations of Micelles:

The micelles described herein can be used to prepare therapeutic pharmaceutical compositions. The micelles may be added to the compositions in the form of an aqueous dispersion or as a dry powder of lyophilized micelles. The micelles described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The micelles described herein may be systemically administered in combination with a pharmaceutically acceptable vehicle, such as an inert diluent or an assimilable edible carrier. For oral administration, a micelle dispersion can be enclosed in hard or soft shell gelatin capsules, or lyophilized micelles can be compressed into tablets, or incorporated directly into the food of a patient's/subject's diet. Micelles dispersions or lyophilized micelles may also be combined with one or more excipients and used in the form of ingestible tablets, buccal tablets, troches, capsules, elixirs, suspensions, syrups, wafers, and the like. Such compositions and preparations typically contain at least 0.1 wt % of an active therapeutic or diagnostic agent. The weight percentage of agent in the compositions and preparations can vary and may also conveniently be from about 2% to about 60% of the weight of a given unit dosage form. The amount of active compound in such therapeutically useful compositions containing micelles is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethyleneglycol. Various other materials may be present as coatings or to otherwise modify the physical form of the solid unit dosage form. For instance, tablets, pills, or capsules may be coated with gelatin, wax, shellac or sugar and the like. A syrup or elixir may contain the micelles, in addition to sucrose or fructose as a sweetening agent, methyl and propyl parabens as preservatives, a dye and flavoring such as cherry or orange flavor. Any material used in preparing a unit dosage form should be pharmaceutically acceptable and substantially non-toxic in the amounts employed. In addition, the micelle dispersion or lyophilized micelles may be incorporated into additional sustained-release preparations and devices.

A micelle dispersion may be administered intravenously, subcutaneously, intramuscularly, intratumorally, peritumorally, or by infusion or injection. Dispersions of the micelles can be prepared in water, optionally mixed with a buffer, or in other pharmaceutically acceptable solvents, or mixtures thereof. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the micelles adapted for the extemporaneous preparation of sterile injectable or infusible solutions or dispersions. The ultimate dosage form should be sterile, fluid and stable under the conditions of manufacture and storage. The liquid carrier or vehicle can be a liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the micelles in the required amount in an appropriate solvent with various of the other ingredients enumerated above, as required, followed by filter sterilization. In the case of sterile powders for the preparation of sterile injectable solutions, methods of preparation can include vacuum drying and freeze drying techniques, which yield a powder of the micelles plus any additional desired ingredient present in the previously sterile-filtered solutions.

For topical administration, it will generally be desirable to administer the micelles to the skin as a composition or formulation, for example, in combination with a dermatologically acceptable carrier, which may be a solid, liquid, gel, cream, ointment, or paste. Useful solid carriers include finely divided solids such as talc, clay, microcrystalline cellulose, silica, alumina, and the like. Useful liquid carriers include water, or water-alcohol/glycol/dimethyl sulfoxide (DMSO) blends, in which a micelle can be dispersed at effective levels, optionally with the aid of non-toxic surfactants. Adjuvants such as fragrances and additional antimicrobial agents can be added to optimize the properties for a given use. Fluid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents (e.g., agent loaded micelles) to the skin are known to the art; for example, see U.S. Pat. No. 4,608,392 (Jacquet et al.), U.S. Pat. No. 4,992,478 (Geria), U.S. Pat. No. 4,559,157 (Smith et al.), and U.S. Pat. No. 4,820,508 (Wortzman), herein incorporated by reference in their entireties. Such dermatological compositions can be used in combinations with the micelle formulations described herein.

Useful dosages of drug loaded micelles described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.), herein incorporated by reference in its entirety. The amount of a compound, or an active salt, prodrug, or derivative thereof, loaded into a micelle required for use in treatment will vary not only with the particular compound or salt selected but also with the route of administration, the nature of the condition being treated, and the age and condition of the patient, and will be ultimately at the discretion of an attendant physician or clinician.

The therapeutic agent loaded micelle can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The drug loaded micelles described herein can be effective anti-tumor agents and have higher potency and/or reduced toxicity as compared to non-micelle encapsulated anti-tumor agents. The invention provides therapeutic methods of treating cancer in a mammal, which involve administering to a mammal having cancer an effective amount of a composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kill, and the biological significance of the use of transplantable tumor screens are known.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Preparation of PEGylated Zein and Formation of Micelles

Figure 2:
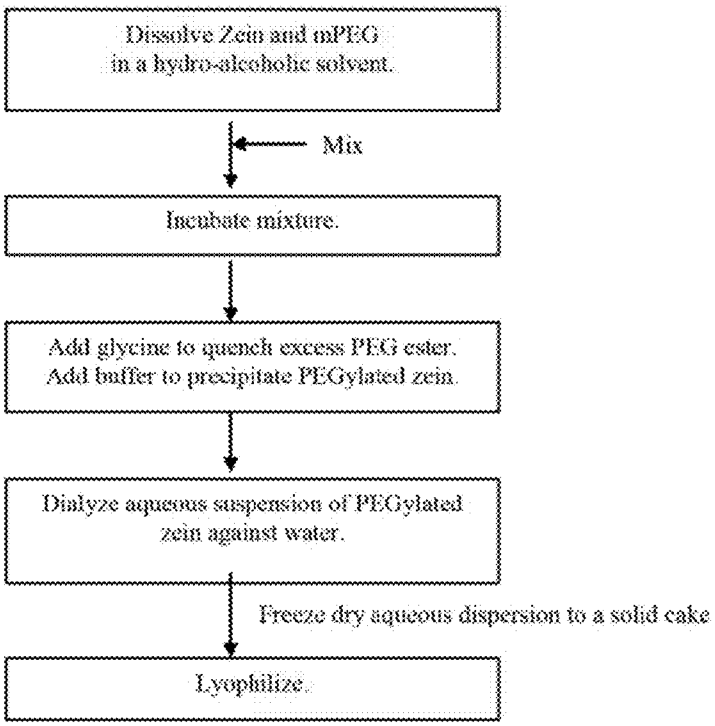
FIG. 2 illustrates a flow chart depicting general steps for preparation of amphiphilic PEG-Zein, according to an embodiment.
Figure 3:
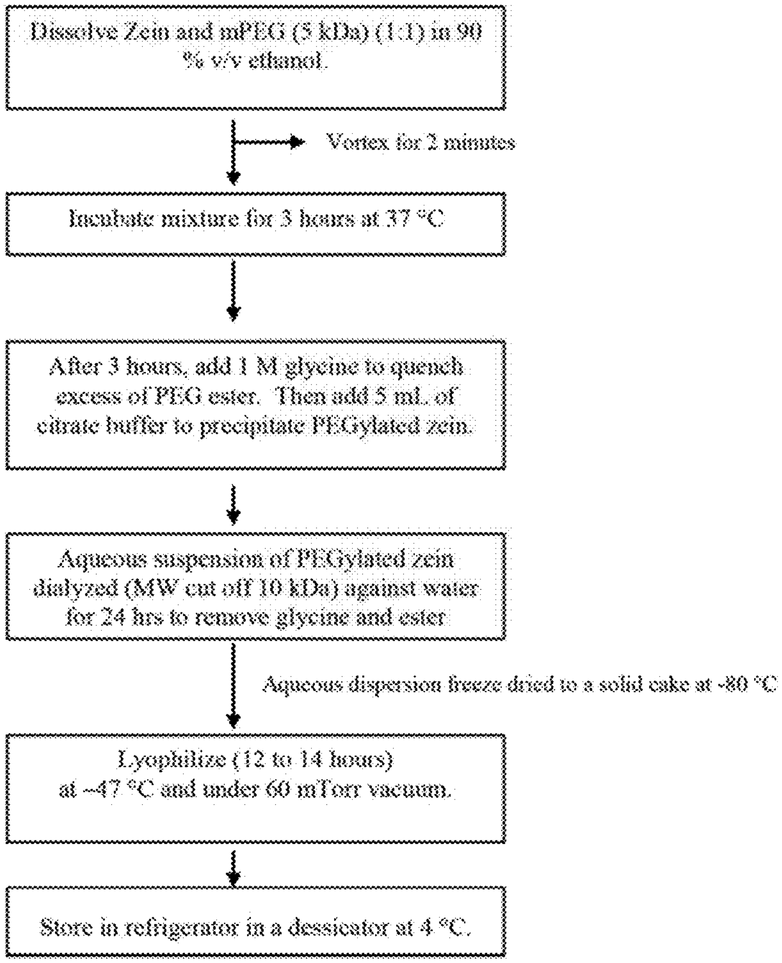
FIG. 3 illustrates a flow chart depicting specific steps for preparation of amphiphilic PEG-Zein, according to one embodiment. The specific amounts recited in this and other figures are for illustration of a particular embodiment, and many variations can be applied to the procedures described herein, as would be readily recognized by one skilled in the art.

PEGylated zein nanomicelles having a size range distribution of between approximately 80 nm and approximately 200 nm were prepared as described herein. FIGS. 2 and 3 illustrate the stepwise preparation of PEG-Zein according to various embodiments. PEGylated zein was prepared by adding 0.1 g of methoxy PEG-succinimidyl succinate (m.w. 1000, 2000, or 5000 Da) to 0.1 g of white zein in 5 mL of 90% ethanol. The mixture in specific ratio (1:1, w/w) was incubated for three hours (stirred at 50 rpm) at 37° C. After 3 hours, 1 mL of aqueous glycine (1 M) solution was added to quench any excess PEG ester. Five mL of citrate buffer, pH 7.4, was then added to precipitate the PEGylated zein. The precipitated dispersion of PEGylated zein was then directly dialyzed (m.w. cut off=~10,000 Da) against deionized water in a magnetic stirrer (100 rpm) at room temperature (~23° C.) for 24 hours to remove free PEG, glycine, and ethanol. The resulting product was frozen to −80° C. followed by freeze drying at −47° C. at 60 mTorr vacuum for 12 to 14 hours.

Figure 4A:
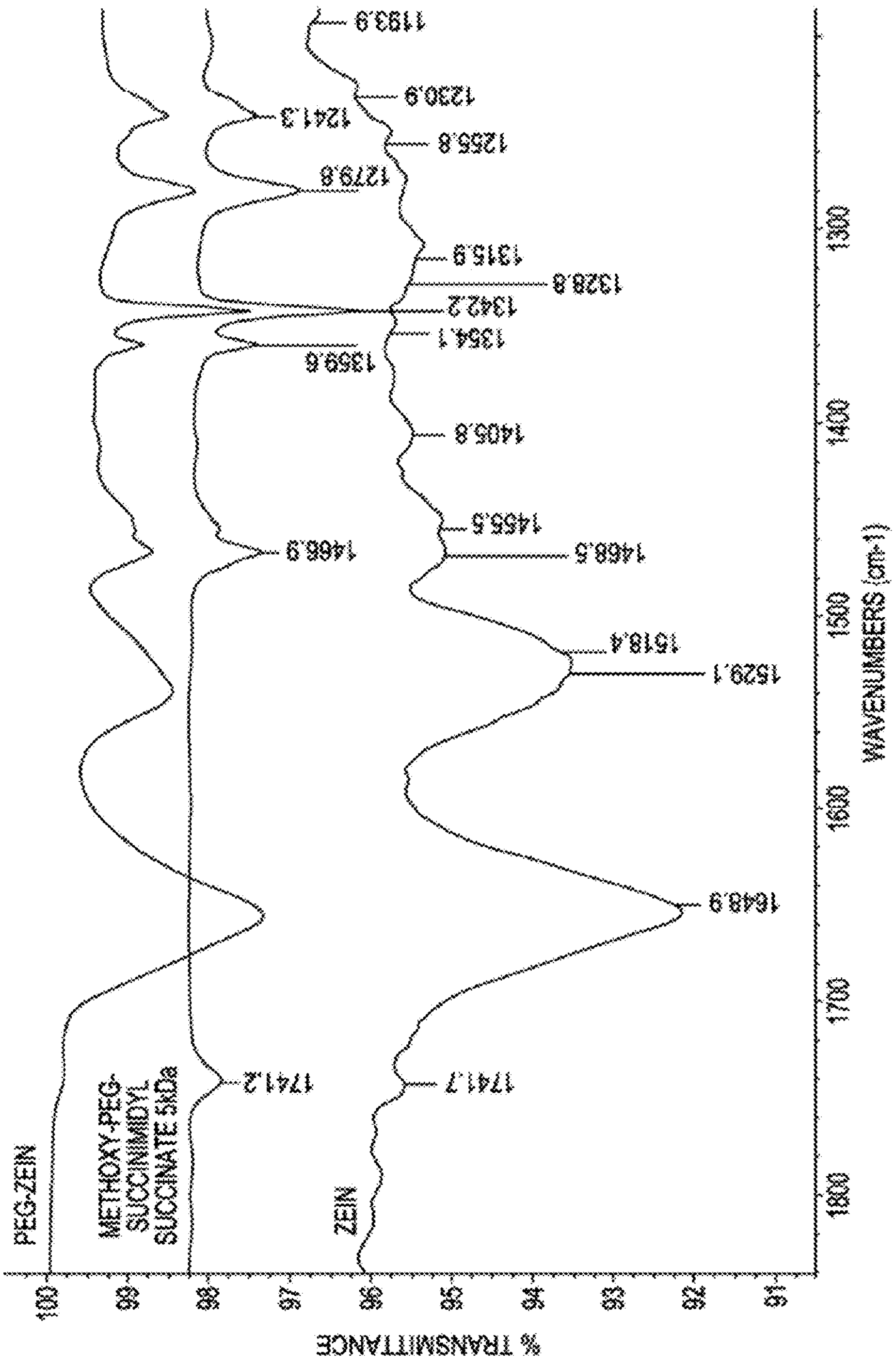
FIG. 4 illustrates characterization of PEG-zein conjugate by (a) FTIR and (b) size exclusion chromatography. FTIR spectrum of zein, PEG-ester, and PEG-zein (5 mg each) were recorded on ZnSe crystal at 2 $cm^{-1}$ resolution in NICOLET 380 ATR-FTIR spectrophotometer (THERMO ELECTRON Corporation, Madison, Wis.). Each spectrum was an average of 100 scans. The peak position of functional groups was analyzed using OMNIC software. SEC was carried out using a PHENOMENEX BISEP SEC-S 2000 4.6 mm×3000 column (PHENOMENEX®, Torrance, Calif.) in a HPLC (BECKMAN COULTER, Brea, Calif.) system. The samples were separated using 70% (v/v) ethanol as mobile phase using a flow rate of 0.5 mL/min. The column eluate was monitored at 280 nm.
Figure 4B:
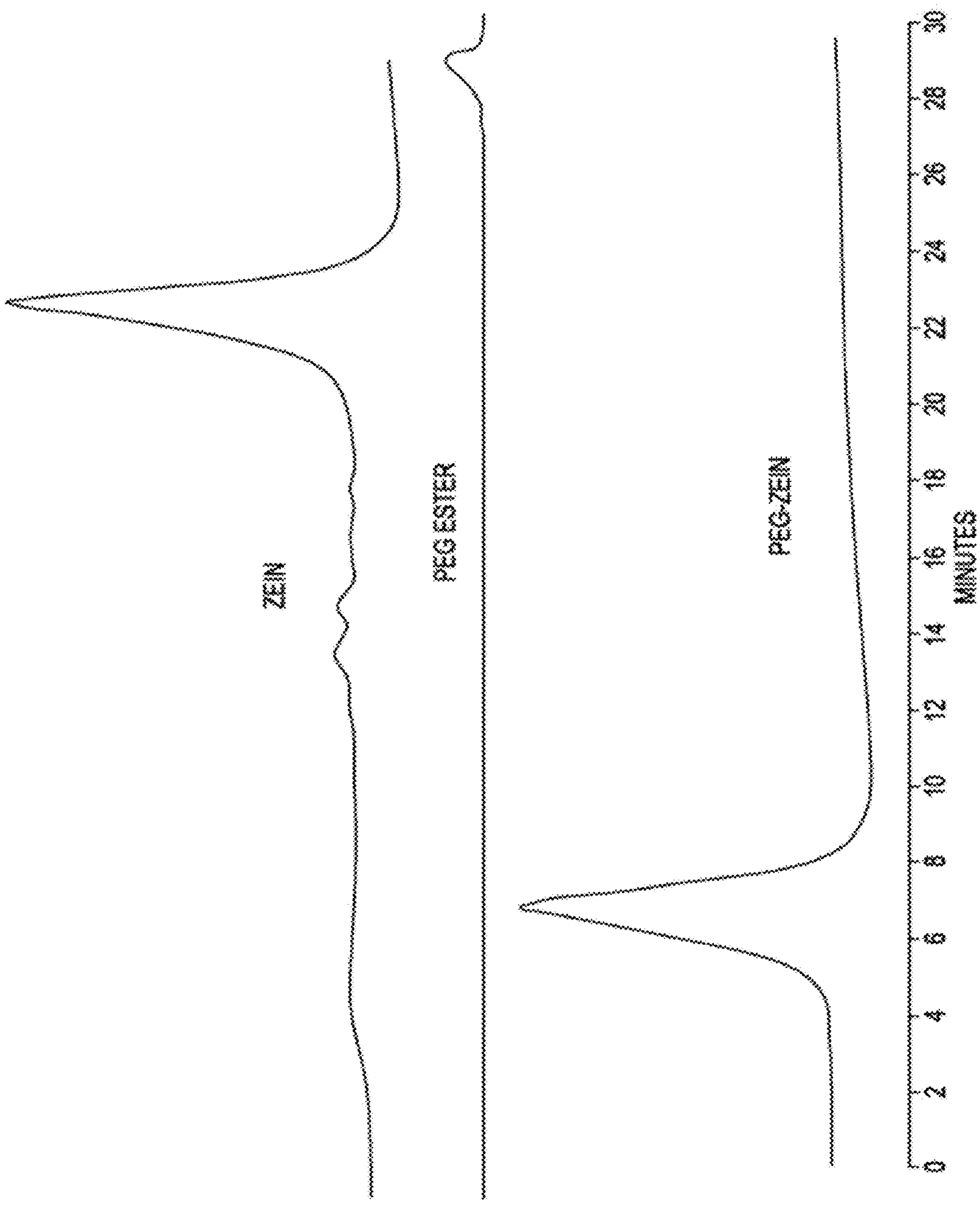

The m-PEG-N-hydroxy succinimidyl ester (5 kDa) was used to form an amide bond with the amino group in zein. The conjugate was confirmed using FTIR. Amide I and II protein peaks of zein are observed in 1650 and 1500-1540 cm$^{-1}$, respectively. The NHS ester peak for PEG is observed in 1740 cm$^{-1}$ which disappeared after conjugation with zein (FIG. 4). Further, the conjugate was characterized by size exclusion chromatograph (SEC). As can be seen in FIG. 4, PEG-zein conjugate eluted at 7 minutes and zein eluted at 23 minutes. On the other hand, PEG eluted at 29 minutes.

The efficiency of PEGylation observed over various molecular weight PEG conjugated zein is shown in Table 1 below, where the efficiency percentages were determined using a trinitrobenzene sulfonic acid (TNBS) assay. The surface amino groups in zein were found to be involved in PEGylation. The TNBS assay was used to estimate the free amino groups in zein before and after PEGylation. A standard curve was generated with increasing concentration of pure zein and PEGylated zein versus absorbance at 440 nm wavelength. PEGylation efficiency was calculated using the formula:

$$\%\ \text{of PEGylation efficiency}=[a-b/a]\times 100$$

where a=slope of the concentration of non-PEGylated zein versus absorbance, and b=slope of the concentration of PEGylated zein versus absorbance. The concentration range of zein used for constructing the standard curve was 0.357 mg/mL to 12 mg/mL, and correlation coefficient was 0.9994.

TABLE 1

| Zein PEGylation Efficiency. | | |
|---|---|---|
| Sample | PEG molecular weight (Da) | PEGylation Efficiency (%) |
| 1 | 1000 | 74 ± 7 |
| 2 | 2000 | 60 ± 4 |
| 3 | 5000 | 52 ± 6 |

Results are representative of triplicate samples (average ± SD).

Smaller sized PEG-Zein micelles were formed using PEG >3000 Da, as illustrated by the data shown in Table 2. The PEGylated zein self-assembles in aqueous environment to form nanomicelles (~100 nm) with a hydrophobic core and a hydrophilic shell, as schematically illustrated in FIG. 1.

TABLE 2

| PEG Molecular Weight Required for Micelle Formation. | | | |
|---|---|---|---|
| Sample | PEG molecular weight (Da) | Particle size (nm) | PDI |
| 1 | 1000 | 970 ± 125 | 0.69 ± 0.12 |
| 2 | 2000 | 902 ± 107 | 0.65 ± 0.08 |
| 3 | 5000 | 95 ± 1.7 | 0.21 ± 0.02 |

Results are representative of triplicate samples (average ± SD).

Figure 5A:
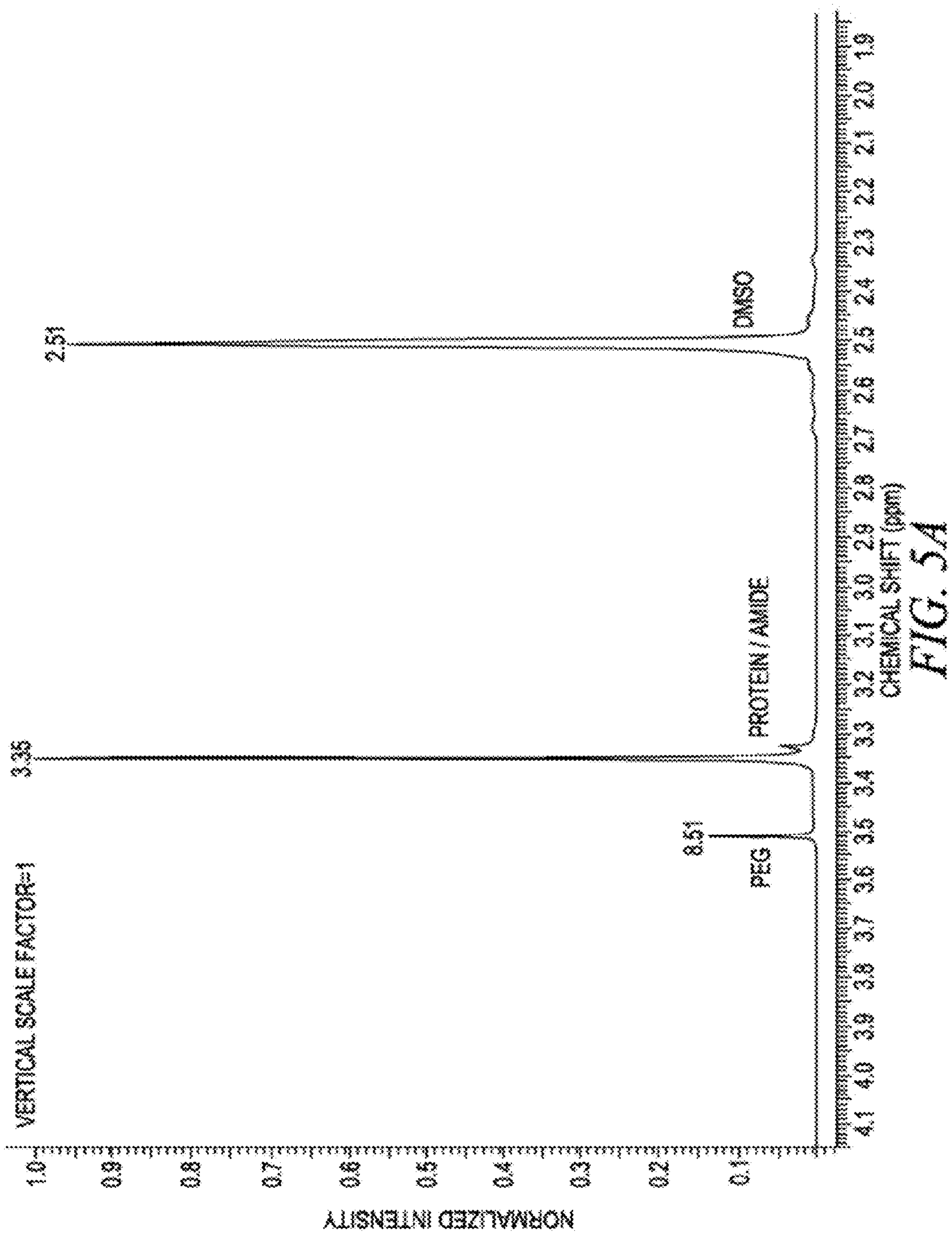
FIG. 5 depicts the $^1$H NMR spectrum of PEG-Zein in (a) DMSO and (b) $D_2O$.
Figure 5B:
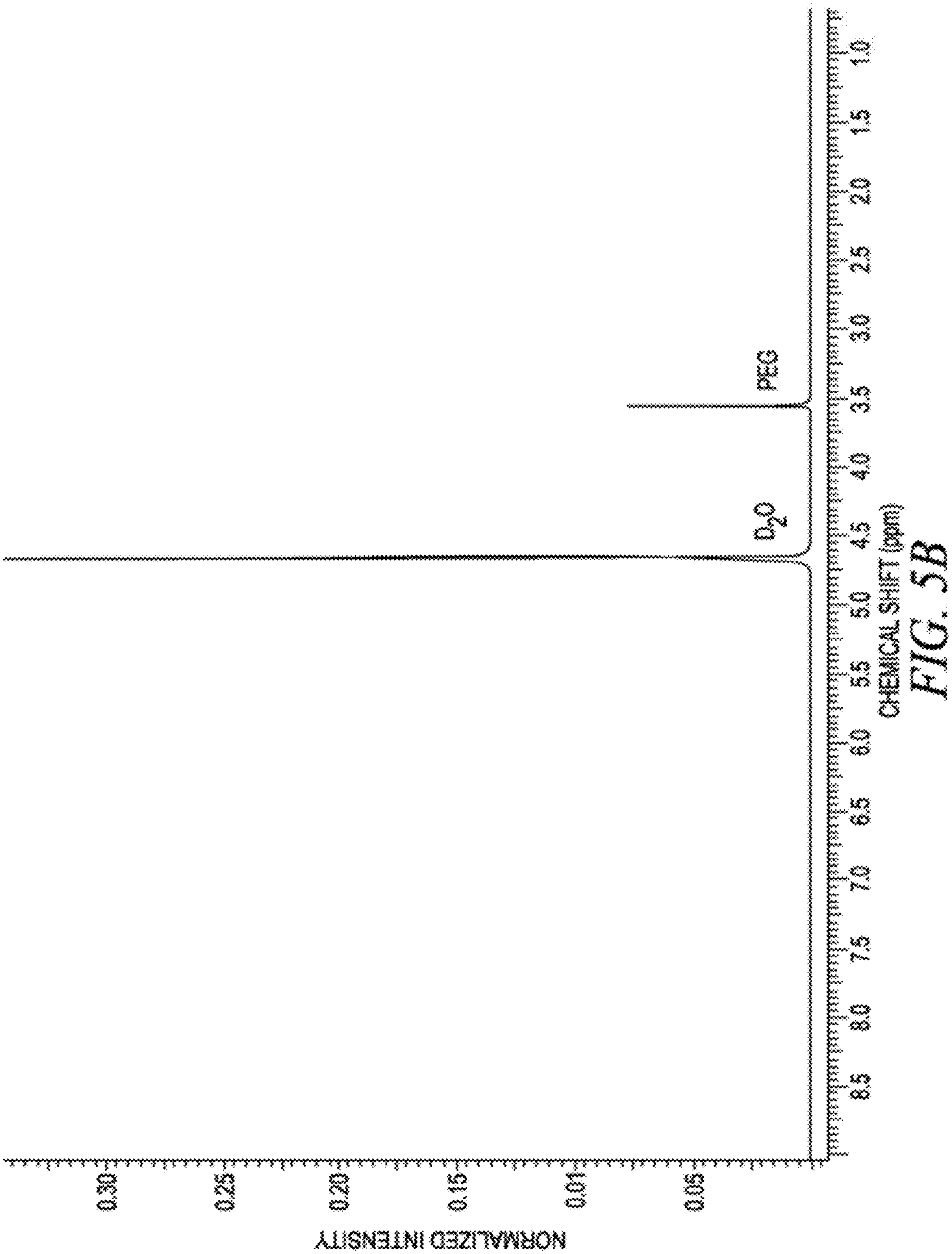

Core-Shell Structure of PEG-Zein: In dimethyl sulfoxide (DMSO), $^1H$ NMR resonance peaks corresponding to hydrophobic and hydrophilic portions of both zein and PEG 5000 Da and are clearly observed in the NMR spectra (FIG. 5): 3.56 ppm for the PEG methylene resonances and 3.36 ppm for the protein/amide resonances. In contrast, only PEG resonance peaks were detected in $D_2O$ and zein peaks were not observed. This result confirms the core-shell structure of PEG-Zein micelles. In deuterated water ($D_2O$), the protein peaks for zein are not observed because the zein is insoluble in water. However, the PEG peak is observed in $D_2O$ because the PEG is water soluble. For the PEG-zein micelle, the shell consisting of PEG blocks is well solvated in $D_2O$ and therefore shows clear NMR spectral peaks, while the resonance peaks of zein, which constitutes the core of the micelles, were not observed due to the lack of the solvent and solvation within the micelle core. DMSO, however, solubilizes and breaks down micelles and thus is able to solvate both PEG and protein, allowing for the peaks corresponding to both portions of the molecules to be recorded (FIG. 5).

Figure 6:
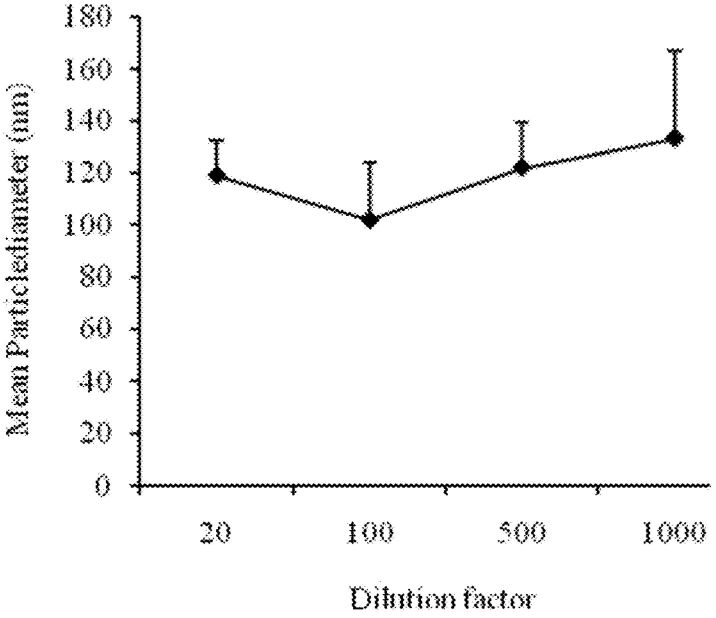
FIG. 6 illustrates the stability of PEG-Zein micelles upon dilution; 2 mg/mL stock dispersion of PEG-zein micelles in 10 mM citrate buffer pH 7.4 was diluted 20, 100, 200, 500, and 1000 times, and the size of the micelles was determined in a particle size analyzer (NICOMP 380 ZLS Zeta Potential Analyzer, Particle Sizing Systems, Santa Barbara, Calif.). The data show that the micelles were stable upon dilution because the size of the micelles did not change significantly. Each data point is a mean of three experiments±SD.
Figure 7:
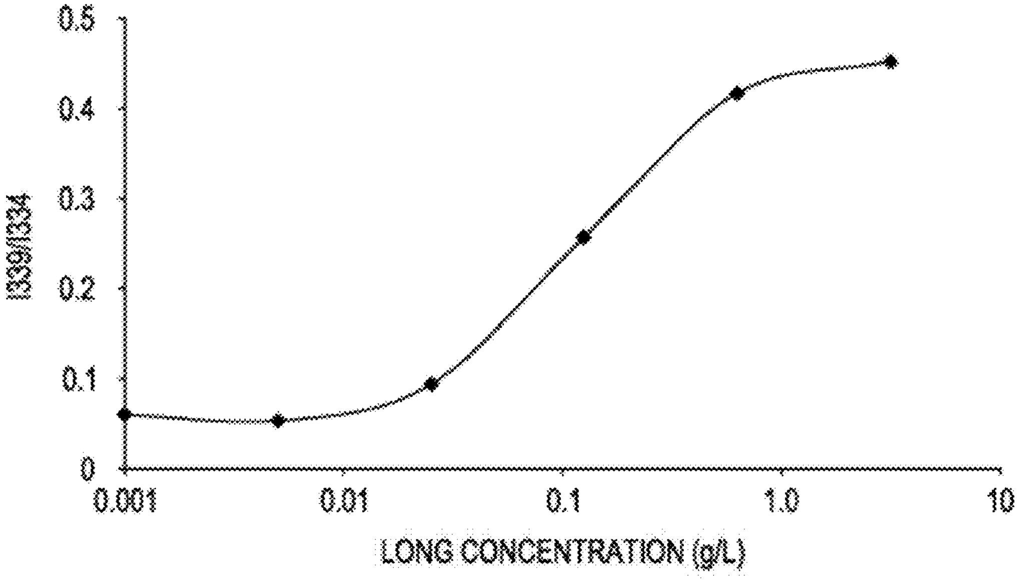
FIG. 7 illustrates the plot of the ratio of absorbance of pyrene (0.6 μM) at the excitation wavelengths of 339 nm and 334 nm (emission wavelength is 390 nm) against logarithmic concentration (g/L) of PEGylated zein. As the concentration of PEGylated zein is increased, the intensity of absorbance of pyrene at the critical micellar concentration (CMC) shifts significantly. The CMC for PEGylated zein is 0.025 (g/L) at 27° C.

The concentration required for formation of micelles is known as the critical micellar concentration (CMC). The CMC value determines the stability of a micelle upon dilution with water. The CMC for PEGylated zein is 0.025±0.0095 g/L, which was determined using pyrene as a probe (FIG. 7). Because the zein molecular weights are relatively high, they form more stable micelles than other polymeric micelles (see, for example, FIG. 6), as indicated by the lower CMC value of zein micelles. FIG. 6 illustrates the plot of the ratio of absorbance of pyrene (0.6 ILIM) at the excitation wavelengths of 339 nm and 334 nm (emission wavelength is 390 nm) against logarithmic concentration (g/L) of PEGylated zein. As the concentration of PEGylated zein is increased, there is a significant shift in the intensity of absorbance of pyrene at the CMC (i.e., concentration at which micelles are formed).

Figure 8:
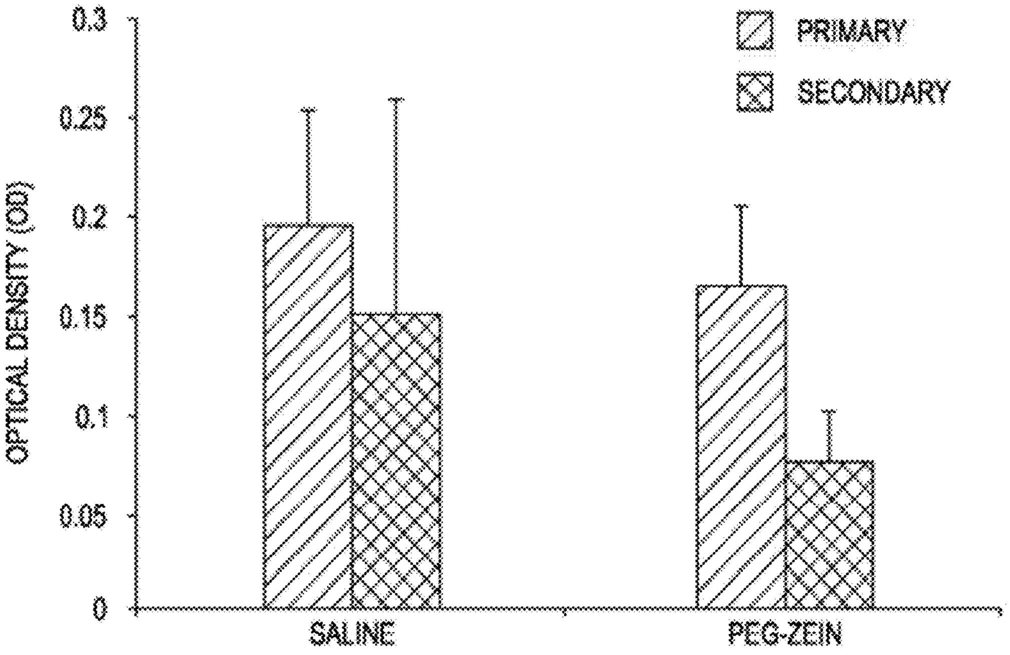
FIG. 8 illustrates the immune response after in vivo administration of PEG-zein micelles in mice. Anti-zein antibodies (optical density in y-axis) in serum was measured after the third week of the first dose and the 5th week after the booster dose. Saline or PEG-Zein micelles (100 μg/50 μL) was administered subcutaneously in mice. The results are represented as mean±standard error of mean (n=4). The PEG-zein micelles did not produce any anti-zein antibodies and the values were similar to the saline control.

The particle size of micelles did not change significantly on dilution with buffer indicating the stability of micelles (FIG. 6). The prepared PEG-zein micelles were non immunogenic as determined by the absence of any zein specific antibodies after subcutaneous administration in mice (FIG. 8). A summary of particle sized and encapsulation efficiencies for various hydrophobic compounds loaded into PEG-zein micelles is shown in Table 3 below.

TABLE 3

| PEG-Zein Micelle Encapsulation Data of Various Compounds. | | | | | | |
|---|---|---|---|---|---|---|
| Sample | Compound | Log P | M.W. (Da) | Particle size (nm) | PDI | Encapsulation Efficiency (%) |
| 1 | Curcumin | 2.5 | 368.3 | 124 ± 4.1 | 0.25 ± 0.03 | 95 ± 4 |
| 2 | Doxorubicin | 1.20 | 543.5 | 153 ± 3 | 0.18 ± 0.06 | 92 ± 6 |
| 3 | Nile red | 5 | 318.3 | 165 ± 7 | 0.21 ± 0.08 | 77 ± 11 |

Results are representative of triplicate samples (average ± SD); PDI = polydispersity index.

Example 2

PEGylated Zein Micelles Encapsulating Doxorubicin

Doxorubicin is a widely used anticancer drugs for the treatment of breast cancer and ovarian cancer, among others. However, the clinical use of doxorubicin is limited by serious side effects, such as myelosupression and chronic cardio toxicity, which can lead to congestive heart failure (Hortobagyi (1997), Drugs 54 Suppl 4:1-7). Another limitation of doxorubicin is the development of resistance to chemotherapy (Gottesman et al. (2002), Nat Rev Cancer 2:48-58). Doxorubicin has a molecular weight (m.w.) of 543.5, a Log P of 1.2, is practically insoluble in water, and is soluble in methanol, ethanol and DMSO.

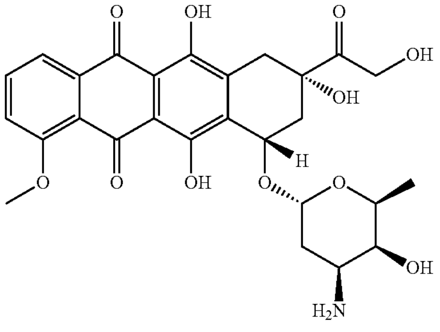

doxorubicin

Compared to low molecular weight surfactant micelles, polymer micelles are generally more stable with a low critical micelle concentration (CMC) and slower dissociation, allowing retention of loaded doxorubicin for longer period of time, and eventually, achieving a higher accumulation of the drug at the target site. Such selective passive targeting capability is due to the enhanced permeability and retention effect, resulting from a leaky vasculature and a lack of lymphatic drainage in tumor tissues (Maeda et al. (2000), J Control Release 65:271-284).

Water insoluble doxorubicin base was extracted from its hydrochloride salt. Doxorubicin hydrochloride (0.012 g) was dissolved in 100 mL of deionized water (0.22 μM filtered), and was stirred magnetically for 10 minutes to allow complete solubilization of doxorubicin. The pH of the solution was 7.2. Triethylamine (0.2 mL) was added followed by magnetic stirring for 30 minutes to allow uniform mixing. The pH of the resulting solution was 12. To this aqueous solution 100 mL of chloroform was added and was stirred magnetically for 15 minutes. The resulting emulsion was shaken vigorously in a separating funnel, and the chloroform layer was recovered. The procedure was repeated three times to recover the base completely. Fractions were combined and concentrated to dryness under reduced pressure (on a rotary evaporator). The dry residue was redissolved in chloroform and was rinsed with a saturated aqueous solution of sodium chloride. The chloroform layer was separated into a round bottom flask and was completely concentrated to dryness on a rotary evaporator. The doxorubicin base in a round bottom flask was kept in an oven (under dark conditions) at 37° C. for 48 hours to allow complete drying. The product was stored at 4° C. until used.

Figure 20:
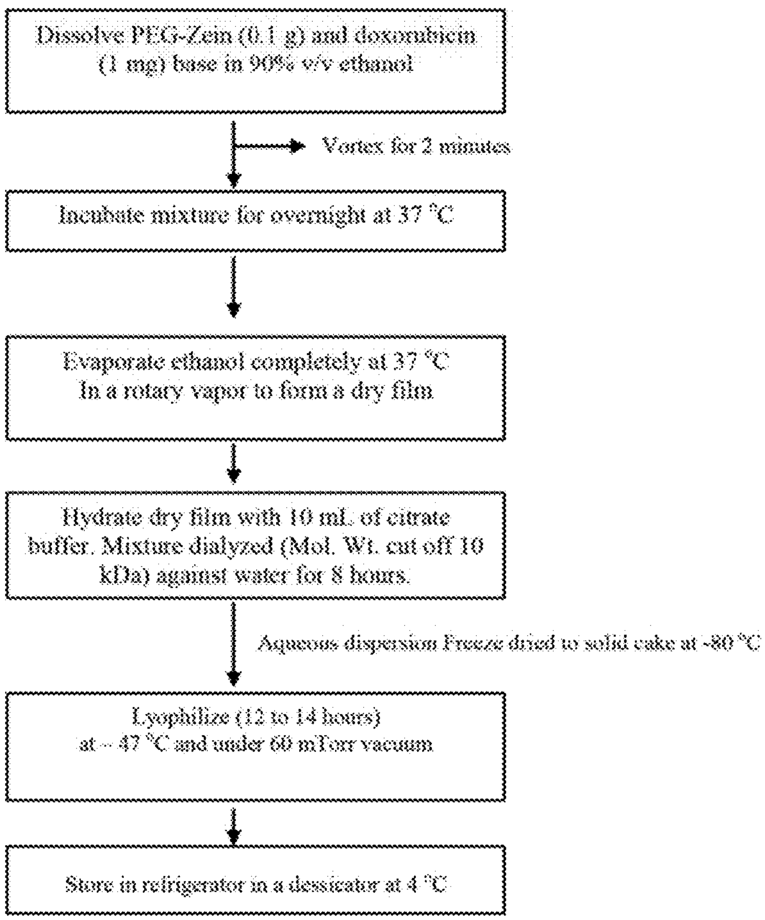
FIG. 20 illustrates steps for the preparation of doxorubicin-loaded PEGylated zein micelles using a film method, according to an embodiment.
Figure 21:
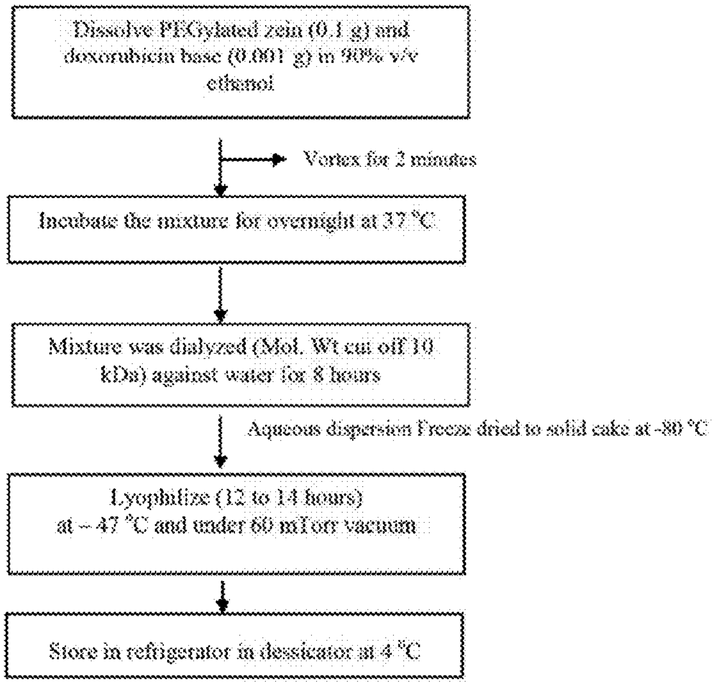
FIG. 21 illustrates steps for the preparation of doxorubicin-loaded PEGylated zein micelles using a dialysis method, according to an embodiment.

FIGS. 20 and 21 illustrate the stepwise preparation of doxorubicin-loaded PEG-Zein micelles using film and dialysis methods, respectively. In both film and dialysis methods, 0.1 g of PEG-Zein and 0.001 g of doxorubicin were dissolved in 20 mL of 90% ethanol. The mixture was incubated overnight (magnetic stir bar, stirred at 50 rpm) at 37° C. to allow partitioning of doxorubicin into the hydrophobic zein core. After overnight incubation, the hydroalcoholic solvent was completely removed under reduced pressure by rotary evaporation to form a thin film. The dried film of doxorubicin-loaded PEG-Zein micelles was reconstituted in a citrate buffer pH 7.4 and sonicated for 5 minutes to form a uniform suspension. The mixture was then dialyzed (m.w. cut off=~10,000 Da) against water in a magnetic stirrer.

For the dialysis method, after overnight incubation, the mixture was dialyzed (m.w. cut off=~10,000 Da) against water in a magnetic stirrer (100 rpm) at room temperature for 24 hours to remove any residual material. The resulting product was then frozen to −80° C. followed by freeze drying at −47° C. at 60 mTorr vacuum for 12 to 14 hours (FIG. 21). The lyophilized product was stored in a dessicator under refrigerated condition at 4° C. Table 4, below, illustrates various characteristics of doxorubicin-loaded PEGylated zein micelles prepared using a film method and a dialysis method, respectively.

TABLE 4

| Sample | Doxorubicin (% w/w) | Particle size (nm) | PDI | Encapsulation Efficiency (%) |
|---|---|---|---|---|
| | | Film Method | | |
| 1 | 0.025 | 170 ± 10 | 0.47 ± 0.1 | 72 ± 2.8 |
| 2 | 0.1 | 327 ± 19 | 0.29 ± 0.02 | 26 ± 4.7 |
| 3 | 0.2 | 427 ± 43 | 0.27 ± 0.06 | 12 ± 1.3 |
| | | Dialysis Method | | |
| 4 | 0.01 | 145 ± 2 | 0.16 ± 0.01 | 92 ± 6 |
| 5 | 0.025 | 153 ± 3 | 0.18 ± 0.06 | 89 ± 3.5 |
| 6 | 0.05 | 185 ± 10 | 0.5 ± 0.12 | 59 ± 8.3 |

Results are representative of triplicate samples (average ± SD); PDI = polydispersity index.

The amount of free doxorubicin, encapsulated doxorubicin, amount released during in vitro release study, and cell uptake was quantified using a gradient HPLC with the mobile phase consisting of trifluoroacetic acid (0.1% v/v) and acetonitrile 5% v/v~3 min, 80% v/v~11 min and 5% v/v~22 minutes, at a flow rate of 1 mL/min using fluorescence detector (505 nm as the excitation and 550 nm as the emission wavelengths).

$$\text{Encapsulation efficiency (\%)} = \frac{\text{Actual amount of doxorubicin loaded (mg/mg) into } \textit{PEG-Zein}}{\text{Amount of doxorubicin added (mg/mg) to } \textit{PEG-Zein}\text{(theoretical)}} \times 100$$

Figure 22:
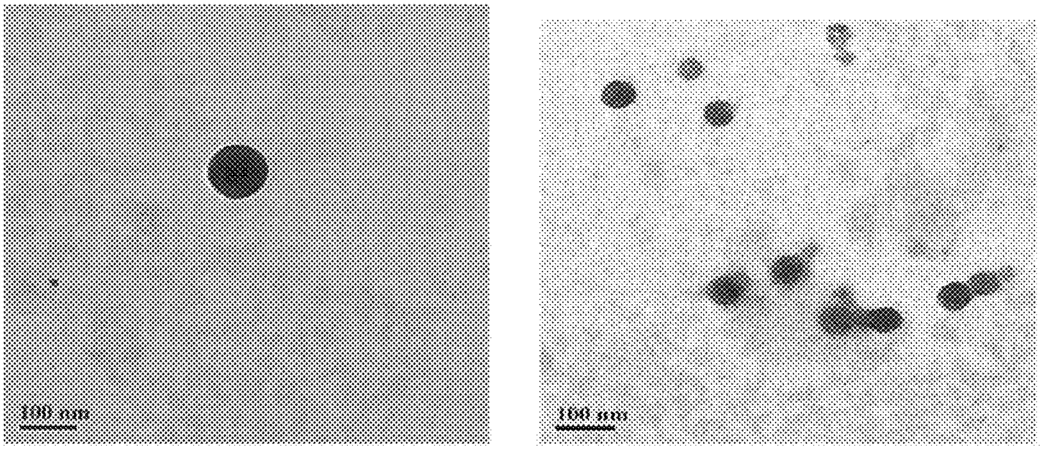
FIG. 22 illustrates a transmission electron microphotograph (TEM) of doxorubicin-loaded PEG-Zein micelles positively stained with 1% w/v uranyl acetate. Scale 1 mm=0.11 μm.
Figure 23:
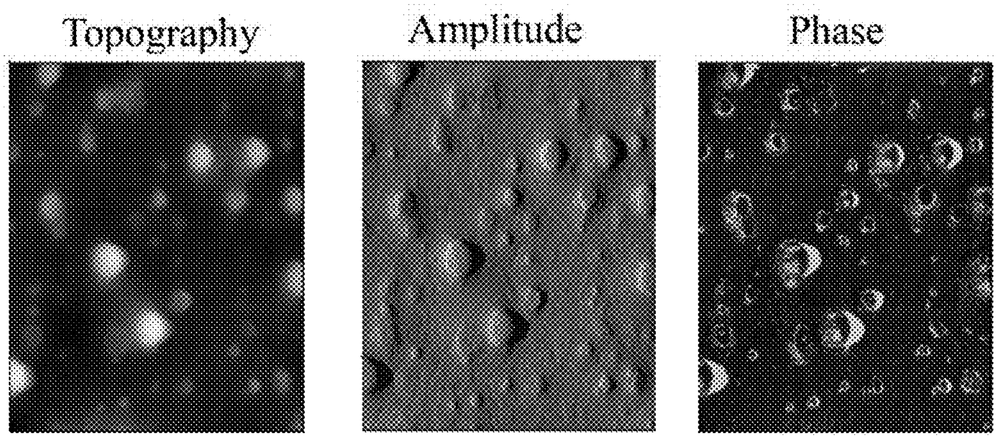
FIG. 23 illustrates atomic force microscopy (AFM) images of doxorubicin-loaded PEG-Zein micelles at scan rate of 2 μm in the non-tapping mode. Left to right are 2D topography, amplitude, and phase images of a representative sample with z-scale of 228 nm, 0.64 V, and 71°. The average particle size of 100 particles is 125±15 nm.

FIGS. 22 and 23 show transmission electron microscopic (TEM) and atomic force microscopy (AFM) images, respectively, of doxorubicin-loaded PEG-Zein micelles.

Doxorubicin is practically insoluble in water (15 ng/mL). However when incorporated into PEGylated zein micelles, the solubility increased by approximately 1000 fold (10 μg/mL).

Figure 24:
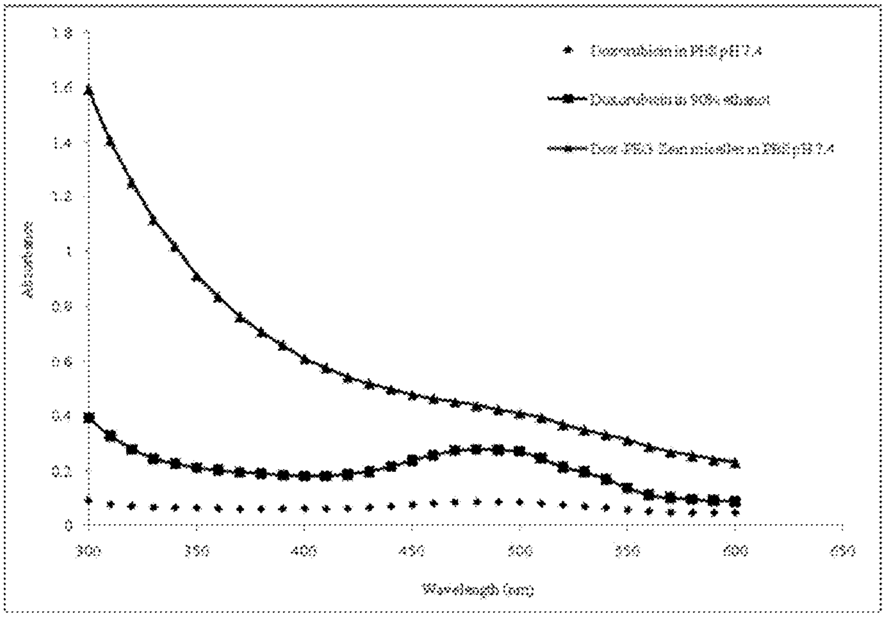
FIG. 24 illustrates the UV-Visible spectra of doxorubicin (10 μg/mL) in phosphate buffer pH 7.4, doxorubicin in 90% ethanol, and doxorubicin loaded PEGylated zein micelles in PBS pH 7.4, respectively. The absorbance of the doxorubicin-loaded PEG-Zein is higher than the absorbance of doxorubicin solubilized in 90% v/v ethanol, due to the enhanced aqueous solubility of doxorubicin in PEG zein micelles.

FIG. 24 illustrates the UV-Visible spectra of doxorubicin in phosphate buffer pH 7.4, 90% ethanol, and doxorubicin-loaded PEGylated zein micelles in PBS pH 7.4, respectively. The absorbance of the doxorubicin-loaded PEG-Zein is higher than the absorbance of doxorubicin solubilized in 90% (v/v) ethanol, which shows the enhanced aqueous solubility of doxorubicin-loaded PEG-zein micelles (1000 fold increase).

Figure 25:
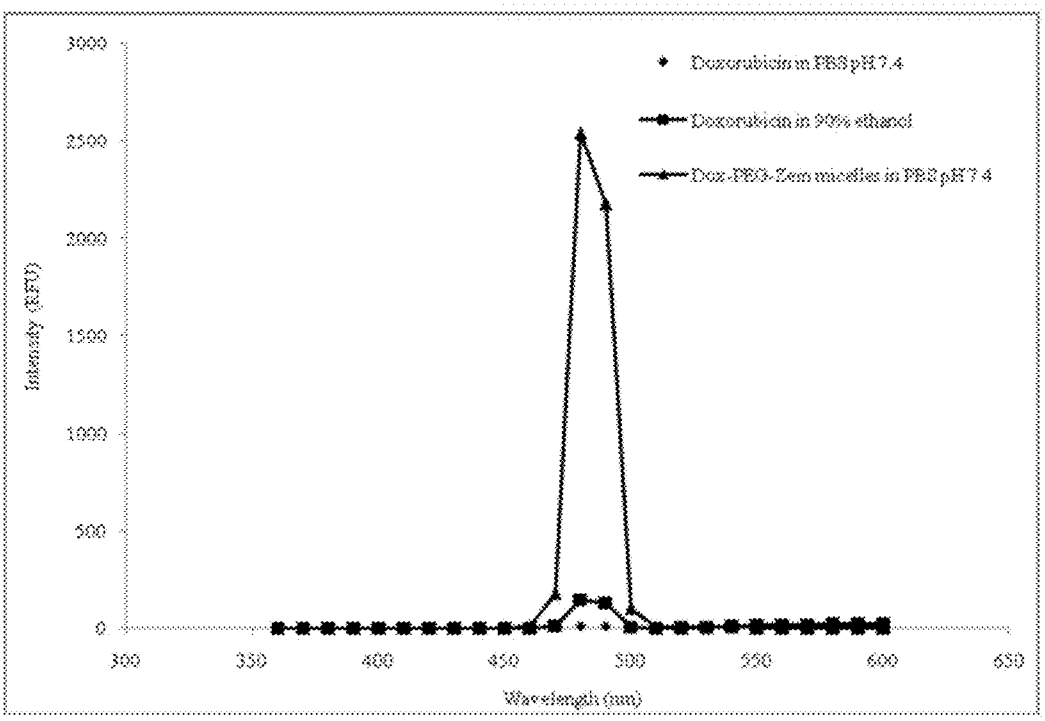
FIG. 25 illustrates a fluorescence spectra of doxorubicin (10 μg/mL) in phosphate buffer pH 7.4, 90% ethanol, and doxorubicin-loaded PEGylated zein micelles in PBS pH 7.4, respectively. There is a significant increase (approximately 50 fold) in doxorubicin fluorescence in PBS pH 7.4 after entrapment in PEGylated zein micelles due to the significantly enhanced aqueous solubility of doxorubicin.
Figure 26:
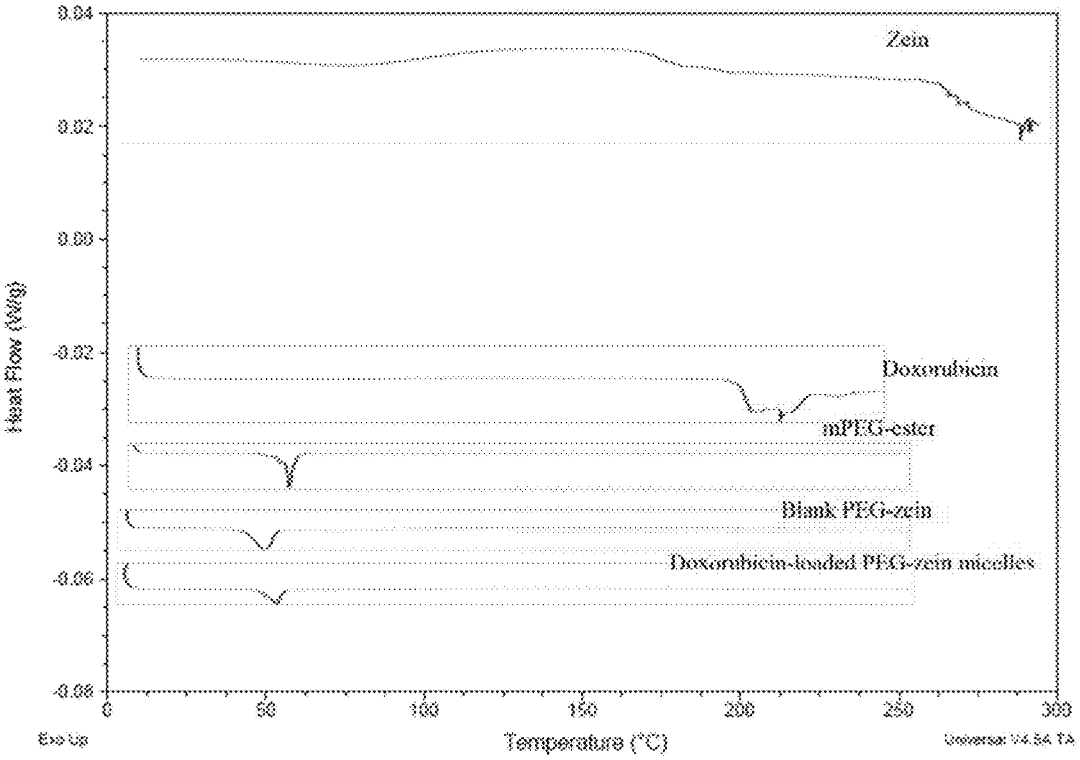
FIG. 26 illustrates differential scanning calorimetry (DSC) thermograms of zein, doxorubicin, blank PEG-Zein, mPEG-ester, and doxorubicin-loaded PEGylated zein micelles.
Figure 27:
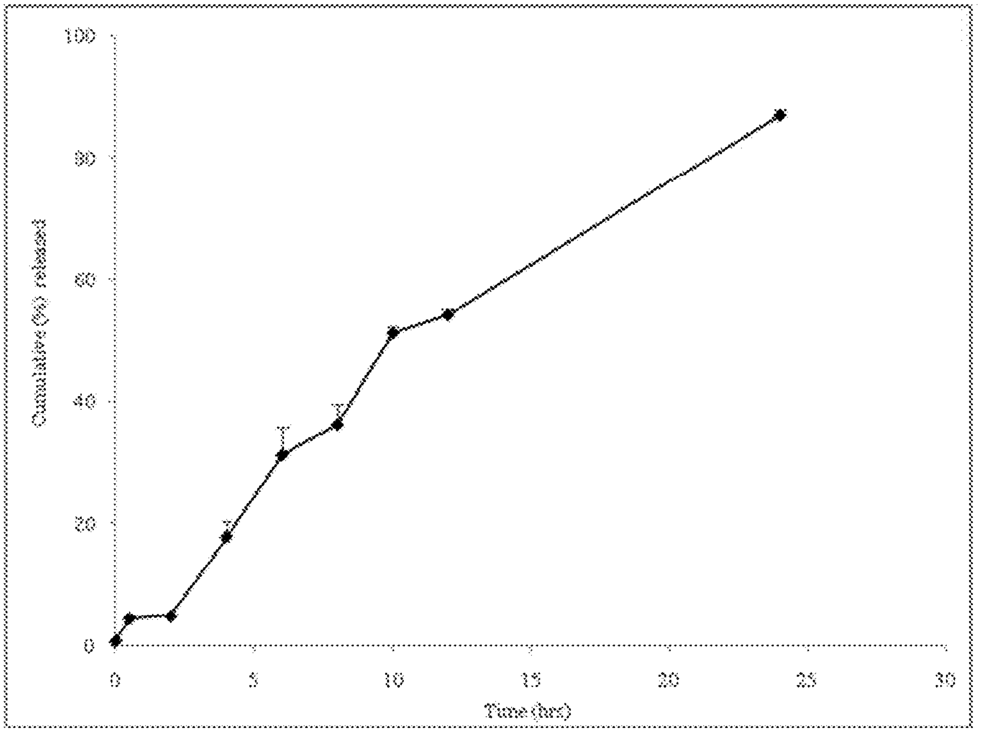
FIG. 27 illustrates an in vitro release profile of doxorubicin from PEG-Zein micelles in a citrate buffer pH 7.4 (n=3, ±SEM). Doxorubicin-loaded PEG-Zein micelles (1 mg/mL) were incubated in 1 mL of the citrate buffer pH 7.4 in a centrifuge tube and the suspension was maintained at 37° C. in a horizontal shaker water bath at 50 rpm. The sample was centrifuged at 12,000 rpm for 12 minutes. The supernatant was analyzed for doxorubicin released from the PEG-Zein micelles using HPLC analysis. A C18 column (WATERS™ Corporation, MA, USA) was used and the mobile phase consisted of trifluoroacetic acid (0.1% v/v) and acetonitrile 5% v/v (~3 min, 80% v/v~11 min and 5% v/v~22 minutes) at a flow rate of 1 mL/min. A fluorescence detector was used (505 nm as the excitation and 550 nm as the emission wavelengths, respectively). The release study was conducted for 24 hours. Each data point is a mean of three experiments±SD.

FIG. 25 shows fluorescence spectra of doxorubicin in phosphate buffer pH 7.4, 90% ethanol, and doxorubicin-loaded PEGylated zein micelles in PBS 7.4, respectively. There is a significant increase (approximately 50 fold) in doxorubicin fluorescence in PBS pH 7.4 after entrapment in PEGylated zein micelles due to the enhanced solubility of doxorubicin. Differential scanning calorimetry (DSC) thermograms of doxorubicin-loaded PEG-Zein micelles are shown in FIG. 26. The absence of a melting peak of doxorubicin indicates encapsulation of doxorubicin inside the core of the micelles. In vitro release of doxorubicin from PEG-Zein micelles is illustrated in FIG. 27. Release of doxorubicin was sustained for about 24 hours. PEGylated zein micelles are thus a promising carrier for doxorubicin.

Figure 28:
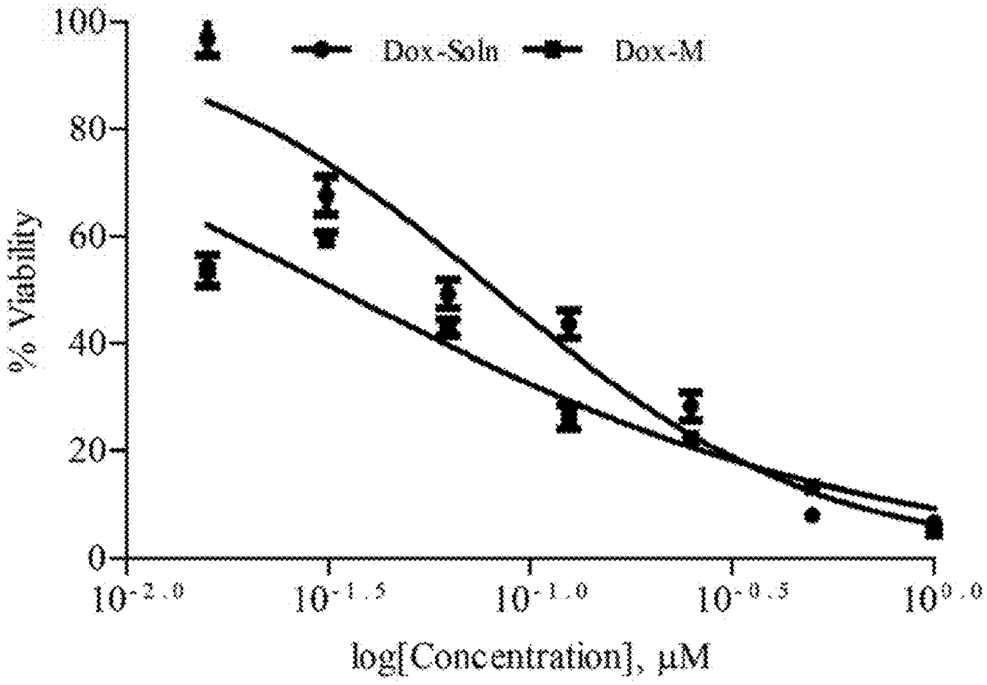
FIG. 28 illustrates an in vitro cytotoxicity profile of doxorubicin base (dissolved in 90% v/v ethanol) and PEG-Zein micelles. MCF-7 human breast cancer cells (2000 cells per well) were treated with doxorubicin solution (Dox-soln) and doxorubicin loaded micelles (Dox M) at a concentration range of 15.62 nM to 1000 nM for 4 days. On day 5 cytotoxicity analysis was performed using an MTT assay. Data points represents average±SE (n=4). The 1050 values of doxorubicin and doxorubicin micelles was 148 nM and 30 nM, respectively.

The therapeutic activity of doxorubicin-loaded PEGylated zein micelles prepared as described herein was tested in vitro against doxorubicin sensitive human breast cancer cells (MCF-7) and doxorubicin resistant human ovarian cancer cells (NCl/ADR/RES), and a doxorubicin sensitive human breast cancer cell line (MCF-7). FIG. 28 illustrates an in vitro cytotoxicity profile of doxorubicin (dissolved in 90% ethanol) and PEG-Zein micelles in MCF-7 cells. Cells at a seeding density of 2000 per well were exposed to a doxorubicin solution and doxorubicin micelles at concentration of 7.8 nM to 500 nM. After 24 hours, the respective drug treatments were removed. The cells were washed twice with ice cold phosphate buffer and replaced with fresh media. Media was replaced for every 48 hours. At day 5, cytotoxicity analysis was performed using the MTT assay.

Figure 29:
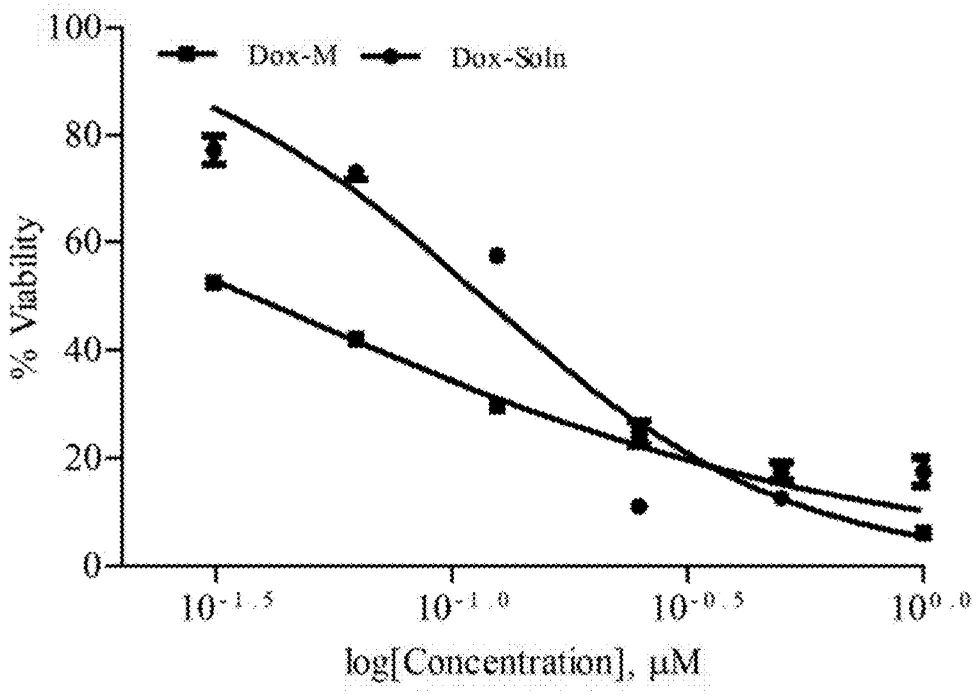
FIG. 29 illustrates an in vitro cytotoxicity profile of doxorubicin base (dissolved in 90% v/v ethanol) and doxorubicin loaded PEG-Zein micelles. NCl/ADR-RES drug resistant human ovarian cancer cells (2000 cells per well) that are drug resistant were treated with doxorubicin solution (Dox-soln) or doxorubicin micelles (Dox-M) in the concentration range of 31.25 nM to 1000 nM for 4 days. On day 5 cytotoxicity analysis was measured using an MTT assay. Data points represent average±SE (n=4). The $IC_{50}$ values for the doxorubicin and doxorubicin micelles were 126 nM and 29 nM, respectively.

The $IC_{50}$ value for doxorubicin micelles was half that of the pure doxorubicin treatment. FIG. 29 illustrates an in vitro cytotoxicity profile of doxorubicin base (dissolved in 90% v/v ethanol) and PEG-Zein micelles in an NCl/ADR-RES cell line. Cells at seeding density of 2000 cells per well were exposed to doxorubicin base and doxorubicin micelles at concentration of 31.25 nM to 1000 nM. After 24 hours the respective drug treatments were removed. The cells were washed twice with ice cold phosphate buffer and replaced with fresh media. Media was replaced for every 48 hours. On day 5 cytotoxicity analysis was performed using an MTT assay. The $IC_{50}$ value for the doxorubicin micelle was 4 times lower than that of the free doxorubicin treatment. The results of the in vitro cytotoxicity assay of doxorubicin-loaded PEGylated zein micelles in human cancer cell lines showed that the doxorubicin-loaded in PEGylated zein micelles had a significantly higher effective potency than the free doxorubicin solution. The difference in potency can be attributed to the difference in the cell uptake kinetics of the free drug compared to the doxorubicin loaded PEGylated zein micelles.

Figure 30:
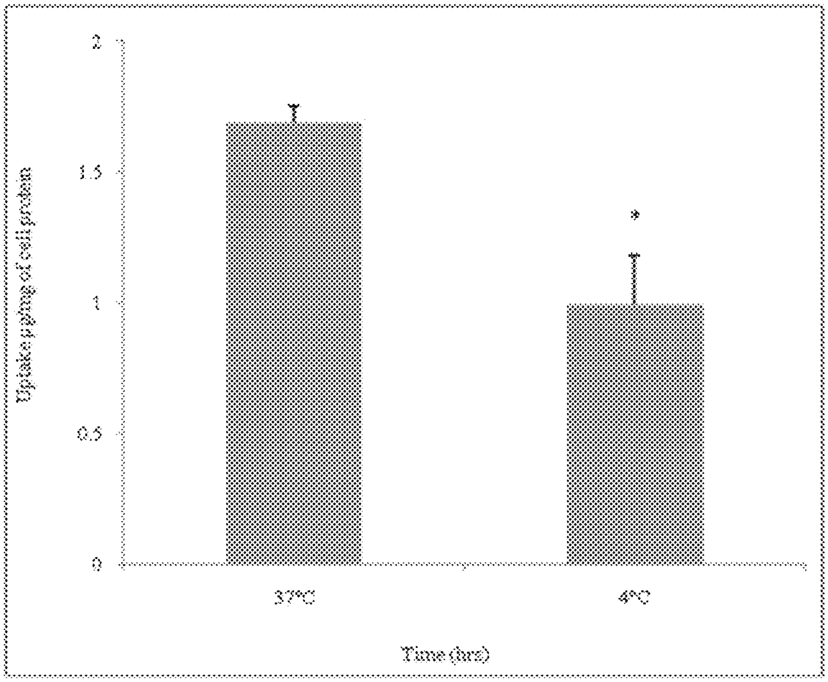
FIG. 30 illustrates the influence of temperature on cellular uptake of doxorubicin loaded PEG-Zein micelles in an NCl/ADR-RES cell line. Cells were pre-incubated at 4° C. for 2 hours. After 2 hours cells were washed twice with PBS pH 7.4, treated with the doxorubicin loaded PEG-Zein micelles (corresponding to 5 μg/mL of doxorubicin). After two hours, the treatment was removed and cells were washed twice with ice cold PBS pH 7.4, and the amount of doxorubicin content in the cell lysate was estimated using HPLC analysis. In the control group, cells were incubated at 37° C. Each value represents average±SE (n=3). The cell uptake at 4° C. was significantly lower compared the cell uptake at 37° C. (p<0.05; student t-test).

Free doxorubicin is taken up by passive diffusion dictated by the concentration gradient, while the doxorubicin-loaded micelles are taken up an active endocytosis process. FIG. 30 illustrates the influence of temperature on cellular uptake of doxorubicin loaded PEG-zein micelles in NCl/ADR-RES cell line. Cells were pre-incubated at 4° C. for 2 hours. After 2 hours the cells were washed twice with PBS pH 7.4 and were treated with the micelles (amounts corresponding to 5 μg/mL of doxorubicin). After two hours the treatments were removed, the cells were washed twice with ice cold PBS pH 7.4, and the amount of doxorubicin content in the cell lysate at different time intervals was estimated using HPLC analysis.

Figure 31:
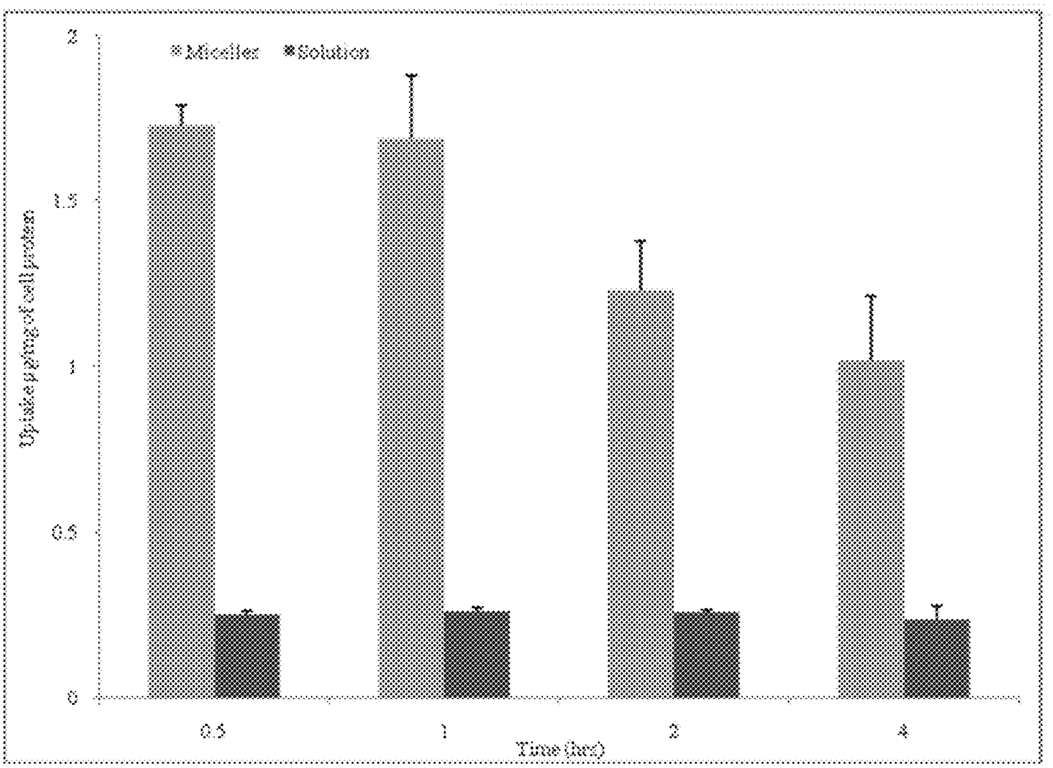
FIG. 31 illustrates the kinetics of cellular uptake of doxorubicin-loaded PEG-Zein micelles and doxorubicin solution (51 Lig/mL) in NCl/ADR-RES cell line (50000 cells/plate). Data points represent mean of three experiments±SE.

The cell uptake was significantly reduced at low temperature signifying that the cell uptake of PEG-zein micelles is an active endocytosis process. FIG. 31 illustrates the kinetics of cellular uptake of doxorubicin-loaded PEG-Zein micelles and a solution in NCl/ADR-RES cell line (5 μg/mL of doxorubicin or doxorubicin-loaded PEG-zein micelles (5000 cells/well)). Higher cell uptake of doxorubicin micelles was observed in comparison to plain doxorubicin solution at all time points. Furthermore, the endocytotic uptake of doxorubicin micelles overcame the drug efflux pumps in resistant cancer cells, thus increasing the drug efficacy.

Figure 32:
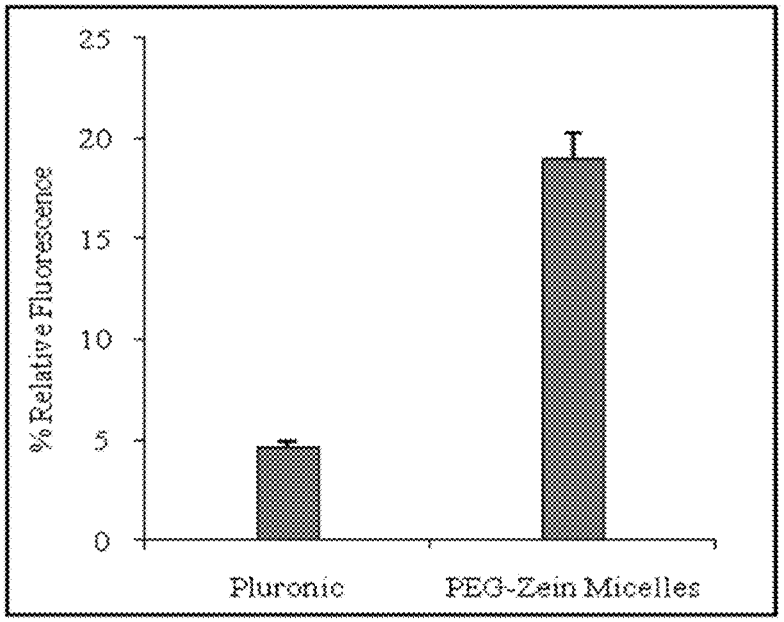
FIG. 32 illustrates the mechanism of cell uptake of PEG-zein micelles in resistant human cancer cells. NCl/ADR-RES cells (5000 cells/well) were treated PLURONIC F68 (1 mg/mL; positive control; a block-copolymer known to inhibit P-glycoprotein (P-gp)), and blank PEG-Zein micelles (0.050 mg/mL). After 30 minutes of incubation at 37° C., 50 μL of 0.25 μM/L of calcein AM was added. Fluorescence was measured every 5 minutes for 1 hour using a micro plate reader (485/589 Excitation/Emission wavelengths) at room temperature. P-gp inhibition was calculated as follows: % relative fluorescence=100×$(FL_{treatment}-FL_{Non\text{-}treatment})/FL_{Non\text{-}treatment})$. Data points represent average±SE (n=8). A higher P-gp inhibition was observed with blank PEG-Zein micelles.

FIG. 32 illustrates the influence of PLURONIC F68 treatment (1 mg/mL), and blank PEG zein micelles (0.050 mg/mL) on P-gp activity (Calcein AM assay) in NCl/ADR-RES cells. Calcein AM is non-fluorescent and readily diffuses into cells. Calcein AM, but not calcein, is a substrate for P-gp. In the presence of P-gp inhibitors, calcein AM enters the cell and is converted to calcein by intracellular esterases. Fluorescence increased with increased intracellular calcein concentrations. From the data illustrated in FIG. 32, it is evident that significant P-gp inhibition is observed with blank PEG-zein micelles. Targeting ligands can also be attached to facilitate delivery of the drug loaded PEG-zein nanomicelles to a target site in vivo.

Figure 33:
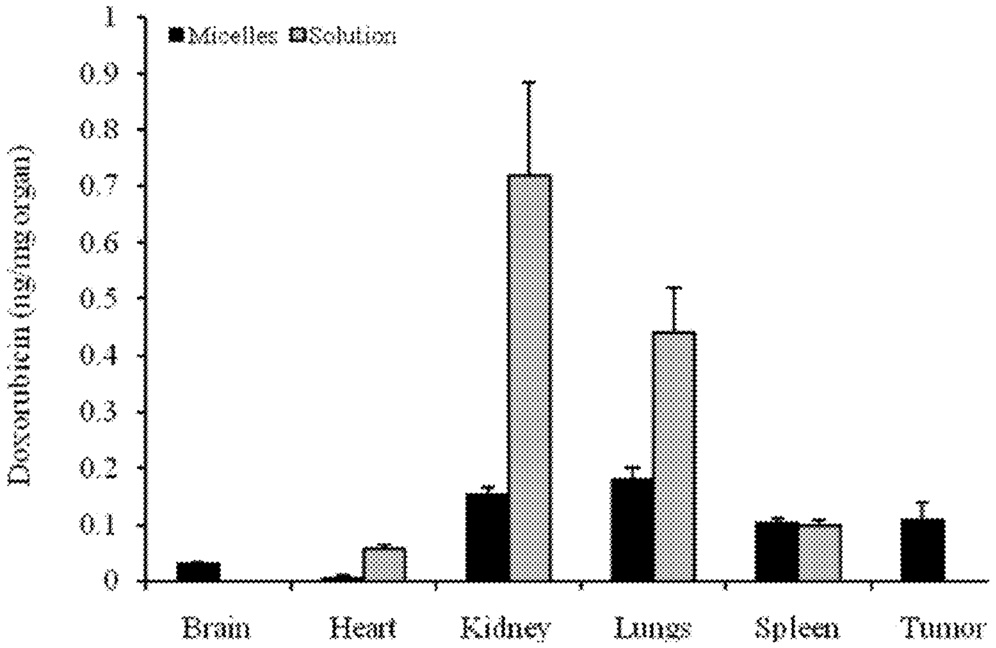
FIG. 33 illustrates in vivo biodistribution of doxorubicin solution and doxorubicin loaded PEG-Zein micelles (in saline) in mice allograft breast tumor mouse model. The tumor model was developed by subcutaneous injection of JC mouse breast cancer cells. Doxorubicin solution or micelles were given by tail vein injection (4.5 mg/kg). Animals were sacrificed 3 hours after treatment administration. Tumor and organs were collected. Doxorubicin concentration in tumors and organs were determined using a fluorescence based isocratic HPLC method. Doxorubicin content was normalized to the organ weight (n=3-4, ±SEM). Micelles resulted in higher distribution to the tumor and significantly lower distribution in other organs. Doxorubicin is known to cause cardiotoxicity and renal toxicity. The results show that micelles lead to enhanced efficacy and reduced toxicity of doxorubicin.

FIG. 33 shows the in vivo biodistribution of doxorubicin loaded PEG-zein micelles in an allograft mouse tumor model. Female nude mice (Charles River Laboratories, Wilmington, Mass.) were used in the study. JC mouse breast cancer cells ($1\times10^7$ cells) were suspended in PBS and injected subcutaneously. When the tumor volume reached ~150 to 200 $mm^3$, animals received intravenous injections of doxorubicin solution or doxorubicin loaded PEG-zein micelles (3 mg/kg). After 3 hours, the mice were sacrificed and organs (liver, heart, lungs, spleen, brain and tumor) were collected and homogenized in 2 mL deionized water using a tissue homogenizer. After addition of 100 ng of daunorubicin (internal standard), tissue homogenates were lyophilized.

Dry tissues were weighed and extracted with 5 mL of methanol/chloroform mixture (65:35) using a shaker for 5 hours in the dark at room temperature. The extract was centrifuged at 13,000 rpm for 10 minutes at 4° C. The supernatant was evaporated under nitrogen gas and reconstituted in methanol/acetonitrile (50:50). The amount of doxorubicin in the organs was quantified using a reverse phase HPLC method (27 (acetonitrile): 73 (20 mM potassium hydrogen phosphate (monobasic) buffer (pH: 2.5)) using a fluorescence detector (excitation wavelength 505 nm and emission wavelength 550 nm). The amount of doxorubicin in the organs was expressed as the amount (ng) per mg of dry organ.

As can be observed in FIG. 30, a higher drug accumulation was found in tumors while there was no drug accumulation of the free doxorubicin solution in the tumors. The drug concentration in heart and kidney tissue was significantly lower with doxorubicin PEG-zein micelles compared to the free doxorubicin solution samples. Doxorubicin chemotherapy is limited by cardiac and renal toxicity. These results demonstrate enhanced tumor accumulation and reduced toxicity of doxorubicin loaded PEG-zein micelles.

The efficacy of doxorubicin PEG zein micelles was studied by measuring the change in tumor volume in an allograft breast tumor mouse model. Female BALB/c mice (Charles River Laboratories, Wilmington Mass.) were used in the study. JC mouse breast tumor cells ($1\times10^7$ cells) were suspended in PBS and injected subcutaneously. When the tumor volume reached ~150 to 200 $mm^3$, animals received two doses of intravenous doxorubicin solution or doxorubicin loaded PEG-zein micelles (3 mg/kg, on days 0 and 7). The tumor volume was measured using a Vernier Caliper.

Figure 34:
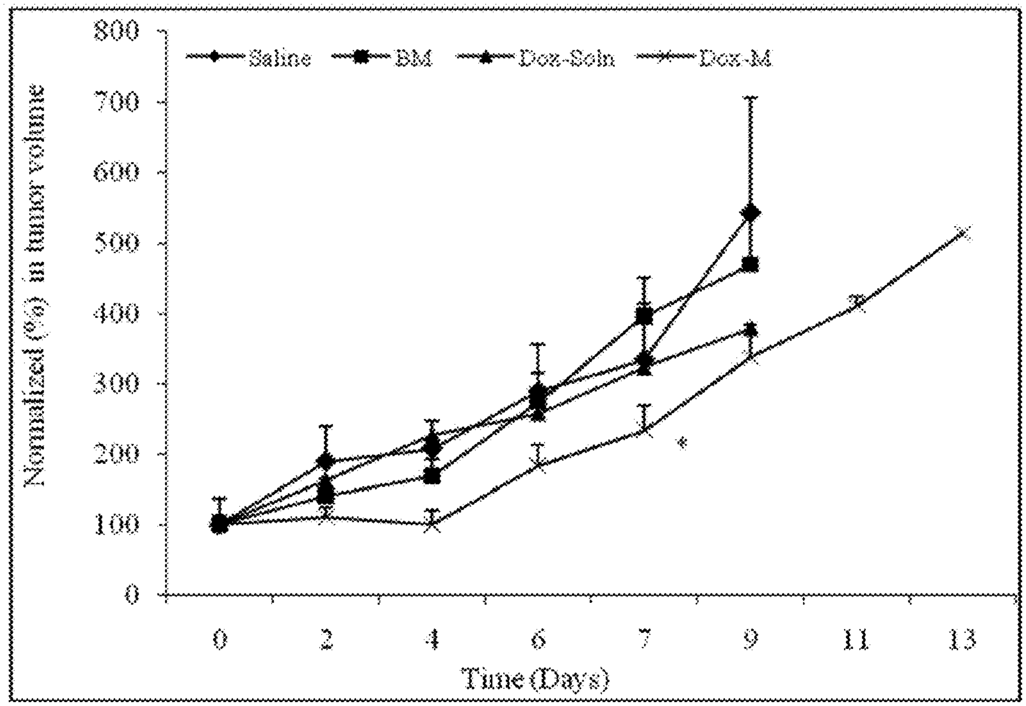
FIG. 34 illustrates in vivo anticancer efficacy of doxorubicin solution and doxorubicin loaded PEG-zein micelles in drug resistant tumor allograft mouse tumor model. Female BALB/C bearing subcutaneous JC mouse breast cancer cells were used for the study. The mice were injected with doxorubicin solution or micelles by i.v. injection on days 0 and day 7 (3 mg/kg). Tumor volume was measured on alternate days. Percent reduction in tumor volume was calculated using the equation (tumor volume after treatment/tumor volume before treatment)×100. Data is represented as mean±SEM, n=4-5 per group; * indicates the value is significant at p<0.05 compared to other treatments. Except for the doxorubicin micelles group, the mice did not survive after 7 days in all the other treatment groups. Tumors grew slowly when doxorubicin micelles were administered, signifying the greater efficacy of the micelle formulation. BM refers to blank micelles; Dox-Soln refers to a doxorubicin solution; and Dox-M refers to doxorubicin loaded PEG-Zein micelles.
Figure 35:
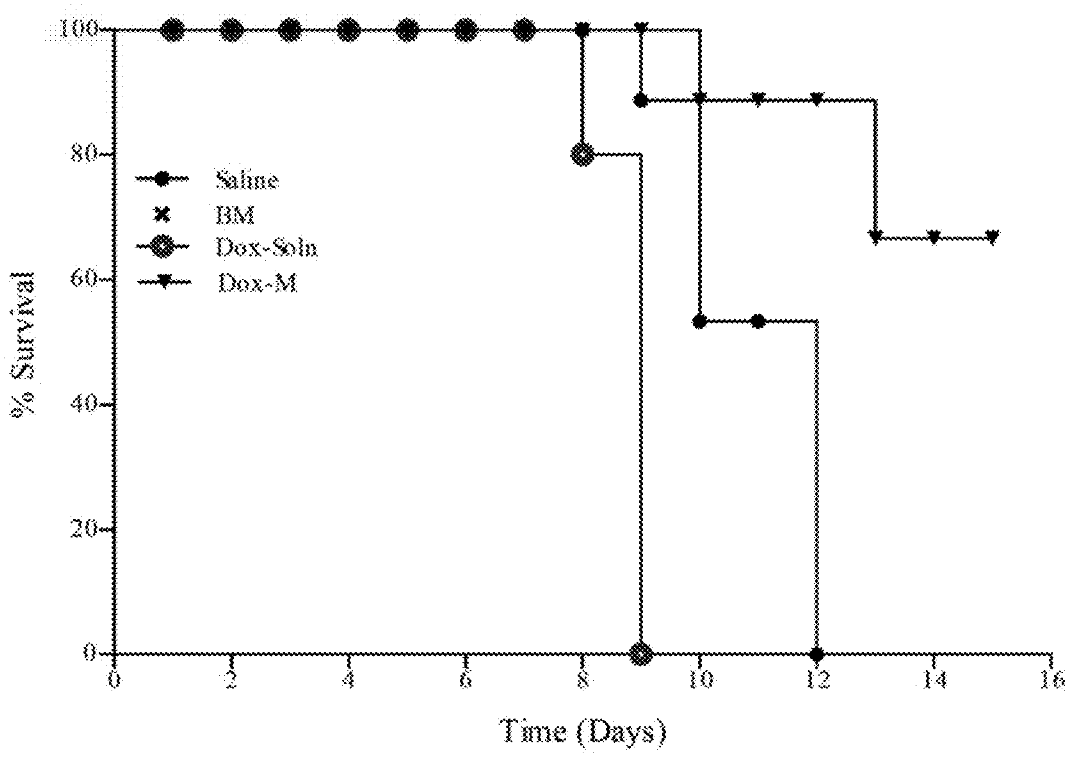
FIG. 35 illustrates Kaplan-Meier survival plot of BALB/C mice bearing allogenic breast tumors. Female BALB/C bearing subcutaneous JC tumors were injected with doxorubicin solution or doxorubicin micelles by i.v. injection (6 mg/kg), on day 0 and 7 in divided doses. Percent survival of animals was plotted using the Graph Pad 5 software. Data is mean of 4-5 animals per group. Mortality rate of mice were in the increasing order of Dox micelles (Dox-M)<Dox-solution (Dox-Soln)<saline<blank micelles (BM). The data shows that doxorubicin micelles resulted in greater survival due to enhanced efficacy of the formulation.

FIG. 34 shows the increase in tumor volume after different treatments. As can be seen in FIG. 34, the increase in tumor volume was significantly lower with the doxorubicin PEG-zein micelles. The mice treated with doxorubicin PEG-zein micelles also lived longer than the other treatment groups (FIG. 35). The results demonstrate the enhanced efficacy of doxorubicin loaded PEG-zein micelles.

Example 3

PEGylated Zein Micelles Encapsulating Curcumin

Curcumin is the principal curcuminoid of the Indian spice turmeric, which is a member of the ginger family (Zingiberaceae). Two other curcuminoids are desmethoxycurcumin and bis-desmethoxycurcumin. Curcumin can exist in at least two tautomeric forms, of which the enol form is more energetically stable in the solid phase and in solution. Curcumin has a molecular weight (m.w.) of 368.4, a Log P of 2.5, is practically insoluble in water and is soluble in methanol.

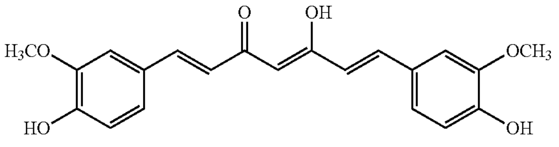

curcumin

Figure 9:
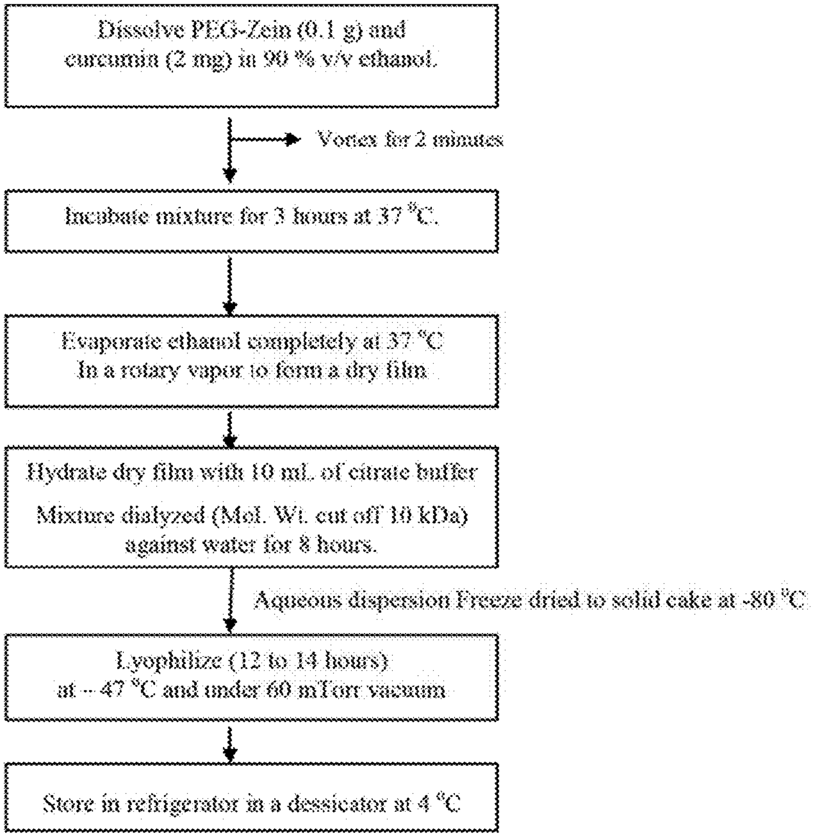
FIG. 9 illustrates steps of preparing curcumin-loaded PEGylated zein micelles using a film method, according to an embodiment.
Figure 10:
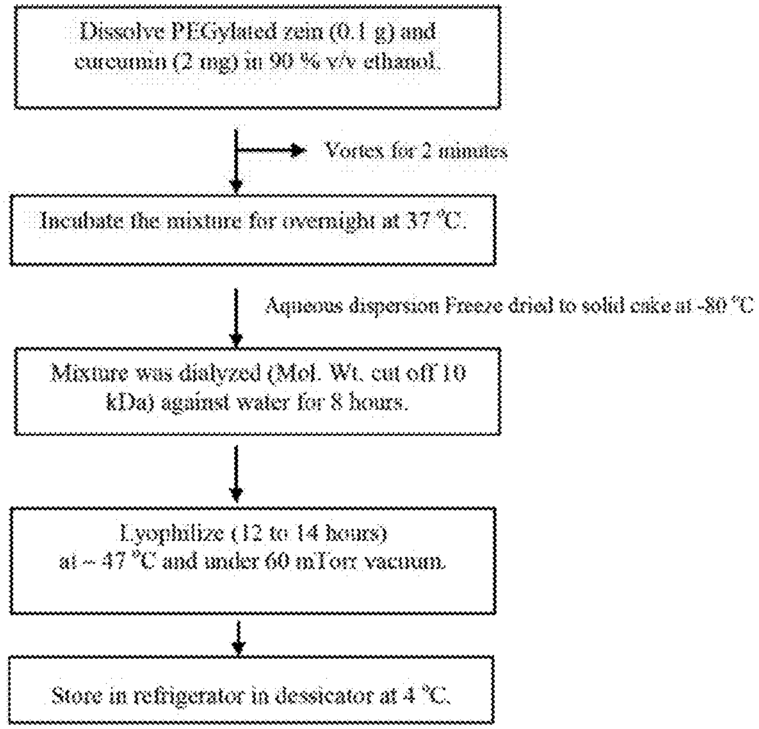
FIG. 10 illustrates steps of preparing curcumin-loaded PEGylated zein micelles using a dialysis method, according to an embodiment.

Clinical trials are studying the effect of curcumin on various diseases including multiple myeloma, pancreatic cancer, myelodysplastic syndromes, colon cancer, psoriasis, and Alzheimer's disease. In vitro and animal studies indicate that curcumin has antitumor, antioxidant, antiarthritic, anti-amyloid, anti-ischemic, and anti-inflammatory properties, as well as other biological activities (Aggarwal et al., Adv Exp Med Biol 2007, 595:1-75). FIGS. 9 and 10 illustrate the stepwise preparation of curcumin-loaded PEG-Zein micelles using film hydration and dialysis methods, respectively. In both film hydration and dialysis methods, 0.1 g of PEG-Zein and 0.002 g of curcumin was dissolved in 20 mL of 90% ethanol. The mixture was incubated overnight (stirred at 50 rpm) at 37° C. to allow partitioning of curcumin into the hydrophobic zein core. The hydroalcoholic solvent was then completely removed using a rotary evaporation device to form a film. The dried film of curcumin-loaded PEG-Zein micelles was reconstituted in citrate buffer, pH 7.4, and was sonicated for 5 minutes to form a uniform suspension. The mixture was then dialyzed (m.w. cut off=~10,000 Da) against water with stirring (100 rpm) at room temperature for 24 hours to remove free curcumin.

In the dialysis method, after overnight incubation, the mixture was dialyzed (m.w. cut off 10,000 Da) against water in a magnetic stirrer (at 100 rpm) at room temperature for 24 hrs to remove free curcumin. The resulting product was then frozen to −80° C. followed by freeze drying at −47° C. at 60 mTorr vacuum for 12 to 14 hours. The lyophilized product was stored in dessicator at 4° C.

Tables 5 and 6 below illustrate various characteristics of curcumin-loaded PEGylated zein micelles prepared using a thin film method and a dialysis method, respectively.

TABLE 5

| Sample | Curcumin (% w/w) | Particle size (nm) | PDI | Encapsulation Efficiency (%) |
|---|---|---|---|---|
| 1 | 0.25 | 166 ± 10 | 0.4 ± 0.1 | 92 ± 3.5 |
| 2 | 0.5 | 139 ± 2 | 0.43 ± 0.05 | 76 ± 11 |
| 3 | 1 | 176 ± 9 | 0.4 ± 0.12 | 47 ± 17 |
| 4 | 2 | 185 ± 13 | 0.52 ± 0.06 | 38 ± 4 |

Results are representative of triplicate samples (average ± SD); PDI = polydispersity index.

TABLE 6

| Sample | Curcumin (% w/w) | Particle size (nm) | PDI | Encapsulation Efficiency (%) |
|---|---|---|---|---|
| 1 | 1 | 124 ± 4.1 | 0.25 ± 0.03 | 95 ± 4 |
| 2 | 1.25 | 127 ± 2.6 | 0.31 ± 0.01 | 94 ± 7 |
| 3 | 1.66 | 148 ± 7 | 0.34 ± 0.09 | 87 ± 15 |
| 4 | 2.5 | 152 ± 2.5 | 0.35 ± 0.03 | 74 ± 09 |
| 5 | 5 | 154 ± 1 | 0.45 ± 0.04 | 60 ± 13 |
| 6 | 4 | 175 ± 1.7 | 0.38 ± 0.03 | 63 ± 11 |

TABLE 6-continued

Results are representative of triplicate samples (average ± SD); PDI = polydispersity index.

The concentration of free curcumin and encapsulated curcumin was assayed by RP-HPLC using a C18 column. The mobile phase consisted of 60% acetonitrile and 40% citric buffer (1% (w/v) citric acid solution adjusted to pH 3.0 using 50% (w/w) sodium hydroxide solution). The flow rate was 1.0 mL/min and the detection wavelength was 420 nm.

$$\text{Encapsulation efficiency (\%)} = \frac{\begin{array}{c}\text{Actual amount of curcumin}\\ \text{loaded (mg/mg) into } \textit{PEG-Zein}\end{array}}{\begin{array}{c}\text{Amount of curcumin added}\\ \text{(mg/mg) to } \textit{PEG-Zein}\text{(theoretical)}\end{array}} \times 100$$

Figure 11:
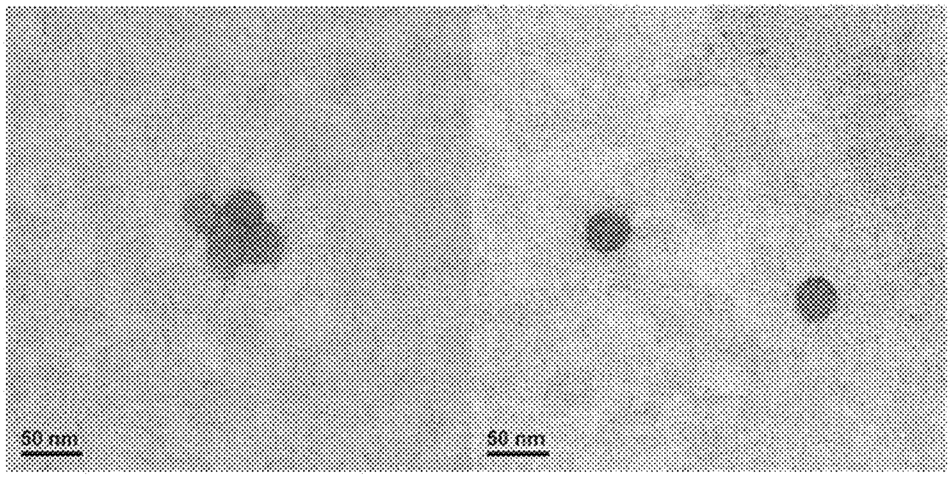
FIG. 11 illustrates a transmission electron microphotograph (TEM) of curcumin-loaded PEG-Zein micelles positively stained with 1% w/v uranyl acetate. Scale 1 mm=0.05 gm.
Figure 12:
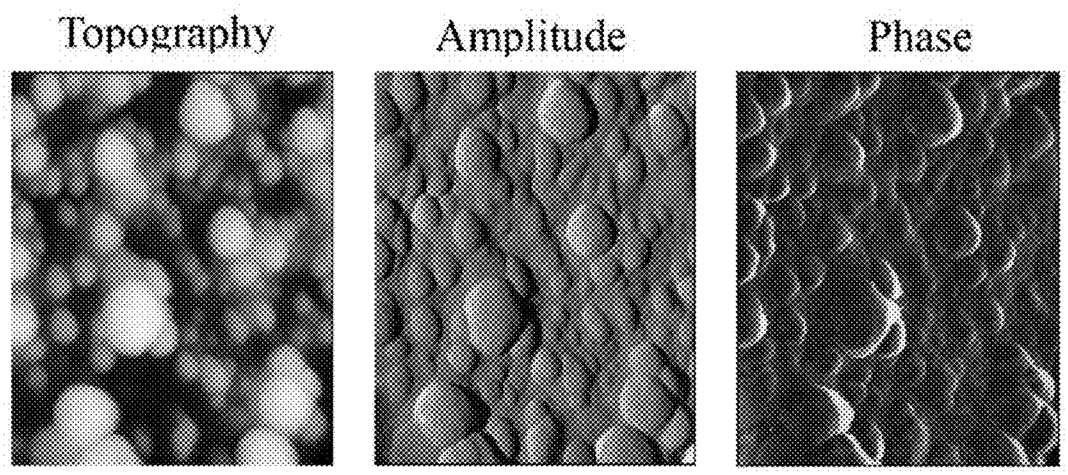
FIG. 12 illustrates atomic force microscopy (AFM) images of curcumin-loaded PEG-Zein micelles at scan rate of 2 μm in the non-tapping mode. Left to right are 2D topography, amplitude, and phase images of a representative sample with z-scale of 88 nm, 0.39 V, and 61°, respectively. The average particle size of 100 particles measured in AFM was 90±10 nm.
Figure 13:
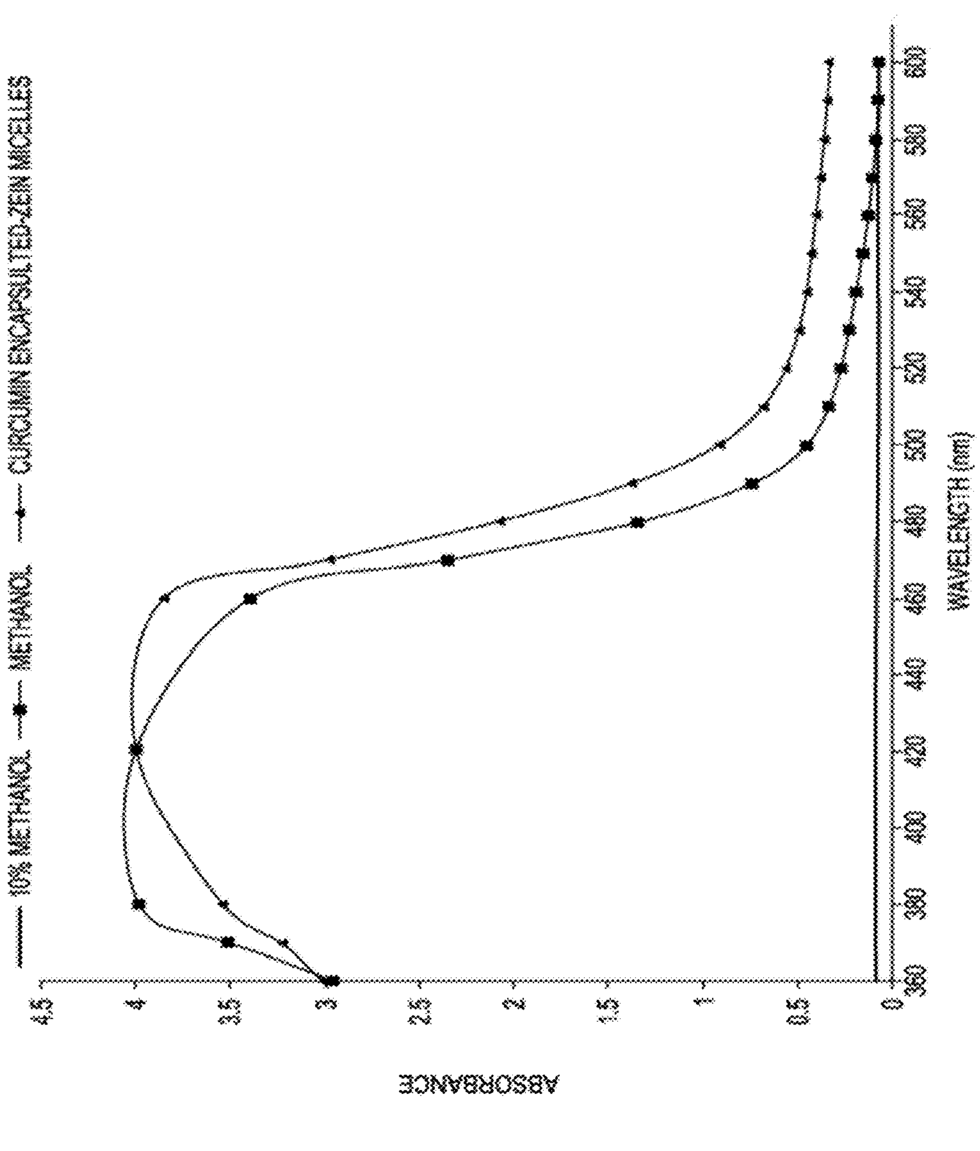
FIG. 13 illustrates a UV-Visible spectrum of curcumin (10 μg/mL) in methanol, PBS pH 7.4 (with 10% methanol) and curcumin-loaded PEGylated zein micelles in PBS pH 7.4. The absorbance of curcumin-loaded PEG-Zein is similar to the absorbance of curcumin solubilized in methanol, showing the increased water solubility of curcumin loaded PEG-zein micelles.
Figure 14:
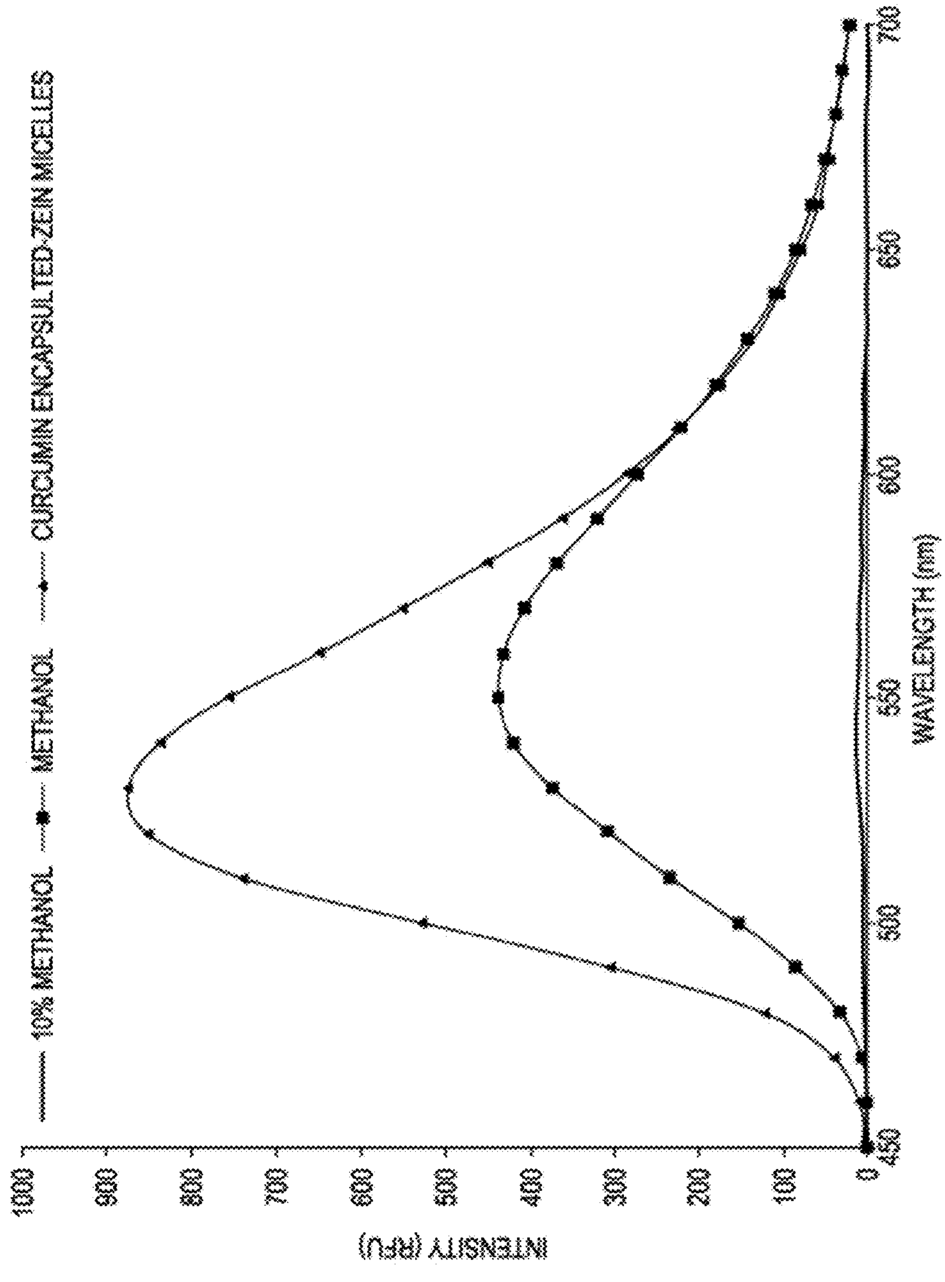
FIG. 14 illustrates the fluorescence spectra of curcumin (10 μg/mL) in methanol, PBS pH 7.4 (with 10% methanol) and curcumin-loaded PEGylated zein micelles in PBS pH 7.4. The shift of the $\lambda_{max}$ of the emission spectra of curcumin from 540 nm to 525 nm shows that the curcumin is entrapped in the micelles. There is also a significant increase (approximately 4 fold) in curcumin fluorescence in water after entrapment in PEGylated zein micelles due to the significantly enhanced aqueous solubility of curcumin.

FIGS. 11 and 12 show transmission electron microscopic (TEM) and atomic force microscopy (AFM) image of curcumin loaded PEG-Zein micelles. Curcumin is practically insoluble in water (11 ng/mL) (B. Aggarwal et al. (2007), Adv Exp Med Biol 595:1-75). However when incorporated into PEGylated zein micelle, the solubility increased by approximately 2000 fold (20 μg/mL). FIG. 13 is a UV-Visible spectra of curcumin in 10% methanol and curcumin-loaded PEGylated zein micelles in PBS pH 7.4. It is evident from the spectra that the absorbance of the curcumin loaded PEG-Zein is similar to the absorbance of curcumin solubilized in 10% (v/v) methanol. Thus PEG-Zein significantly enhanced the aqueous solubility of curcumin by approximately 2000 fold. FIG. 14 is a fluorescence spectra of curcumin in 10% methanol and curcumin loaded PEGylated zein micelles in PBS pH 7.4. The shift of the Xmax of the emission spectra of curcumin from 540 nm to 525 nm shows that the curcumin is entrapped in the micelles. Furthermore, there is a significant increase (approximately 4 fold) in curcumin fluorescence in water after entrapment in PEGylated zein micelles due to enhanced aqueous solubility of curcumin. The encapsulation in the core stabilized curcumin against degradation from environmental agents, such as hydrolysis and photodegradation.

Table 7, below, illustrates the stability of curcumin-loaded PEGylated zein micelles in the presence of light and pH variation. Stability of curcumin is improved when encapsulated in PEG-zein micelles (half life 31.8 minutes), in comparison to plain solution (half life 4 minutes) (phosphate buffer pH 7.4). Stability was remarkably enhanced in phosphate buffer pH 5 (half life=6.9 minutes, compared to micelles, $t_{1/2}$=366 minutes).

TABLE 7

| Sample | Formulation | Conditions | $t_{1/2}$ (min) |
|---|---|---|---|
| 1 | Curcumin* | pH 7.4 | 4 |
| 2 | Curcumin loaded PEG-zein micelles | pH 7.4 | 31.8 |
| 3 | Curcumin* | pH 5 | 6.9 |
| 4 | Curcumin loaded PEG-zein micelles | pH 5 | 366 |

*10% v/v methanol was used to solubilize curcumin.

Figure 15:
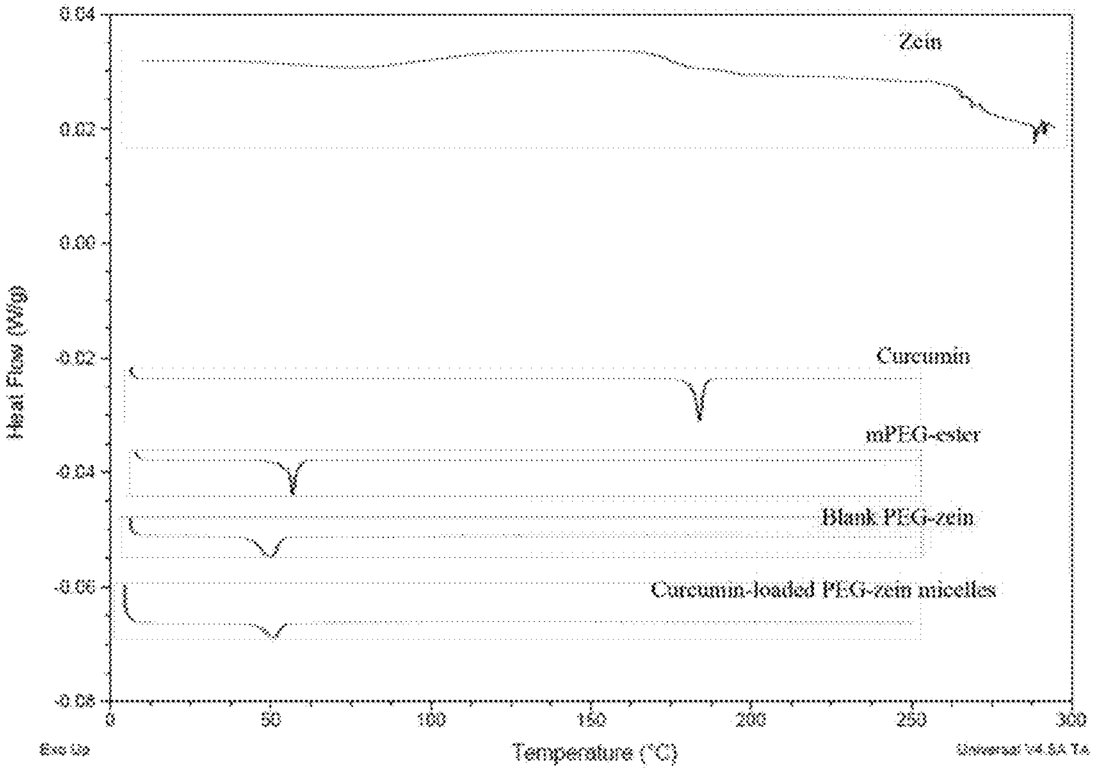
FIG. 15 illustrates differential scanning calorimetry (DSC) thermograms of zein, curcumin, blank PEG-Zein, mPEG-ester, and curcumin-loaded PEGylated zein micelles.
Figure 16:
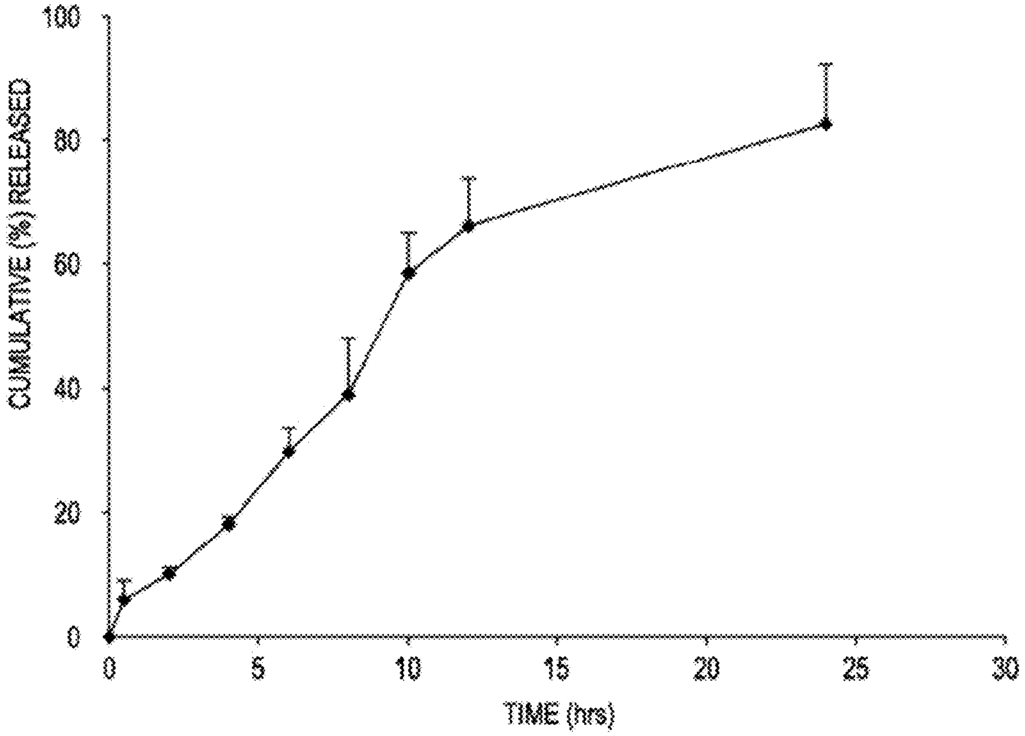
FIG. 16 illustrates an in vitro release profile of curcumin from PEG-Zein micelles in citrate buffer pH 7.4 (average±SE; n=3). Curcumin loaded PEG-Zein micelles (1 mg/mL) were prepared by a dialysis method as described herein, were incubated in 1 mL of citrate buffer pH 7.4 in a centrifuge tube, and the suspension was maintained at 37° C. in a horizontal shaker water bath at 50 rpm. The sample was centrifuged at 12,000 rpm for 12 minutes. The supernatant was then analyzed for curcumin released from the PEG-Zein micelles using HPLC. A C18 column (WATERS™ Corporation, Mass., USA) was used and the mobile phase consisted of 60% acetonitrile and 40% citric buffer (1% (w/v) citric acid solution adjusted to pH 3.0 using 50% (w/w) sodium hydroxide solution). The flow rate was 1.0 mL/min and the detection wavelength was 420 nm. The release study was conducted for 24 hours. Each data point is a mean of three experiments±SD.
Figure 17:
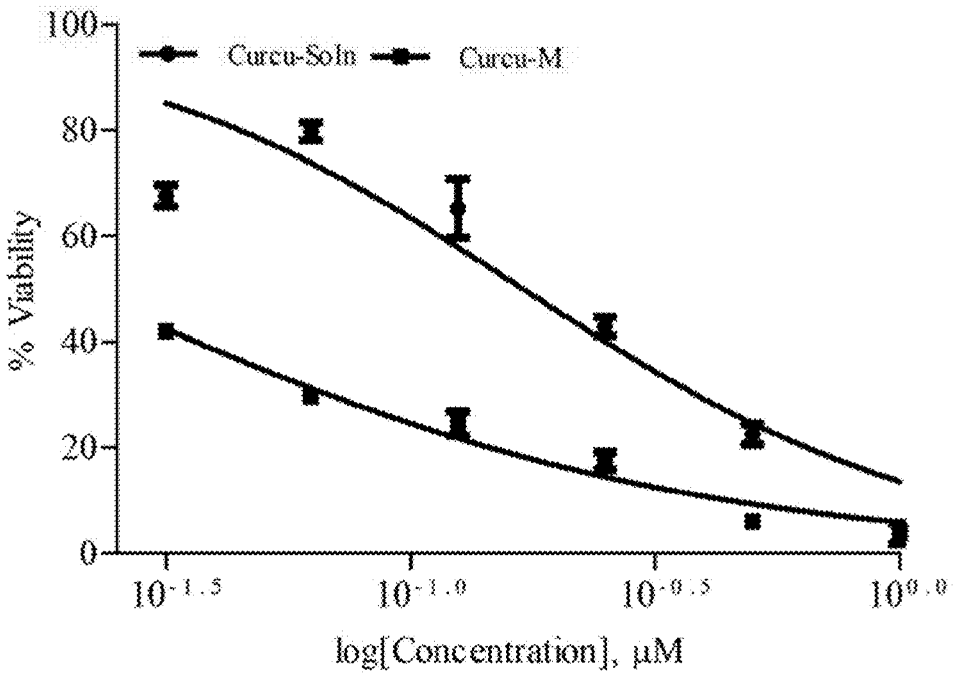
FIG. 17 illustrates an in vitro cytotoxicity profile of curcumin (dissolved in 10% DMSO) and curcumin micelles. NCI/ADR-RES drug resistant human ovarian cancer cells (2000 cells per well) that are drug resistant were treated with curcumin solution or curcumin micelles in the concentration range of 7.8 nM to 500 nM for 4 days. On the fifth day cytotoxicity analysis was performed using an MTT assay. Data points represent average±SE (n=4). The $IC_{50}$ value for curcumin solution (Curcu-soln) and curcumin micelles (Curcu-M) was 104 nM and 34 nM, respectively.

Differential scanning calorimetry (DSC) thermograms of curcumin-loaded PEG-Zein micelles are shown in FIG. 15. The absence of a melting peak of curcumin indicates encapsulation of curcumin inside the core of micelles. In vitro release of curcumin from PEG-Zein micelles is presented in FIG. 16. Release of curcumin was sustained for about 24 hours. Curcumin is known to have anti-cancer and anti-inflammatory activities, however the delivery of curcumin is limited by its poor water solubility. PEGylated zein micelles can be a suitable carrier for curcumin. FIG. 17 illustrates the in vitro cytotoxicity of curcumin (dissolved in 10% DMSO) and curcumin micelles (in PBS 7.4) in drug resistant human ovarian cancer cells (NCl/ADR-RES cells). The cell (2000 cells/well) were treated with 7.8 nM to 500 nM of curcumin for 4 days. On the fifth day cytotoxicity analysis was performed using the MTT assay. The curcumin-loaded micelles were more potent (3 fold more) than the pure curcumin.

Figure 18:
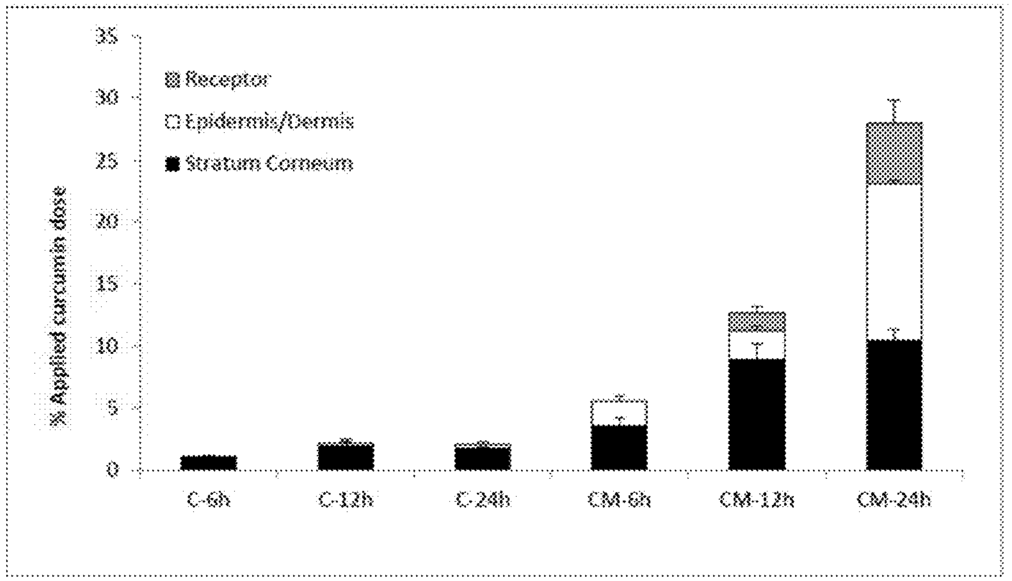
FIG. 18 illustrates the in vitro skin penetration of free curcumin (10% TWEEN 80 in PBS, pH 7.4; represented as "C" in the figure) and encapsulated curcumin (in PBS, pH 7.4; represented as "CM" in the figure) using excised porcine skin after different periods of treatment in a vertical diffusion cell. Excised porcine skin was sandwiched between the two compartments of a vertical diffusion cell. The receptor medium consisted of phosphate buffer (pH 7.4 with 20% ethanol) maintained at 37° C. and stirred using a magnetic bead. The skin was washed and tape-stripped 15-20 times using SCOTCH TAPE to remove stratum corneum (SC). The curcumin was extracted from the tape strips and the remaining skin (viable epidermis+dermis) using 90% ethanol. The amount of curcumin in the skin and in the receptor phase was determined by HPLC method.
Figure 19A:
FIG. 19 illustrates the confocal fluorescence XZ optical scan images (0-100 μm depth) of porcine skin after 6 hours of treatment with free curcumin (a) and curcumin encapsulated in PEG-zein micelles (b) and penetration of curcumin micelles (c) through hair follicles (xy surface view) and (d) curcumin fluorescence pixels quantified in the stratum corneum (SC) and viable epidermis. For SC 0-20 μm and for epidermis 20-100 μm XZ optical sections were used for quantifying the fluorescence pixels.
Figure 19B:
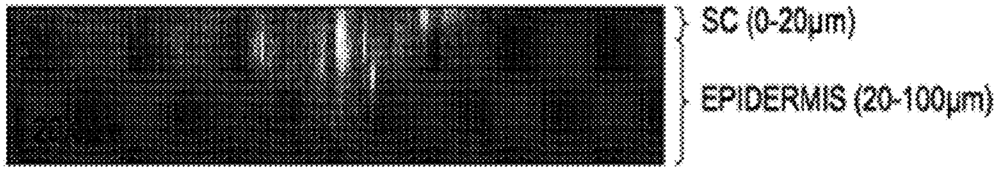
Figure 19C:
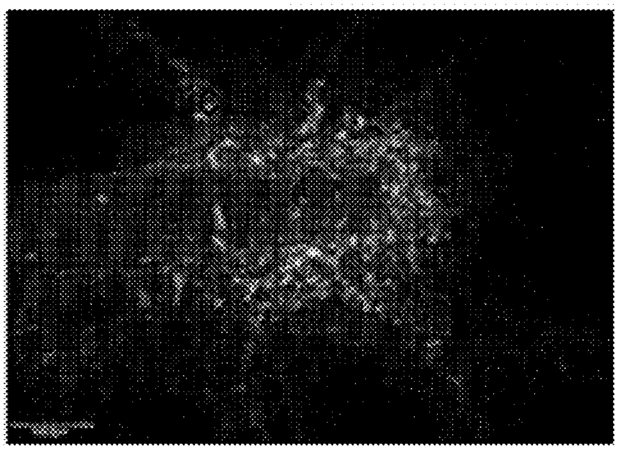
Figure 19D:
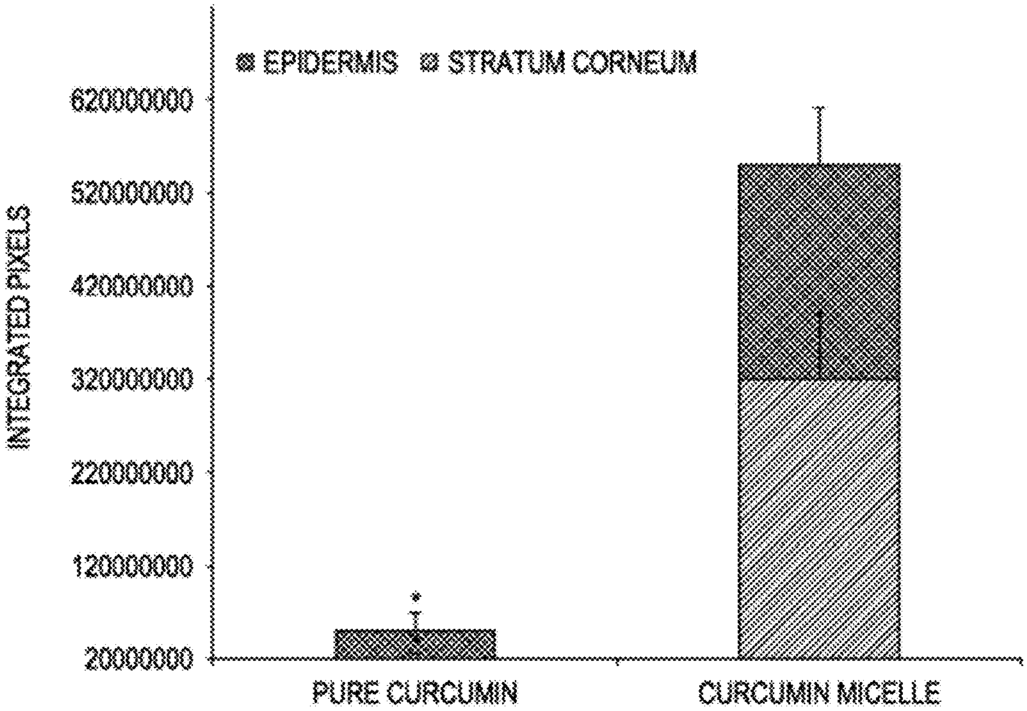

In Vitro Skin Penetration of Free Curcumin and Encapsulated Curcumin. As can be seen in FIG. 18, the skin penetration of curcumin was enhanced by 5-20 fold. Unlike the free curcumin, the skin penetration of curcumin micelles increased with treatment time. A significant amount of the applied (5-20%) dose penetrated the skin and curcumin was even found to cross and reach the receptor phase with longer treatment time.

As can be seen in FIG. 19, the curcumin micelles were mainly localized to the hair follicles (c). This is also evident from “b” where the fluorescence is observed in streaks from the surface to 100 μm deep inside the skin. The localization of PEG-zein micelles is particularly useful for treating follicular diseases such as acne, hair loss, seborrhetic eczema, follicullitis and some skin cancers. FIG. 19 (*d*) shows the fluorescence pixels in the stratum corneum (0-15 μm) and viable epidermis (20-100 μm). The encapsulation of curcumin in the micelles significantly increased the skin penetration of curcumin, Each value is avg.±SD (n=4). Excised porcine skin was sandwiched between the two compartments of a vertical diffusion cell. The receptor medium consisted of phosphate buffer (pH 7.4 with 20% ethanol) maintained at 37° C. and stirred using a magnetic bead. Free or encapsulated curcumin was applied on the skin for 6 hours. At the end of the study, the skin was washed and observed under confocal fluorescence microscope. The fluorescence pixels were quantified using IMAGEJ software.

Example 4

PEGylated Zein Micelles Encapsulating Nile Red

Nile red was used as a model hydrophobic dye (Sheihet et al. (2008), Int. J. Pharm. 350: 312-319) to study the application of PEG-zein nanomicelles as a skin delivery vehicle.

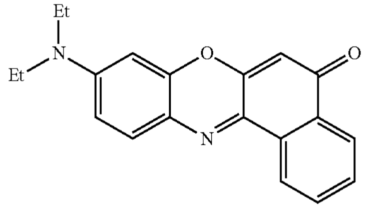

Nile red

Nile red has a molecular weight of 318.4, a Log P: 5, and a melting point of 203-205° C. It is practically insoluble in water, but is soluble in methanol, ethanol, and DMSO.

Figure 36:
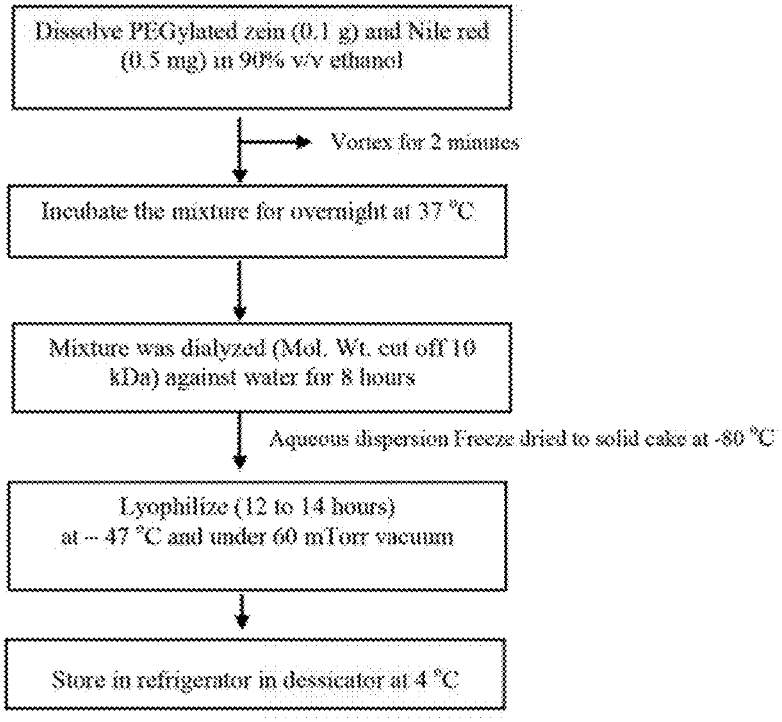
FIG. 36 illustrates steps for the preparation of Nile red-loaded PEGylated zein micelles using a dialysis method, according to an embodiment.

FIG. 36 illustrates the step wise preparation of Nile red-loaded PEG-Zein micelles using a dialysis method, according to one embodiment. PEG-Zein (0.1 g) and 0.5 mg of Nile red were dissolved in 20 mL of 90% ethanol. The mixture was incubated overnight (stirred at 50 rpm) at 37° C. to allow partitioning of the Nile red into the hydrophobic zein core. The mixture was then dialyzed (m.w. cut off 10,000 Da) against water (stirred at 100 rpm) at room temperature for 24 hours to remove any residual material. The resulting product was then frozen to −80° C. followed by freeze drying at −47° C. at 60 mTorr vacuum for 12 to 14 hours. The lyophilized product was stored in a dessicator at 4° C. Characteristics of the Nile red-loaded PEG-Zein micelles are shown below in Table 9.

TABLE 9

| Model compound | Particle size (nm) | PDI | Encapsulation Efficiency (%) |
|---|---|---|---|
| Nile red | 165 ± 7 | 0.21 ± 0.08 | 77 ± 11 |

Results are representative of triplicate samples (average ± SD); PDI = polydispersity index.

Figure 37:
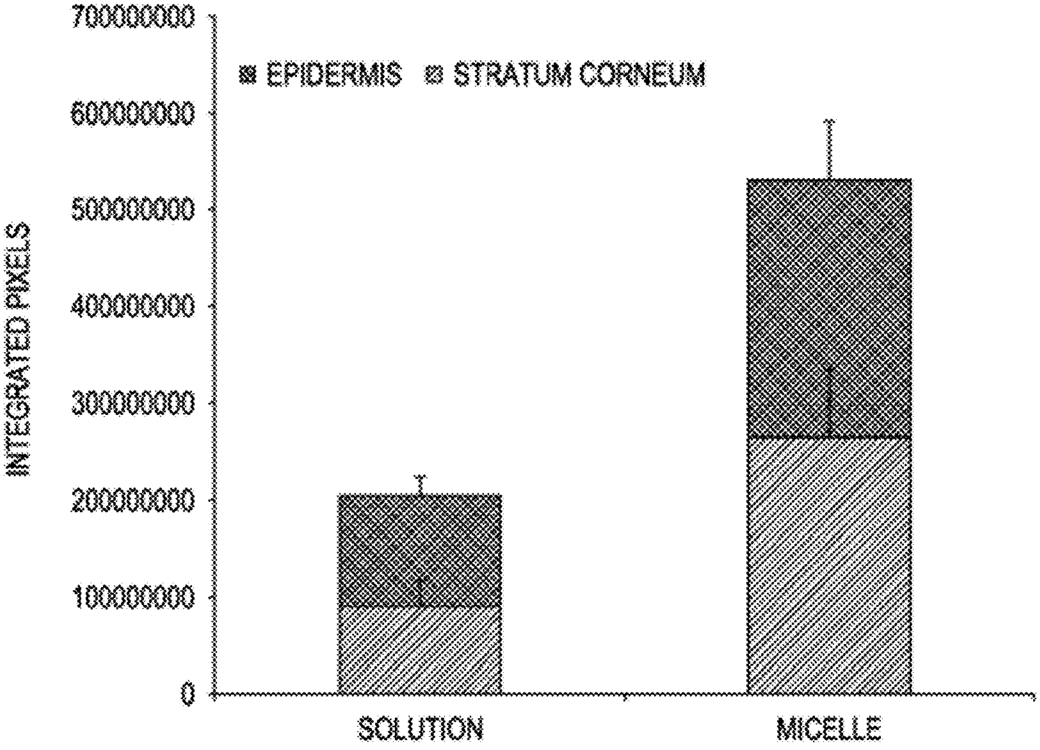
FIG. 37 illustrates the quantity of Nile red in the epidermis and stratum corneum (n=3). An in-vitro study was carried out using dermatomed porcine skin sandwiched between the two compartments of a vertical diffusion cell (PERMEGEAR™, Hellertown, Pa.). 100 μL of Nile red (250 ng) in 5% v/v Tween-80 solution or Nile red-loaded PEG-Zein micelles in water (250 ng) was added to the donor compartment. The receptor compartment consisted of PBS pH 7.4 maintained at 37° C. and stirred with a magnetic stir bar. After 6 hours the skin was removed and the fluorescence pixels were measured using confocal laser scanning microscopy (FLUOVIEW FV300™, Olympus ix70, Olympus, Center Valley, Pa.). Optical sections (xyz) were analyzed for fluorescence intensity in the Stratum Corneum (0-15 μm)

Nile red is a model lipophilic dye used to study skin penetration. The prepared Nile red loaded PEG-zein micelles had an average particle size of 165 nm with a low polydispersity index (0.21). The PEG zein micelles provided good encapsulation efficiency (77%). FIG. 37 illustrates the ability of the PEG-zein micelles to increase the skin penetration and skin retention of hydrophobic compounds. The data also demonstrates the application of PEG-zein micelles as a skin delivery vehicle for therapeutic and cosmetic agents.

The quantity of Nile red found in the epidermis and stratum corneum (n=3) was studied using dermatomed porcine skin. Porcine ears were obtained from the slaughter house in the Department of Animal and Range Sciences at South Dakota State University. The ears were collected immediately after slaughtering and were washed under tap water. Hair on the dorsal side was removed with a hair clipper. The skin was excised from the underlying cartilage using a scalpel and forceps. Fat adhering to the dermis side was carefully removed using a blunt scalpel and the skin was observed for any visible damage.

Skin was dermatomed to a thickness of 300 μm using a model B electric dermatome (PADGETT™ Instruments, St. Louis, Mo.). Dermatomed porcine skin was sandwiched between the donor and receptor chambers in a Franz diffusion cell (PERMEGEAR™, Hellertown, Pa.). The receptor chamber was filled with 6 mL of phosphate buffer (PB, pH 7.4) and was stirred using a magnetic stirbar. The receptor medium was maintained at 37° C. The donor chamber was loaded with 100 μL of Nile red (250 ng) in 5% v/v TWEEN-80 solution and Nile red micelles in water (equivalent to 250 ng of Nile red). After 6 hours, the skin samples were washed with PBS and mounted on a microscope slide for analysis by confocal laser scanning microscopy (CLSM).

The skin with the stratum corneum (SC) side up was examined using CLSM (FLUOVIEW FV300™, Olympus ix70, Olympus, Center Valley, Pa.). Nile red was excited using an Argon laser at an excitation wavelength of 488 nm. The images were observed using a PLAN-NEOFLUAR 40/0.85 objective. The xyz confocal images of the skin were scanned from surface (z=0 μm) to 100 μm at a step size of 5 μm/scan. All images were obtained with the same optical aperture, lens and scan speed.

Blank skin did not show any auto-fluorescence. Each representative image was selected from three to four skin samples and in each skin three to four different regions were scanned. Optical sections (xyz) were analyzed using FLUOVIEW™ software (Olympus, Center Valley, Pa.). The fluorescence intensity distribution in the confocal images was quantified by integrating the total pixels. At least three to four regions were analyzed for each skin. The pixels in the SC (0-15 μm) and viable epidermis (VE, 20-100 μm) were calculated separately. Treatment of skin with Nile red micelles showed significant increase in the skin penetration into both stratum corneum and viable epidermis compared to free Nile red solution (FIG. 37). This data shows that PEG-zein micelles can be used to deliver therapeutic or cosmetic agents to stratum corneum or viable epidermis to effectively treat various skin conditions.

Example 5

Additional Conjugate and Micelles Embodiments

Variations of the PEGylated zein micelles described herein can also be prepared. For example, in place of zein, other hydrophobic prolamine proteins, such as gliadin, hordein and kafirin may be used as the PEGylated proteins for micelle formation. Accordingly, PEGylated gliadin micelles, PEGylated hordein micelles, and PEGylated kafirin micelles can be prepared and used similar to the PEGylated zein micelles described herein.

Additionally, other amphiphilic protein conjugates can be prepared by replacing the PEG moiety of the PEGylated prolamine copolymer with another water soluble polymer, such as polyvinylpyrrolidone (PVP), polyglycolic acid (PGA), polyvinyl alcohol (PVA), chitosan, polysialic acid (PSA), polyethyleneimine (PEI), polyacrylic acid (PAA), polysaccharides such as dextran, and the like. These water soluble polymers can be conjugated to any of the hydrophobic prolamine proteins, such as zein, gliadin, hordein and kafirin, to form amphiphilic protein conjugates that self-assemble into micelles. When the micelles are formed in the presence of a dissolved therapeutic agent, drug loaded micelles can be prepared from these various amphiphilic protein conjugates and can be used as described for the PEGylated zein micelles.

Similarly, hydrophobic polymers can be conjugated to a prolamine. Such polymers can include, for example, polycaprolactone, poly lactic acid-co-glycolic acid, polypropylene oxide, polyaspartate, polygultamate, spermine, polylysine, or polyacrylates (for example, polymethacrylate, polydimethylamino ethyl acrylate, and the like). Fatty acids can also be conjugated to a prolamine to form a hydrophobic core. Examples of such fatty acids can include stearic acid, palmitic acid, phosphatidylethanolamine, or oleic acid. These polymers and/or fatty acids can be conjugated to any of the hydrophobic prolamine proteins, such as zein, gliadin, hordein and kafirin, to form protein conjugates that self-assemble into micelles. When the micelles are formed in the presence of a dissolved therapeutic agent, drug loaded micelles can be prepared from these various protein conjugates and can be used as described for the PEGylated zein micelles.

Other or further modifications can be made to the prolamine hydrophobic core or to the hydrophilic shell, such as a PEG shell. These may include conjugating stimuli responsive elements, such as polyhydroxyethylmethacrylate, to the core to prepare pH sensitive micelles or poly(N-isopropylacrylamide) to prepare thermosensitive micelles. In addition, the prolamine hydrophobic core or hydrophilic shell can be cross-linked, for example, using cross-linkers such as glutaraldehyde, genipin, citric acid, and the like, to control drug release and increase drug encapsulation yield and efficiency.

Example 6

Prolamine Micelles for Topical Delivery of Retinoids

Novel nanocarriers for topical delivery of retinol through skin for treating various dermatological conditions have been developed. Retinol (Vitamin A) and its derivatives (retinoids) are involved in various biological functions in the body including epidermal cell growth and differentiation, vision, immumomodulatory and anti-inflammatory effects (Summer, J Nutr 138:1835-1839, 2008). In particular, retinol and its derivatives are widely used for treating various dermatological conditions including acne, psoriasis, keratinization disorders, skin discoloration, and cutaneous malignancies (skin cancer and melanoma), as well as for wound healing and photoaging (Orfanos et al., Drug 53:358-388, 1997). Retinol is also used in cosmetic formulations to reduce wrinkles and treat cellulite (Orfanos et al., Drug 53:358-388, 1997). However, the use of retinol for cosmetic and dermatological applications is severely limited by its poor physicochemical properties and skin irritation potential (Melo et al., J Control Release 138:32-39, 2009; Kim et al., Toxicol Lett 146:65-73, 2003).

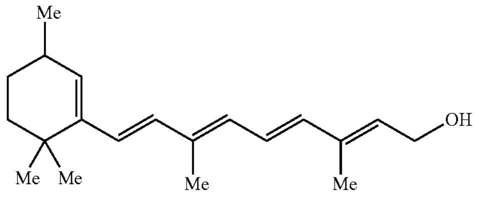

retinol

Retinol is lipophilic molecule (Log P 6.20), with poor water solubility and limited skin permeability. Furthermore, it is highly unstable in presence of light and moisture (see U.S. Pat. No. 5,851,538 (Froix et al.)) herein incorporated by reference in its entirety. The topical application of retinol causes severe local irritation manifested as mild erythema and stratum corneum peeling, leading to non-compliance among users (Kim et al., Toxicol Lett 146:65-73, 2003). Applicants have successfully addressed the delivery issues of retinol by encapsulating retinol in novel protein based micelles for topical application.

Novel nanocarriers have been developed from the corn protein zein, as described herein. One nanocarrier includes conjugating polyethylene glycol (PEG) to zein. The PEGylated zein forms self-assembled nanomicelles with a hydrophobic core and a hydrophilic shell. Zein displays hydrophobicity to skin keratin (Deo et al., Langmuir 19:5083-5088, 2003) and hence is a promising carrier for skin applications. Because zein is hydrophobic, it can be used to encapsulate hydrophobic retinoids inside nanoparticles (see, for example, WO 2009/137112, which is incorporated herein by reference in its entirety), or the micelles described herein can be used to encapsulate hydrophobic retinoids to provide a water removable formulation of the retinoid.

Applicants have prepared retinol loaded nanomicelles are in the size range of 180-220 nm with an encapsulation efficiency of 79-91%. Encapsulation of retinol in the micelles resulted in a water soluble formulation.

PEG-zein nanomicelles significantly enhanced the solid state and liquid state stability of retinol against moisture and light induced degradation. Retinol release was sustained up to 2 days from the PEG-zein nanomicelles.

PEG-zein nanomicelles enhanced the skin penetration of retinol compared to free retinol aqueous dispersion. Further, PEG-zein nanomicelles can be used to retain retinol in the skin layers for cosmetic and dermatological applications. A unique aspect of nanocarriers is the ability of the nanomicelles to address multiple market challenges for topical delivery of retinol. These challenges include providing 1) water soluble and water dispersible formulations of retinol, 2) enhanced stability of retinol against light and moisture induced degradation, 3) a freely flowing, colorless and non-hygroscopic powder of retinol, 4) sustained release formulations of retinol, 5) higher skin penetration and higher skin retention of retinol, and 6) non-irritating formulations of retinol.

Zein is a biodegradable US-FDA approved protein polymer with similar characteristics to skin keratin and is therefore a skin compatible nanocarrier. PEG is a US-FDA approved water soluble polymer. PEG-zein nanomicelles therefore provide a water washable topical formulation for retinol. The amphiphilic PEG-zein micelles serve as a carrier for transporting hydrophobic drugs such as retinol through the alternate hydrophobic and hydrophilic environment in the skin.

Retinol water solubility is significantly increased after encapsulation in nanomicelles. The retinol release can be sustained from zein nanomicelles leading to lower dose and reduced frequency of application. The encapsulation of retinol in zein nanomicelles significantly increases the shelf-life of retinol formulations. PEG-zein nanomicelles increase the flowability and dispersibility of retinol in solid and semi-solid formulations. Because retinol is a hygroscopic sticky powder, the encapsulation of retinol in nanomicelles can overcome the difficult handling and processing issues associated with retinol.

PEG-zein nanomicelles can enhance the skin penetration and retention of retinol in the layers of the skin for cosmetic and dermatological applications. Zein nanomicelles can enhance the skin penetration and retention of retinol in layers of the skin for cosmetic and dermatological applications. Encapsulation of retinol in nanomicelles masks the yellow color of retinol. This improves the aesthetic appeal of retinol formulations and prevents yellow staining. The lyophilized PEG-zein nanomicelles can be easily incorporated various topical formulation matrices, such as gels, creams, lotions and ointments.

The skin penetration studies were carried out with excised pig skin, which is similar to human skin in many important respects (Simon and Maibach, Skin Pharmacol Appl Physiol 13:229-234, 2000). In vivo studies in mice further demonstrate the ability of the nanomicelles to overcome the skin irritation of retinol. Advantages of using the nanomicelles in place of current commercial formulations include:

1. Solubilization. Retinol is a water insoluble hydrophobic compound. The encapsulation of retinol in PEG-zein nanomicelles is a water soluble/dispersible. Hence nanomicelles can be used to develop water washable retinol formulation for topical applications. Generally water washable formulation is preferred for cosmetic and dermatological applications.

2. Stabilization. Retinol is highly unstable in presence of moisture and light. This limits the shelf-life of retinol formulations and efficacy of the formulation during application. Encapsulation of retinol in PEG-zein nanomicelles can significantly enhance the stability and shelf-life of retinol formulations.

3. Sustained Release. Retinol release can be sustained from PEG-zein nanomicelles. Release can be sustained from 2 days to a week. This reduces the dose and frequency of application of retinol.

4. Skin penetration and retention. Retinol has poor skin penetration properties. Nanomicelles lead to enhanced skin penetration of retinol. Depending on the application, retinol can be retained in layers of the skin using nanomicelles for various dermatological/cosmetic applications.

5. Cosmecutical applications. Retinol loaded micelles can be used for cosmetic applications such as anti-aging, anti-wrinkle, and cellulite treatments.

6. Dermatological applications. Retinol loaded nanomicelles can be used for various dermatological conditions such as psoriasis, acne, wound-healing and cutaneous malignancies, such as skin cancer and melanoma.

7. Efficacious and safe formulation. Use of retinol loaded nanomicelles results in more efficacious treatments. Furthermore, the encapsulation of retinol in the nanomicelles significantly reduces the skin irritation caused by retinol. Skin irritation of retinol is a major issue for non-compliance for cosmetic and dermatological applications of retinol.

8. Platform technology for encapsulation of other retinoids. Various retinoids including retinol, retinoic acid, and their derivatives, can be encapsulated in prolamine nanomicelles for cosmetic and dermatological applications. Examples of various retinoids suitable for encapsulation include, but are not limited to, retinol, retinoic acid (such as 13-trans-retinoic acid (tretinoin), 13-cis-retinoic acid (isotretinoin), 9-cis-retinoic acid (alitretinoin)), retinaldehyde, etretnate, acitretin, retinol palmitate, and carotenoids such as a carotene, β-carotene, γ-carotene, β-cryptozanthin, lutein, and zeaxanthin.

9. Combination therapies. Retinol nanomicelles can be incorporated into other products, such as sunscreens, anti-psoriatic, anti-acne and skin-cancer products along with other drugs. Since retinol is encapsulated it will prevent the interaction with other agents. Other agents such as anti-oxidants, free-radical scavengers, anti-inflammatory agents can also be encapsulated along with retinol in nanomicelles.

Retinol Loaded PEG-Zein Nanomicelles.

Retinol (C20I-1300; 286.45 g/mol) has a melting point of 61-63° C., an activity of 3100 units/mg, and a Log P of 6.2. Retinol is practically insoluble in water, is soluble or partly soluble in ethanol, and is miscible with chloroform, ether and petroleum spirits.

Retinol is a cosmecutical/therapeutic agent used for various skin conditions including photoaging, acne, wound healing, melasma psoriasis, skin cancer, melanoma and other skin conditions (Orfanos et al., Drug 53:358-388, 1997). Retinol has poor water solubility and poor photostability (Melo et al., J Control Release 138:32-39, 2009; U.S. Pat. No. 5,851,538 (Froix et al.) herein incorporated by reference in its entirety). In addition, it also causes skin irritation (Kim et al., Toxicol Lett 146:65-73, 2003). Applicants have developed new zein based nanoparticulate topical formulations of retinol. Because zein has similar characteristics to skin keratin, it is used as a model protein to test the skin irritation of excipients used in topical formulations (zein test). Due to its similarity to skin keratin, zein nanocarriers are excellent delivery vehicles for retinol. In addition, PEG is a widely used material in skin formulations. Therefore, the combination of hydrophobic zein and hydrophilic PEG in PEG-zein micelles is an amphiphilic carrier that enables the transport of molecules through the skin via the alternate hydrophobic and hydrophilic regions in the skin.

This example demonstrates the preparation and characterization of retinol loaded zein nanomicelles, the improved solubility of retinol using PEG-zein nanomicelles, the improved stability of retinol by encapsulating in PEG-zein nanomicelles, the sustained release of retinol from zein micelles, the ability of zein nanomicelles to enhance skin penetration and skin retention of retinol, and the lack of or reduced skin irritation of the retinol micelle formulations compared to retinol itself 1. Preparation of the Retinol Loaded Nanomicelles. PEG-zein, retinol and BHT were dissolved in 90% ethanol and incubated overnight at 37° C. Later the dispersion was dialyzed against deionized water to remove the free retinol. Retinol loaded micelles were then lyophilized. Radiolabeled ($^3$H) retinol along with 'cold' retinol was used in this study. The size of the nanomicelles was about 180-220 nm and the encapsulation efficiency was 79 to 91%, depending on the PEG-zein/drug ratio and BHT concentration. In absence of BHT, the encapsulation efficiency was <35%. Table 6(10)-1 provides data for the characterization of retinol-loaded PEGylated zein micelles prepared using a dialysis method (e.g., see FIG. 38) and a thin film method (e.g., see FIG. 39), respectively.

TABLE 10-1

Characteristics of retinol-loaded PEGylated zein micelles prepared using a dialysis method and a thin film method, respectively.

| Sample No. | Retinol (% w/w) | BHT (% w/w) | Particle size (nm) | PDI | Encapsulation Efficiency (%) |
|---|---|---|---|---|---|
| Dialysis method | | | | | |
| 1 | 0.05 | . . . | 225.3 ± 8.3 | 0.374 ± 0.05 | 28.7 ± 3.8 |
| 2 | 0.01 | . . . | 194.4 ± 5.4 | 0.390 ± 0.06 | 28.2 ± 2.2 |
| 3 | 0.015 | . . . | 231.5 ± 9.9 | 0.459 ± 0.05 | 33.1 ± 2.8 |
| 4 | 0.02 | . . . | 232.2 ± 9.7 | 0.813 ± 0.10 | 35.0 ± 2.2 |
| 5 | 0.005 | 0.005 | 192.2 ± 7.5 | 0.269 ± 0.03 | 90.8 ± 3.5 |
| 6 | 0.01 | 0.01 | 191.3 ± 5.9 | 0.272 ± 0.06 | 83.3 ± 3.1 |
| 7 | 0.015 | 0.015 | 186.0 ± 7.7 | 0.285 ± 0.03 | 80.8 ± 2.5 |
| 8 | 0.02 | 0.02 | 197.0 ± 6.7 | 0.206 ± 0.02 | 78.6 ± 1.9 |
| 9 | 0.02 | 0.04 | 189.5 ± 10.3 | 0.322 ± 0.07 | 77.1 ± 6.44 |
| Film method | | | | | |
| 1 | 0.015 | 0.015 | 791.5 ± 67.1 | 0.714 ± 0.1 | 75.4 ± 8.67 |

Results are representative of triplicate samples (average ± SD); PDI = polydispersity index.

2. Increased Solubility/Dispersibility of Retinol in Aqueous Solution. Free retinol was not dispersible in water and settled at the bottom of the vial after attempted dispersion of the agent (FIG. 40). On the other hand, retinol loaded PEG-zein nanomicelles easily dispersed in water. The solubility of retinol in phosphate buffer (pH 7.4) was significantly enhanced after encapsulation in nanomicelles. A 10 µg/mL sample of retinol (retinol equivalent) retinol micelles in phosphate buffer (pH 7.4) showed comparable UV absorbance (320 nm) to 10 µg/mL of free retinol in 20% methanol. Very little absorbance was observed in the 10 µg/mL dispersion of retinol in phosphate buffer (pH 7.4).

3. Release of Retinol from PEG-Zein Nanomicelles. Release studies of the retinol from nanomicelles were carried out in phosphate buffer saline (PBS; pH 7.4). The concentration of retinol was analyzed using UV Spectrophotometer at 320 nm, and the release studies were carried out in triplicate. Retinol release was sustained for up to 48 hours from the nanomicelles as shown in FIG. 41.

4. Stability of Retinol Loaded Zein Nanomicelles. Retinol is a yellow colored powder. It is hygroscopic at ambient conditions and quickly becomes sticky. The encapsulated retinol is colorless and free flowing, and is far less hygroscopic (FIG. 42). The retinol sample shown in FIG. 42 was bright yellow and the nanomicelle formulation was white, demonstrating that encapsulation masks the bright yellow color of retinol. The nanomicelle formulation also resulted in a more free flowing powder than pure retinol.

The stability of retinol nanomicellar formulations under ambient conditions and in dark was studied for a period of one week. The solid stability of retinol and retinol loaded nanomicelles (lyophilized powder) were also studied for one week. For liquid state stability, free retinol or retinol loaded nanomicelles was dispersed in phosphate buffer (pH 7.4) and the retinol concentration was measured for a week using a UV spectroscopy method (at 320 nm). Retinol was found to follow first order kinetics and the half-life was determined. The following results were obtained as shown in Tables 10-3 and 10-4 and FIGS. 43, 44, 45, and 46.

PEG-zein nanomicelles protected retinol against photodegradation and moisture induced degradation. The encapsulated retinol showed enhanced stability compared to free retinol in the solid state and in liquid state. Inclusion of BHT as an antioxidant further enhanced the stability of encapsulated retinol. Finally, the shelf-life of retinol was significantly enhanced by encapsulation in nanomicelles.

TABLE 10-3

Solid state stability of free and encapsulated retinol.

| Substance | Light ($t_{1/2}$ in hrs) | Dark ($t_{1/2}$ in hrs) |
|---|---|---|
| Retinol solid | 52.75 | 63 |
| Retinol micelles | 86.63 | 112 |
| Retinol micelles with BHT | 173.25 | 1155 |

TABLE 10-4

Liquid state stability of free and encapsulated retinol in phosphate buffer (pH 7.4).

| Substance | Light ($t_{1/2}$ in hrs) | Dark ($t_{1/2}$ in hrs) |
|---|---|---|
| Retinol | 16.11 | 20.83 |
| Retinol + BHT | 35.25 | 43.42 |
| Retinol micelles | 37 | 94.88 |
| Retinol micelles with BHT | 99 | 219.5 |

5. Skin Penetration of Retinol and Encapsulated Retinol. The skin penetration of retinol and encapsulated retinol was studied using excised porcine ear skin using a Franz diffusion cell. Radiolabeled ($^3$H) retinol along with 'cold' retinol was used in this study. The amount of retinol in the skin homogenate and receptor medium at the end of 48 hours was estimated using radiochemical analysis. The experiments were repeated 6 times (±SD). As can been seen in FIG. 47, the encapsulated retinol resulted in greater retention of retinol in the skin. Micelles resulted in approximately 5 fold increased skin retention of retinol. The ratio of "retinol in skin to receptor" was 3 and 6.5, for free retinol and retinol micelles, respectively. The results show that micelles increased the overall skin penetration and retention of retinol.

To demonstrate the follicular targeting of retinol a skin sandwich model was used. In the sandwich skin (see FIG. 48), the follicular pathways are blocked by the stratum corneum sandwiched over the epidermis. In the sandwich skin model the amount of retinol transported into the receptor compartment was reduced both for free and micelle encapsulated retinol compared to conventional skin epidermis penetration studies. However, there was significant reduction in the transport of retinol from the micelles indicating that a significant fraction of retinol micelles is transported through the hair follicles. Given the use of retinol to treat acne (acne mainly originates from the hair follicles), the retinol micelles will have the advantage of targeting retinol to the disease site in the hair follicles.

In summary, PEG-zein nanomicelles significantly increased the aqueous solubility and dispersibility of retinol. Encapsulation of retinol in nanomicelles resulted in a free flowing colorless powder, unlike free retinol, which is a yellow, sticky and hygroscopic powder. Zein nanomicelles effectively sustained the release of retinol. Photostability and hydrolytic stability of retinol is significantly enhanced by encapsulating in zein nanomicelles, which was further enhanced by addition of BHT as an antioxidant, and PEG-zein nanomicelles resulted in higher skin retention of retinol. The nanomicelles can also reduce the skin irritation of retinol.

Preparation of a Cream Formulation for Retinol Micelles. To demonstrate the feasibility of a skin formulation for delivery for commercial development, a commercial cream base (MEDCO Labs) was used to incorporate free retinol or retinol encapsulated in zein nanomicelles. Cream base contains stearyl alcohol (14%, cetyl esters was (3.5%), glyceryl monostearate (2%), polyoxyethylene stearyl ether (3%), sorbitol (10%), isopropyl palmitate (2%), methyl paraben (0.16%), propyl paraben (0.4%) and purified water (65%). Retinol equivalent to 0.1% was weighed and transferred to watch glass and mixed homogenously using glass rod by geometric dilution. Other formulation, including but not limited to, oil-water cream, water in oil cream, ointment, gel, and the like may be used. The mixture was spiked with 0.05 μCi of $^3$H-retinol and mixed thoroughly in the cream. Finally, the prepared cream formulations were transferred to glass vials and stored until use.

TABLE 11

| Retinol cream formulations | |
|---|---|
| Retinol (0.1% w/w) cream - 1 g | |
| Retinol | 0.001 g |
| Cream base | 0.800 g |
| Retinol micelle cream (0.1% w/w) cream - 1 g | |
| Retinol micelles | 0.0625 g |
| Cream base | 0.9375 g |

Stability of retinol micellar cream formulation was measured for a period of one-month (see FIG. 49). As shown in the Figure, the formulation remained stable and did not show any degradation at room temperature.

In Vitro Release of Retinol from Cream Formulations. About 40 mg of the cream base and micelle cream were place in a vertical diffusion cell dialysis membrane (MWCO~8,000-10,000 Da) for the release study, the receptor medium consisted of pH 7.4 buffer. Samples were collected from the receptor medium and analyzed by radiochemical method using $^3$H retinol. Each data point represents mean±SD (n=3). As can be seen in FIG. 50, more retinol is released from the plain cream compare to the micelle cream.

In Vitro Skin Penetration. Excised human skin was sandwiched between the two compartments of a vertical diffusion cell. The receptor medium consisted of phosphate buffer (pH 7.4) maintained at 37° C. and stirred using a magnetic bead. Free or retinol encapsulated micelle cream formulation was loaded in the donor chamber. The formulation was applied for 6 hours and then the formulation was removed and the penetration study was continued for 48 hours. At the end of the study, the retinol concentration in the skin and receptor compartment was measured by radiochemical method using $^3$H labeled retinol. The skin was digested using 0.1M sodium hydroxide to determine the retinol concentration. As can be seen in FIG. 51, for the plain cream, more retinol was present in the receptor compartment than in the skin. In contrast, the micelle cream showed the opposite, where more retinol was found in the skin than in the receptor compartment.

Skin Irritation of Retinol and Encapsulated Retinol Cream Formulation. The skin irritation of standard vs. encapsulated formulations can be tested in vivo in SKH-1 hairless mice using treatments groups as listed in Table 12.

TABLE 12

Treatment groups for a skin irritation study.

| Groups | Treatment |
|---|---|
| Group 1 | Control (no treatment) |
| Group 2 | Retinol cream |
| Group 3 | Blank PEG-zein micelles cream |
| Group 4 | Retinol nanomicelles cream |
| Group 5 | Sodium lauryl sulfate cream (positive control) |

The retinol cream formulations (0.5 g of 0.1% w/v retinol equivalent) were applied to the backs of SKH-1 hairless mice everyday for five (5) days. The transepidermal water loss (TEWL) values were measured using an TEWA meter (Delfin) every day before applying the formulation. The increase in TEWL is a measure of skin irritation and as can be seen in FIG. 52, the retinol encapsulated in micelles showed no skin irritation and was comparable to negative control (i.e., no treatment). On the other hand the free retinol cream shows skin irritation. Sodium lauryl sulfate (SLS), a known skin irritant, was used as the positive control.

In Vivo Topical Bioavailability. The cream formulations were applied on the back skin of mice under isoflurane anesthesia. After euthanizing the animals, the skin was tape-stripped using SCOTCH TAPE to remove stratum corneum. The amount of retinol in skin (stratum corneum and epidermis/dermis) and blood were determined using $^3$H retinol by radiochemical analysis. As can be seen in FIG. 53, the micelle encapsulated retinol was retained in the skin with no systemic absorption into the blood. Values are mean±SD (n=3).

Example 7

Casein Micelles

Casein is a milk protein that can form micelles under appropriate conditions. Although some studies have described the use of casein micelles as a delivery vehicle, casein micelles have not been used as delivery agents for skin applications. Casein can be combined with PEG-zein to form novel mixed micelles.

The general steps for preparing retinol loaded β-casein micelles are as follows. β Casein (20 mg) and retinol (0.1 mg in 600 μL of ethanol) may be dissolved in 10 mL of 0.1M PBS pH 7.0. The mixture may be incubated overnight at about 37° C., followed by lyophilization (e.g., for about 24 hours) at ~100° C. under 100 mTorr vacuum. The resulting micelle powder may be stored in a dessicator at about 2-8° C. for an extended period of time. Table 13 below illustrates various characteristics of retinol-loaded β-casein micelles. For the preparation of retinol loaded β-casein micelle, retinol concentrations can range from about 0.005 to about 0.05% w/w. β-Casein concentrations ranged from about 0.15-0.25% w/v.

TABLE 13

Characteristics of retinol-loaded β-casein micelles.

| Sample No. | Retinol (% w/w) | BHT (% w/w) | Particle size (nm) | PDI | Encapsulation Efficiency (%) |
|---|---|---|---|---|---|
| 1 | 0.005 | — | 207.4 | 0.656 | 9.74 |
| 2 | 0.015 | — | 109.1 | 0.616 | 10.28 |
| 3 | 0.005 | 0.005 | 76.9 | 0.626 | 10.25 |
| 4 | 0.015 | 0.015 | 68.9 | 0.510 | 11.06 |

Casein can also be used to prepare Nile red containing micelles (see, FIG. 54). Table 14 provides characteristics of such micelles.

TABLE 14

| Sample name | Particle Size (nm) | PI | Encapsulation Efficiency (%) |
|---|---|---|---|
| Nile red-casein micelles | 245 ± 15 nm | 0.38 ± 0.41 | 78 ± 5% |

As seen in FIG. 55, the encapsulation of Nile red in the casein micelles significantly increased the skin penetration of Nile red. Excised porcine skin was sandwiched between the two compartments of a vertical diffusion cell. The receptor medium consisting of phosphate buffer (pH 7.4) was maintained at 37° C. and stirred using a magnetic bead. Free or encapsulated Nile red was applied on the skin for 6 hours. At the end of the study, the skin was washed and observed under a confocal fluorescence microscope. The fluorescence in the SC (0-15 μm) and viable epidermis (20-100 μm) was quantified using IMAGEJ software. Each value is avg.±SD (n=4). Significant difference at $p<0.05$.

Example 8

Pharmaceutical Dosage Forms

The following formulations illustrate representative pharmaceutical dosage forms that may be used for the therapeutic or cosmetic administration of a micelle formulation described herein, which can be an aqueous dispersion or a lyophilized powder (hereinafter referred to as ‘Composition X’):

| (i) Tablet 1 | mg/tablet |
|---|---|
| ‘Composition X’ | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| ‘Composition X’ | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| ‘Composition X’ | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| ‘Composition X’ | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| ‘Composition X’ | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| ‘Composition X’ | 20 |
| Oleic acid | 10 |
| Trichloromonofluoromethane | 5,000 |
| Dichlorodifluoromethane | 10,000 |
| Dichlorotetrafluoroethane | 5,000 |
| (vii) Topical Gel 1 | wt. % |
| ‘Composition X’ | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| ‘Composition X’ | 5% |
| Methylcellulose | 2% |
| Methyl paraben | 0.2% |
| Propyl paraben | 0.02% |
| Purified water | q.s. to 100 g |

| (ix) Topical Ointment | wt % |
|---|---|
| ‘Composition X’ | 5% |
| Propylene glycol | 1% |
| Anhydrous ointment base | 40% |

-continued

| | |
|---|---|
| Polysorbate 80 | 2% |
| Methyl paraben | 0.2% |
| Purified water | q.s. to 100 g |
| (x) Topical Cream 1 | wt. % |
| 'Composition X' | 5% |
| White bees wax | 10% |
| Liquid paraffin | 30% |
| Benzyl alcohol | 5% |
| Purified water | q.s. to 100 g |
| (xi) Topical Cream 2 | wt. % |
| 'Composition X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraban | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Composition X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention. Although the invention has been described with reference to the above examples, it will be understood that modifications and variations are encompassed within the spirit and scope of the invention. Accordingly, the invention is limited only by the following claims.

What is claimed is:

1. A stable micelle comprising: (i) an amphiphilic copolymer containing zein covalently conjugated to PEG and (ii) one or more cargo molecules, wherein the one or more cargo molecules are selected from the group consisting of a buffer, a hydrophobic agent, a therapeutic agent, an antioxidant, an anti-inflammatory drug, an anticancer drug, a cosmetic, a pharmaceutical, a nutraceutical, a pesticide, an insecticide, an herbicide, an antiseptic, a diagnostic agent, a food additive, a fragrance, a dye, and a textile.

2. The stable micelle of claim 1, wherein said hydrophobic agent is selected from the group consisting of abietic acid, aceglatone, acenaphthene, acenocoumarol, acetohexamide, acetomeroctol, acetoxolone, acetyldigitoxins, acetylene dibromide, acetylene dichloride, acetylsalicylic acid, alantolactone, aldrin, alexitol sodium, allethrin, allylestrenol, allyl sulfide, alprazolam, aluminum bis(acetylsalicylate), ambucetamide, aminochlothenoxazin, aminoglutethimide, amyl chloride, androstenediol, anethole trithone, anilazine, anthralin, Antimycin A, aplasmomycin, arsenoacetic acid, asiaticoside, astemizole, aurodox, aurothioglycanide, 8-azaguanine, azobenzene; baicalein, Balsam Peru, Balsam Tolu, barban, baxtrobin, bendazac, bendazol, bendroflumethiazide, benomyl, benzathine, benzestrol, benzodepa, benzoxiquinone, benzphetamine, benzthiazide, benzyl benzoate, benzyl cinnamate, bibrocathol, bifenox, binapacryl, bioresmethrin, bisabolol, bisacodyl, bis(chlorophenoxy)methane, bismuth iodosubgallate, bismuth subgallate, bismuth tannate, Bisphenol A, bithionol, bornyl, bromoisovalerate, bornyl chloride, bornyl isovalerate, bornyl salicylate, brodifacoum, bromethalin, broxyquinoline, bufexamac, butamirate, butethal, buthiobate, butylated hydroxyanisole, butylated hydroxytoluene; calcium iodostearate, calcium saccharate, calcium stearate, capobenic acid, captan, carbamazepine, carbocloral, carbophenothin, carboquone, carotene, carvacrol, cephaeline, cephalin, chaulmoogric acid, chenodiol, chitin, chlordane, chlorfenac, chlorfenethol, chlorothalonil, chlorotrianisene, chlorprothixene, chlorquinaldol, chromonar, cilostazol, cinchonidine, citral, clinofibrate, clofazimine, clofibrate, cloflucarban, clonitrate, clopidol, clorindione, cloxazolam, coroxon, corticosterone, coumachlor, coumaphos, coumithoate cresyl acetate, crimidine, crufomate, cuprobam, cyamemazine, cyclandelate, cyclarbamate cymarin, cypernethril; dapsone, defosfamide, deltamethrin, deoxycorticocosterone acetate, desoximetasone, dextromoramide, diacetazoto, dialifor, diathymosulfone, decapthon, dichlofluani, dichlorophen, dichlorphenamide, dicofol, dicryl, dicumarol, dienestrol, diethylstilbestrol, difenamizole, dihydrocodeinone enol acetate, dihydroergotamine, dihydromorphine, dihydrotachysterol, dimestrol, dimethisterone, dioxathion, diphenane, N-(1 ,2-diphenylethyl)nicotinamide, dipyrocetyl, disulfamide, dithianone, doxenitoin, drazoxolon, durapatite, edifenphos, emodin, enfenamic acid, erbon, ergocominine, erythrityl tetranitrate, erythromycin stearate, estriol, ethaverine, ethisterone, ethyl biscoumacetate, ethylhydrocupreine, ethyl menthane carboxamide, eugenol, euprocin, exalamide; febarbamate, fenalamide, fenbendazole, fenipentol, fenitrothion, fenofibrate, fenquizone, fenthion, feprazone, flilpin, filixic acid, floctafenine, fluanisone, flumequine, fluocortin butyl, fluoxymesterone, fluorothyl, flutazolamn, fumagillin, 5-furfuryl-5-isopropylbarbituric acid, fusafungine, glafenine, glucagon, glutethimide, glybuthiazole, griseofulvin, guaiacol carbonate, guaiacol phosphate, halcinonide, hematoprophyrin, hexachlorophene, hexestrol, hexetidine, hexobarbital, hydrochlorothiazide, hydrocodone, ibuproxam, idebenone, indomethacin, inositol niacinate, iobenzamic acid, iocetamic acid, iodipamide, iomeglamic acid, ipodate, isometheptene, isonoxin, 2-isovalerylindane-1 ,3-dione, josamycin, 11-ketoprogesterone, laurocapram, 3-0-lauroylpyridoxol diacetate, lidocaine, lindane, linolenic acid, liothyronine, lucensomycin, mancozeb, mandelic acid, isoamyl ester, mazindol, mebendazole, mebhydroline, mebiquine, melarsoprol, melphalan, menadione, menthyl valerate, mephenoxalone, mephentermine, mephenyloin, meprylcaine, mestanolone, mestranol, mesulfen, metergoline, methallatal, methandriol, methaqualone, 3-methylcholanthrene, methylphenidate, 17-methyltestosterone, metipranolol, minaprine, myoral, naftalofos, naftopidil, naphthalene, 2-naphthyllactate, 2-(2-naphthyloxy) ethanol, naphthyl salicylate, naproxen, nealbarbital, nemadectin, niclosamide, nicoclonate, nicomorphine, nifuroquine, nifuroxazide, nitracrine, nitromersol, nogalamycin, nordazepamn, norethandrolone, norgestrienone; octaverine, oleandrin, oleic acid, oxazepam, oxazolam, oxeladin, oxwthazaine, oxycodone, oxymesterone, oxyphenistan acetate, paraherquamide, parathion, pemoline, pentaerythritol tetranitrate, pentylphenol, perphenazine, phencarb amide, pheniramine, 2-phenyl 6-chlorophenol, phentlmethylbarbituric acid, phenyloin, phosalone, phthalylsulfathiazole, phylloquinone, picadex, pifamine, piketopfen, piprozolin, pirozadil, plafibride, plaunotol, polaprezinc, polythiazide, probenecid, progesterone, promegestone, propanidid, propargite, propham, proquazone, protionamide, pyrimethamine, pyrimithate, pyrvinium pamoate, quercetin, quinbolone, quizalofo-ethyl, rafoxanide, rescinnamine, rociverine, runnel, salen, scarlet red, siccanin, simazine, simetride, sobuzoxane, solan, spironolactone, squalene, stanolone, sucralfate, sulfabenz, sulfaguanole, sulfasalazine, sulfoxide, sulpiride, suxibuzone, talbutal, terguide, testosterone, tetrabromocresol, tetrandrine, thiacetazone, thiocolchicine, thioctic acid, thioquinox, thioridazine, thiram, thymyl N isoamylcarbamate, tioxidazole, tioxolone, tocopherol, tolciclate, tolnaftate, triclosan, triflusal, triparanol, ursolic acid, valinomycin, veraparnil, vinblastine, vitamin A, vitamin D, vitamin E, xenbucin, xylazine, zaltoprofen, zearalenone, and combinations thereof.

3. The stable micelle of claim 1, wherein the nutraceutical is selected from the group consisting of a small molecule, a macromolecule, a protein, a nucleic acid, a growth factor, a hormone, a drug, a cell, and combinations thereof.

4. The stable micelle of claim 3, wherein the nutraceutical is selected from a vitamin D, vitamin A, vitamin E, α-carotene, β-carotene, γ-carotene, β-cryptozanthin, lutein, zeaxanthin, or linolenic acid.

5. The stable micelle of claim 1, wherein the anticancer drug is paclitaxel or docetaxel.

6. The stable micelle of claim 1, wherein said one or more cargo molecules are encapsulated within the micelle, covalently or non-covalently complexed to the zein moiety, covalently or non-covalently complexed to the PEG moiety, or a combination thereof.

7. The stable micelle of claim 1, wherein the critical micelle concentration (CMC) of the copolymer in water is between about 0.015 g/L and about 0.035 g/L, and wherein said stable micelle has a biodegradable hydrophilic shell-hydrophobic core structure.

8. A nutraceutical composition containing:

a stable micelle comprising:

(i) an amphiphilic copolymer containing zein covalently conjugated to PEG and (ii) one or more cargo molecules, wherein the one or more cargo molecules are selected from the group consisting of a vitamin D, vitamin A, vitamin E, α-carotene, β-carotene, γ-carotene, β-cryptozanthin, lutein, zeaxanthin, linolenic acid, and combinations thereof.

9. The nutraceutical composition of claim 8, wherein said nutraceutical composition containing the micelle is a sterile aqueous solution, sterile dispersion, or sterile powder.

10. The nutraceutical composition of claim 9, wherein the stable micelle particle size is from about 10 nm to about 300 nm.

11. The nutraceutical composition of claim 8, wherein the one or more cargo molecules comprise a carotinoid, wherein the carotinoid is β-carotene, and wherein said nutraceutical composition further comprises a carrier selected from a solid, liquid, gel, cream, ointment, or paste.

12. The nutraceutical composition of claim 8, wherein the nutraceutical composition is combined with a food additive or liquid dispersion medium.

13. A pharmaceutical composition comprising the stable micelle of claim 5, wherein the pharmaceutical composition is formulated for intravenous administration.

14. The nutraceutical composition of claim 8, wherein the composition comprises at least 0.1 wt % of said one or more cargo molecules.

15. The nutraceutical composition of claim 8, wherein the composition contains a micelle to cargo molecule ratio between about 10:1 to about 100:1.

16. The nutraceutical composition of claim 8, wherein the composition contains a cargo molecule at between about 2% to about 60% or about 0.5% to about 10% of the weight of a given dosage form.

17. The nutraceutical composition of claim 8, further comprising a carrier, excipient, and/or diluent selected from the group consisting of water, ethanol, a polyol, mineral oils, vegetable oils, nontoxic glyceryl esters, and mixtures thereof.

18. A method treating a disease comprising administering an effective amount of a pharmaceutical composition containing:

a stable micelle comprising:

(i)An amphiphilic copolymer containing zein covalently conjugated to PEG and (ii) One or more cargo molecules, wherein the one or more cargo molecules are selected from the group consisting of a buffer, paclitaxel, docetaxal, doxorubicin, melphalan, a vitamin D, and irinotecan, and optionally one or more additional therapeutic agents.

19. The method of claim 18, wherein the disease is breast cancer, lung cancer, pancreatic cancer, prostate cancer, or colon cancer, and optionally further comprises administering an effective amount of one or more additional therapeutic agents.

20. The method of claim 19, wherein the cancer exhibits P-glycoprotein (P-gp)-dependent multidrug resistance (MDR), and said cancer exhibits over-expression of P-gp.

21. The method of claim 18, wherein the disease is psoriasis, and optionally further comprises administering and effective amount of one or more additional therapeutic agents.

22. A liquid or solid composition comprising the stable micelle of claim 8.

23. The liquid or solid composition of claim 22, wherein the stable micelle is prepared by: dissolving zein and a monoalkylated polyethylene glycol (mPEG) in a hydroalcoholic solvent to form a first mixture;

heating the first mixture to form covalently conjugated PEGylated-zein and optionally quenching excess reactive groups of the PEG in the hydroalcoholic suspension;

adding a buffer to the first mixture to precipitate the PEGylated-zein from the hydroalcoholic solvent and dialyzing the PEGylated-zein against an aqueous solution; lyophilizing the resulting dialysate;

dissolving the lyophilized PEGylated-zein in a hydroalcoholic solvent to form a second mixture;

and either:

(a) dialyzing the second mixture against an aqueous buffer to form a stable micelle or (b) evaporating the second mixture to form a dry film, hydrating the film with an aqueous buffer; and sonicating the hydrated film to form a stable micelle, wherein the critical micelle concentration (CMC) of the PEGylated-zein in water is between about 0.015 g/L to about 0.035 g/L.

24. The liquid or solid composition of claim 23, wherein the stable micelle contains at least one of the structures as represented in Formulae I-V:

Z-(PEG)n (I);

Z-g-PEG (graft copolymer) (II);

Z-b-PEG (diblock copolymer) (III);

Z-b-PEG-b-Z (triblock copolymer) (IV); or

PEG-b-Z-b-PEG (triblock copolymer) (V), wherein Z is zein, PEG is a polyethylene glycol moiety having a molecular weight of at least about 3 kDa, n is about 1 to about 100, b is a block copolymer, and g is a graft copolymer.

25. The preparation method of claim 23.

26. A stable micelle prepared by the method of claim 25.

27. A sealed container comprising a pharmaceutical composition for injection comprising paclitaxel and a pharmaceutically acceptable carrier, wherein the pharmaceutically acceptable carrier comprises an amphiphilic copolymer containing zein covalently conjugated to PEG, wherein said carrier and paclitaxel in the composition are formulated as micelles, wherein the micelles have a particle size of between about 10 nm to about 300 nm, and wherein the composition contains a micelle to paclitaxel ratio between about 10:1 to about 100:1.

* * * * *